United States Patent
Takahashi et al.

(10) Patent No.: US 11,279,880 B2
(45) Date of Patent: Mar. 22, 2022

(54) POLYMERIZABLE LIQUID CRYSTAL COMPOSITION, OPTICALLY ANISOTROPIC FILM, OPTICAL FILM, POLARIZING PLATE, IMAGE DISPLAY DEVICE, AND ORGANIC ELECTROLUMINESCENT DISPLAY DEVICE

(71) Applicant: FUJIFILM Corporation, Tokyo (JP)

(72) Inventors: Keita Takahashi, Kanagawa (JP); Mayumi Nojiri, Kanagawa (JP); Ayako Muramatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 143 days.

(21) Appl. No.: 16/423,619

(22) Filed: May 28, 2019

(65) Prior Publication Data

US 2019/0276742 A1    Sep. 12, 2019

Related U.S. Application Data

(63) Continuation of application No. PCT/JP2017/042411, filed on Nov. 27, 2017.

(30) Foreign Application Priority Data

Nov. 29, 2016   (JP) ............................. JP2016-231479

(51) Int. Cl.
*C09K 19/54*   (2006.01)
*C09K 19/38*   (2006.01)
(Continued)

(52) U.S. Cl.
CPC ........ *C09K 19/3814* (2013.01); *C07D 277/82* (2013.01); *C07D 311/72* (2013.01);
(Continued)

(58) Field of Classification Search
CPC ..................................................... C09K 19/54
See application file for complete search history.

(56) References Cited

U.S. PATENT DOCUMENTS

| | | | | |
|---|---|---|---|---|
| 2015/0285979 A1* | 10/2015 | Aimatsu | ............ | C09K 19/3876 349/194 |
| 2015/0330602 A1* | 11/2015 | Yonemoto | .............. | G02B 6/005 349/71 |

(Continued)

FOREIGN PATENT DOCUMENTS

| | | |
|---|---|---|
| CN | 101107559 A | 1/2008 |
| CN | 104769464 A | 7/2015 |

(Continued)

OTHER PUBLICATIONS

International Search Report Issued in PCT/JP2017/042411 dated Dec. 26, 2017.

(Continued)

*Primary Examiner* — Chanceity N Robinson
(74) *Attorney, Agent, or Firm* — Edwards Neils LLC; Jean C. Edwards, Esq.

(57) ABSTRACT

A polymerizable liquid crystal composition capable of manufacturing an optically anisotropic film having excellent light fastness; and an optically anisotropic film, an optical film, a polarizing plate, an image display device, and an organic electroluminescent display device, each of which uses the polymerizable liquid crystal composition. The polymerizable liquid crystal composition of an embodiment of the present invention contains a polymerizable liquid crystal compound having reverse-wavelength dispersion properties and an aromatic polyether-based compound.

11 Claims, 1 Drawing Sheet

(51) Int. Cl.
  *G02B 5/30* (2006.01)
  *H01L 27/32* (2006.01)
  *H01L 51/52* (2006.01)
  *G02F 1/13363* (2006.01)
  *G09F 9/30* (2006.01)
  *C07D 277/82* (2006.01)
  *C08F 20/38* (2006.01)
  *C07D 317/54* (2006.01)
  *H01L 51/50* (2006.01)
  *C08F 2/44* (2006.01)
  *H05B 33/02* (2006.01)
  *C07D 339/06* (2006.01)
  *C07D 417/04* (2006.01)
  *G02F 1/1335* (2006.01)
  *C07D 311/72* (2006.01)
  *C09K 19/04* (2006.01)

(52) U.S. Cl.
  CPC ......... *C07D 317/54* (2013.01); *C07D 339/06* (2013.01); *C07D 417/04* (2013.01); *C08F 2/44* (2013.01); *C08F 20/38* (2013.01); *C09K 19/38* (2013.01); *C09K 19/54* (2013.01); *G02B 5/30* (2013.01); *G02B 5/3016* (2013.01); *G02F 1/1335* (2013.01); *G02F 1/13363* (2013.01); *G09F 9/30* (2013.01); *H01L 27/32* (2013.01); *H01L 51/50* (2013.01); *H01L 51/5293* (2013.01); *H05B 33/02* (2013.01); *C09K 2019/0448* (2013.01)

(56) References Cited

U.S. PATENT DOCUMENTS

2016/0083330 A1* 3/2016 Furusato .............. C09K 19/542
  252/299.4
2016/0137921 A1* 5/2016 Hayashi ............. C09K 19/3861
  252/299.62
2018/0016502 A1 1/2018 Endo et al.
2018/0066189 A1 3/2018 Ishii et al.

FOREIGN PATENT DOCUMENTS

| | | | |
|---|---|---|---|
| JP | 2006-267630 A | | 10/2006 |
| JP | 2007-031709 A | | 2/2007 |
| JP | 2007031709 A | * | 2/2007 |
| JP | 2008-233814 A | | 10/2008 |
| JP | 2008-256749 A | | 10/2008 |
| JP | 2008-273925 A | | 11/2008 |
| JP | 2010-031223 A | | 2/2010 |
| JP | 2010031223 A | * | 2/2010 |
| JP | 2014-162853 A | | 9/2014 |
| JP | 2016-081035 A | | 5/2016 |
| JP | 2016-113583 A | | 6/2016 |
| WO | 2014-010325 A1 | | 1/2014 |
| WO | 2014-069515 A1 | | 5/2014 |
| WO | 2016/114347 A1 | | 7/2016 |
| WO | 2016-114346 A1 | | 4/2017 |

OTHER PUBLICATIONS

Written Opinion Issued in PCT/JP2017/042411 dated Dec. 26, 2017.
International Preliminary Report on Patentability Issued in PCT/JP2017/042411 dated Jun. 4, 2019.
Office Action, issued by the Japanese Patent Office dated Mar. 17, 2020, in connection with corresponding Japanese Patent Application No. 2018-553835.
Office Action, issued by the Korean Intellectual Property Office dated Jul. 15, 2020, in connection with corresponding Korean Patent Application No. 10-2019-7015204.
Office Action, issued by the State Intellectual Property Office dated Nov. 4, 2020, in connection with corresponding Korean Patent Application No. 201780074658.9.

\* cited by examiner

US 11,279,880 B2

POLYMERIZABLE LIQUID CRYSTAL COMPOSITION, OPTICALLY ANISOTROPIC FILM, OPTICAL FILM, POLARIZING PLATE, IMAGE DISPLAY DEVICE, AND ORGANIC ELECTROLUMINESCENT DISPLAY DEVICE

CROSS-REFERENCE TO RELATED APPLICATIONS

This application is a Continuation of PCT International Application No. PCT/JP2017/042411 filed on Nov. 27, 2017, which was published under PCT Article 21(2) in Japanese, and which claims priority under 35 U.S.C. § 119(a) to Japanese Patent Application No. 2016-231479 filed on Nov. 29, 2016. The above applications are hereby expressly incorporated by reference, in their entirety, into the present application.

BACKGROUND OF THE INVENTION

1. Field of the Invention

The present invention relates to a polymerizable liquid crystal composition, an optically anisotropic film, an optical film, a polarizing plate, an image display device, and an organic electroluminescent display device.

2. Description of the Related Art

A polymerizable compound exhibiting reverse-wavelength dispersion properties enables, for example, conversion of an accurate light ray wavelength over a wide wavelength range and reduction in the thickness of a retardation film due to a high refractive index, and therefore, the polymerizable compound has been actively studied.

Furthermore, for the polymerizable compound exhibiting reverse-wavelength dispersion properties, T-type molecular design guidelines have been generally taken, and it has been required to decrease the wavelength of a long molecular axis and increase the wavelength of a short axis positioned in the center of the molecule.

In this regard, it is known that a cycloalkylene skeleton having no absorption wavelength is used for the connection between a skeleton of the short axis positioned in the center of the molecule (hereinafter also referred to as a "reverse-wavelength dispersion expressing portion") and the long molecular axis (see, for example, JP2008-273925A, JP2010-031223A, WO2014/010325A, JP2016-081035A, and WO2016/114346A).

SUMMARY OF THE INVENTION

The present inventors have studied a polymerizable liquid crystal composition containing the polymerizable compound described in JP2008-273925A, JP2010-031223A, WO2014/010325A, JP2016-081035A, and WO2016/114346A, and have thus found that the light fastness of an optically anisotropic film thus formed is deteriorated, depending on the type of the polymerizable compound and the blending conditions of additives.

Therefore, the present invention has an object to provide a polymerizable liquid crystal composition capable of manufacturing an optically anisotropic film having excellent light fastness; and an optically anisotropic film, an optical film, a polarizing plate, an image display device, and an organic electroluminescent display device, each of which uses the polymerizable liquid crystal composition.

The present inventors have conducted extensive studies on the object, and as a result, they have found that the light fastness of an optically anisotropic film thus formed is improved by using a polymerizable liquid crystal compound exhibiting reverse-wavelength dispersion properties in combination with an aromatic polyether-based compound, thereby completing the present invention.

That is, the present inventors have found that the object can be accomplished by the following configurations.

[1] A polymerizable liquid crystal composition comprising:
a polymerizable liquid crystal compound having reverse-wavelength dispersion properties; and
an aromatic polyether-based compound.

[2] The polymerizable liquid crystal composition as described in [1],
in which the aromatic polyether-based compound includes at least one compound selected from the group consisting of Formula (A) which will be described later and Formula (B) which will be described later,
in Formula (A) which will be described later, $R^{1A}$ and $R^{2A}$ each independently represent a monovalent organic group, $R^{3A}$, $R^{4A}$, $R^{5A}$, and $R^{6A}$ each independently represent a hydrogen atom or a monovalent substituent, and $R^{1A}$ and $R^{2A}$, $R^{2A}$ and $R^{3A}$, $R^{3A}$ and $R^{4A}$, $R^{4A}$ and $R^{5A}$, $R^{5A}$ and $R^{6A}$, or $R^{6A}$ and $R^{1A}$ may be bonded to each other to form a ring, and
in Formula (B) which will be described later, $R^{1B}$ and $R^{4B}$ each independently represent a monovalent organic group, $R^{2B}$, $R^{3B}$, $R^{5B}$, and $R^{6B}$ each independently represent a hydrogen atom or a monovalent substituent, and $R^{1B}$ and $R^{2B}$, $R^{2B}$ and $R^{3B}$, $R^{3B}$ and $R^{4B}$, $R^{4B}$ and $R^{5B}$, $R^{5B}$ and $R^{6B}$, or $R^{6B}$ and $R^{1B}$ may be bonded to each other to form a ring.

[3] The polymerizable liquid crystal composition as described in [2],
in which the compound represented by Formula (A) which will be described later is a compound represented by Formula (C) which will be described later or Formula (D) which will be described later,
in Formula (C) which will be described later, $R^{1C}$, $R^{2C}$, $R^{6C}$, and $R^{7C}$ each independently represent a monovalent organic group, $R^{3C}$, $R^{5C}$, $R^{8C}$ and $R^{11C}$ each independently represent a hydrogen atom or a monovalent substituent, and $R^{4C}$, $R^{9C}$, and $R^{10C}$ each independently represent a hydrogen atom or a monovalent organic group, and
in Formula (D) which will be described later, $R^{1D}$ represents an alkylene group having 1 to 3 carbon atoms, $R^{2D}$, $R^{3D}$, $R^{4D}$, and $R^{5D}$ each independently represent a hydrogen atom or a monovalent substituent, and $R^{2D}$ and $R^{3D}$, or $R^{3D}$ and $R^{4D}$ may be bonded to each other to form a ring.

[4] The polymerizable liquid crystal composition as described in [2] or [3],
in which the compound represented by Formula (B) which will be described later is a compound represented by Formula (E) which will be described later or Formula (F) which will be described later,
in Formula (E) which will be described later, $R^{1E}$, $R^{2E}$, $R^{3E}$, $R^{4E}$, $R^{5E}$, and $R^{6E}$ each independently represent a hydrogen atom or a monovalent organic group, $R^{7E}$, $R^{9E}$, and $R^{10E}$ each independently represent a hydrogen atom or a monovalent substituent, $R^{8E}$ represents a monovalent organic group, and $R^{1E}$ and $R^{2E}$, or $R^{3E}$ and $R^{4E}$ may be bonded to each other to form a ring, and
in Formula (F) which will be described later, $R^{1F}$ and $R^{4F}$ each independently represent a monovalent organic group, and $R^{2F}$, $R^{3F}$, $R^{5F}$, and $R^{6F}$ each independently represent a hydrogen atom or a monovalent substituent.

[5] The polymerizable liquid crystal composition as described in any one of [1] to [4], in which the polymerizable liquid crystal compound which will be described later is a liquid crystal compound represented by Formula (I),

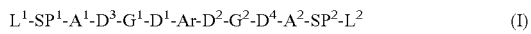

$$L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2 \qquad (I)$$

in Formula (I), $D^1$, $D^2$, $D^3$, and $D^4$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $G^1$ and $G^2$ each independently represent a divalent alicyclic hydrocarbon group having 5 to 8 carbon atoms, and one or more of —$CH_2$—'s constituting the alicyclic hydrocarbon group may be substituted with —O—, —S—, or —NH—, $A^1$ and $A^2$ each independently represent an aromatic ring having 6 or more carbon atoms or a cycloalkylene ring having 6 or more carbon atoms, $SP^1$ and $SP^2$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent, $L^1$ and $L^2$ each independently represent a monovalent organic group, and at least one of $L^1$ or $L^2$ represents a polymerizable group, provided that in a case where Ar is an aromatic ring represented by Formula (Ar-3), at least one of $L^1$, $L^2$, or $L^3$ or $L^4$ in Formula (Ar-3) represents a polymerizable group, Ar represents any one aromatic ring selected from the group consisting of groups represented by Formulae (Ar-1) to (Ar-5) which will be described later, here, in Formulae (Ar-1) to (Ar-5) which will be described later, *1 represents a bonding position with $D^1$ and *2 represents a bonding position with $D^2$, $Q^1$ represents N or CH, $Q^2$ represents —S—, —O—, or —N($R^5$)—, and $R^5$ represents a hydrogen atom or an alkyl group having 1 to 6 carbon atoms, $Y^1$ represents an aromatic hydrocarbon group having 6 to 12 carbon atoms or aromatic heterocyclic group having 3 to 12 carbon atoms, which may have a substituent, $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$NR^6R^7$, or —$SR^8$, $R^6$ to $R^8$ each independently represent a hydrogen atom or an alkyl group having 1 to 6 carbon atoms, and $Z^1$ and $Z^2$ may be bonded to each other to form an aromatic ring, $A^3$ and $A^4$ each independently represent a group selected from the group consisting of —O—, —N($R^9$)—, —S—, and —CO—, and $R^9$ represents a hydrogen atom or a substituent, X represents a hydrogen atom or a non-metal atom of Groups 14 to 16 to which a substituent may be bonded, $D^5$ and $D^6$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $SP^3$ and $SP^4$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent, $L^3$ and $L^4$ each independently represent a monovalent organic group, and at least one of $L^3$, $L^4$, or $L^1$ or $L^2$ in Formula (I) represents a polymerizable group, Ax represents an organic group having 2 to 30 carbon atoms, which has at least one aromatic ring selected from the group consisting of an aromatic hydrocarbon ring and an aromatic heterocyclic ring, Ay represents a hydrogen atom, an alkyl group having 1 to 6 carbon atoms which may have a substituent, or an organic group having 2 to 30 carbon atoms, which has at least one aromatic ring selected from the group consisting of an aromatic hydrocarbon ring and an aromatic heterocyclic ring, the aromatic rings in Ax and Ay may have a substituent, and Ax and Ay may be bonded to each other to form a ring, and $Q^3$ represents a hydrogen atom or an alkyl group having 1 to 6 carbon atoms which may have a substituent.

[6] The polymerizable liquid crystal composition as described in [5], in which a pKa of a compound used for the formation of Ar in Formula (I) is 5.8 to 10.0.

[7] The polymerizable liquid crystal composition as described in any one of [1] to [6], in which a content of the aromatic polyether-based compound is 0.1 to 50 parts by mass with respect to 100 parts by mass of the polymerizable liquid crystal compound.

[8] An optically anisotropic film obtained by polymerization of the polymerizable liquid crystal composition as described in any one of [1] to [7],

[9] An optical film comprising the optically anisotropic film as described in [8],

[10] The optical film as described in [9], in which the optically anisotropic film is a positive A plate or a positive C plate.

[11] The optical film as described in [9] or [10], comprising two or more layers of the optically anisotropic films, in which at least one of the layers is a positive A plate and at least one of the other layers is a positive C plate.

[12] A polarizing plate comprising:
the optical film as described in any one of [9] to [11]; and
a polarizer.

[13] An image display device comprising the optical film as described in any one of [9] to [11] or the polarizing plate as described in [12],

[14] An organic electroluminescent display device comprising:
an organic electroluminescent display panel; and
a circularly polarizing plate arranged on the organic electroluminescent display panel,
in which the circularly polarizing plate includes a polarizer and the optical film as described in [11], According to the present invention, it is possible to provide a polymerizable liquid crystal composition capable of manufacturing an optically anisotropic film having excellent light fastness; and an optically anisotropic film, an optical film, a polarizing plate, an image display device, and an organic electroluminescent display device, each of which uses the polymerizable liquid crystal composition.

DESCRIPTION OF THE PREFERRED EMBODIMENTS

Figure 1A:
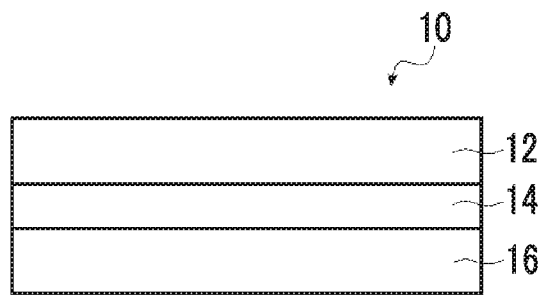
FIG. 1A is a schematic cross-sectional view showing an example of an optical film of an embodiment of the present invention.

Hereinafter, the present invention will be described in detail.

The following description of the constitutional requirements is made based on representative embodiments of the present invention in some cases, but it should not be construed that the present invention is limited to such embodiments.

Furthermore, in the present specification, a numerical range expressed using "to" means a range that includes the preceding and succeeding numerical values of "to" as the lower limit value and the upper limit value, respectively.

In the present specification, the bonding direction of a divalent group (for example, —CO—O—) expressed is not particularly limited, and for example, in a case where $D^1$ in Formula (I) which will be described later is —CO—O—, $D^1$ may be either *1-CO—O—*2 or *1-O—CO—*2, in which *1 represents a position bonding to the Ar side and *2 represents a position bonding to the $G^1$ side.

[Polymerizable Liquid Crystal Composition]

A polymerizable liquid crystal composition of an embodiment of the present invention contains a polymerizable liquid crystal compound having reverse-wavelength dispersion properties (hereinafter simply referred to as "reverse dispersion" in some cases) and an aromatic polyether-based compound.

Using the polymerizable liquid crystal composition of the embodiment of the present invention, an optically anisotropic film having excellent light fastness can be manufactured. Details of a reason therefor are still not clear, but are presumed to be as follows.

In a case where the optical film is irradiated with light in the presence of oxygen, electrons are generated from the aromatic polyether-based compound. Here, an energy level of the highest occupied molecular orbital (HOMO) of the aromatic polyether-based compound is higher than the energy level of the HOMO of the polymerizable liquid crystal compound. Thus, it is presumed that the electrons generated from the aromatic polyether-based compound replace the electrons generated from the polymerizable liquid crystal compound, and they move to the lowest unoccupied molecular orbital (LUMO) of singlet oxygen. As a result, it is presumed that the decomposition of the polymerizable liquid crystal compound is suppressed, and thus, the light fastness of the optically anisotropic film is improved.

Particularly, such the effect is more remarkably exerted by using a compound having a low pKa (preferably a pKa of 10 or more) as a compound (for example, a compound used for formation of Ar in Formula (I)) used for the formation of a core portion of the polymerizable liquid crystal compound. That is, due to a lower pKa of the compound used for the formation of a core portion of the polymerizable liquid crystal compound, the HOMO of the polymerizable liquid crystal compound is lowered. As a result, an energy difference between the singlet oxygen and the LUMO is generated, and thus, the polymerizable liquid crystal compound itself is light-fastened.

[Polymerizable Liquid Crystal Compound]

The polymerizable liquid crystal composition of the embodiment of the present invention contains a polymerizable liquid crystal compound having reverse-wavelength dispersion properties.

Here, in the present specification, the polymerizable liquid crystal compound having "reverse-wavelength dispersion properties" indicates that an in-plane retardation (Re) value becomes equal to or higher with an increase in a measurement wavelength in a case where the in-plane Re value at a specific wavelength (visible light range) of a retardation film manufactured using the polymerizable liquid crystal compound is measured.

Furthermore, in the present specification, the "polymerizable liquid crystal compound" refers to a liquid crystal compound having a polymerizable group. The type of polymerizable group contained in the polymerizable liquid crystal compound is not particularly limited, and examples thereof include an acryloyl group, a methacryloyl group, a vinyl group, a styryl group, and an allyl group.

The type of the polymerizable liquid crystal compound is not particularly limited, but can be classified into a rod-like type (rod-like liquid crystal compound) and a disk-like type (disk-like liquid crystal compound). Further, the polymerizable liquid crystal compound encompasses a low molecular type and a high molecular type. The term "high molecular" generally refers to a compound having a degree of polymerization of 100 or more (Polymer Physics-Phase Transition Dynamics, by Masao Doi, page. 2, published by Iwanami Shoten, Publishers, 1992). In the present invention, any type of liquid crystal compounds can be used. Two or more kinds of rod-like liquid crystal compounds, two or more kinds of disk-like liquid crystal compounds, or a mixture of the rod-like liquid crystal compound and the disk-like liquid crystal compound may be used.

Among those, the rod-like liquid crystal compound is preferably used since it becomes easy to make a retardation film thus formed function as a positive A plate by homogeneously (horizontally) aligning the rod-like liquid crystal compound.

The polymerizable liquid crystal compound is not particularly limited as long as it can form a film having reverse-wavelength dispersion properties as described above, and for example, the compound represented by General Formula (I) described in JP2008-297210A (in particular, the compound described in paragraph Nos. [0034] to [0039]), the compound represented by General Formula (1) described in JP2010-084032A (in particular, the compound described in paragraph Nos. [0067] to [0073]), a liquid crystal compound represented by Formula (I) which will be described later, or the like can be used.

In the present invention, from the viewpoint that the polymerizable liquid crystal compound has more excellent reverse-wavelength dispersion properties, it is preferable that the polymerizable liquid crystal compound is a liquid crystal compound represented by Formula (I).

$$L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2 \quad (I)$$

In Formula (I), $D^1$, $D^2$, $D^3$, and $D^4$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^2$—, —O—CO—$CR^1R^2$—, —$CR^1R^2$—O—CO—$CR^3R^4$—, —$CR*R^2$—CO—O—$CR^3R^4$—, —$NR^1$—$CR^2R^3$—, or —CO—$NR^1$—. $R^1$, $R^2$, $R^3$, and $R^4$ each independently represent a hydrogen atom, a fluorine atom, or an alkyl group having 1 to 4 carbon atoms.

Incidentally, in Formula (I), $G^1$ and $G^2$ each independently represent a divalent alicyclic hydrocarbon group having 5 to 8 carbon atoms, and one or more of —$CH_2$—'s constituting the alicyclic hydrocarbon group may be substituted with —O—, —S—, or —NH—.

Furthermore, in Formula (I), $A^1$ and $A^2$ each independently represent an aromatic ring having 6 or more carbon atoms, or a cycloalkylene ring having 6 or more carbon atoms.

Moreover, in Formula (I), $SP^1$ and $SP^2$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent.

In addition, in Formula (I), $L^1$ and $L^2$ each independently represent a monovalent organic group, and at least one of $L^1$ or $L^2$ represents a polymerizable group, provided that in a case where Ar is an aromatic ring represented by Formula (Ar-3), at least one of $L^1$, $L^2$, or $L^3$ or $L^4$ in Formula (Ar-3) represents a polymerizable group.

In Formula (I), the divalent alicyclic hydrocarbon group having 5 to 8 carbon atoms represented by each of $G^1$ and $G^2$ is preferably a 5- or 6-membered ring. Further, the alicyclic hydrocarbon group may be saturated or unsaturated, but is preferably a saturated alicyclic hydrocarbon group. With respect to the divalent alicyclic hydrocarbon group represented by each of $G^1$ and $G^2$, reference can be made to, for example, the description in paragraph 0078 of JP2012-021068A, the contents of which are incorporated herein by reference.

In Formula (I), examples of the aromatic ring having 6 or more carbon atoms represented by each of $A^1$ and $A^2$ include aromatic hydrocarbon rings such as a benzene ring, a naphthalene ring, an anthracene ring, and a phenanthroline ring; and aromatic heterocyclic rings such as a furan ring, a pyrrole ring, a thiophene ring, a pyridine ring, a thiazole ring, and a benzothiazole ring. Among those, the benzene ring (for example, a 1,4-phenyl group) is preferable.

In addition, in Formula (I), examples of the cycloalkylene ring having 6 or more carbon atoms represented by each of $A^1$ and $A^2$ include a cyclohexane ring and a cyclohexene ring. Among those, the cyclohexane ring (for example, a cyclohexane-1,4-diyl group) is preferable.

in Formula (I), suitable examples of the linear or branched alkylene group having 1 to 12 carbon atoms represented by each of $SP^1$ and $SP^2$ include a methylene group, an ethylene group, a propylene group, and a butylene group.

In Formula (I), the polymerizable group represented by at least one of $L^1$ or $L^2$ is not particularly limited, but is preferably a polymerizable group capable of radical polymerization or cationic polymerization.

A generally known radically polymerizable group can be used as the radically polymerizable group, and suitable examples thereof include an acryloyl group and a methacryloyl group. In this case, it is generally known that the acryloyl group exhibits a fast polymerization rate, and thus, the acryloyl group is preferable from the viewpoint of improvement of productivity, but the methacryloyl group can also be used as the polymerizable group of a highly birefringent liquid crystal.

A generally known cationically polymerizable group can be used as the cationically polymerizable group, and specific examples thereof include an alicyclic ether group, a cyclic acetal group, a cyclic lactone group, a cyclic thioether group, a spiroorthoester group, and a vinyloxy group. Among those, the alicyclic ether group or the vinyloxy group is preferable, and the epoxy group, the oxetanyl group, or the vinyloxy group is particularly preferable.

Particularly preferred examples of the polymerizable groups include the following ones.

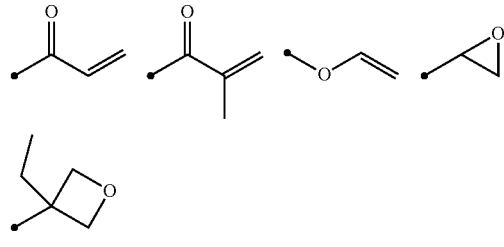

On the other hand, in Formula (I), Ar represents any one aromatic ring selected from the group consisting of groups represented by Formulae (Ar-1) to (Ar-5). Further, in Formulae (Ar-1) to (Ar-5), *1 represents a bonding position with $D^1$ and *2 represents a bonding position with $D^2$.

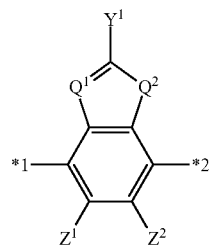

(Ar-1)

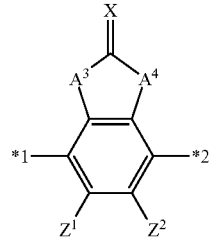

(Ar-2)

-continued

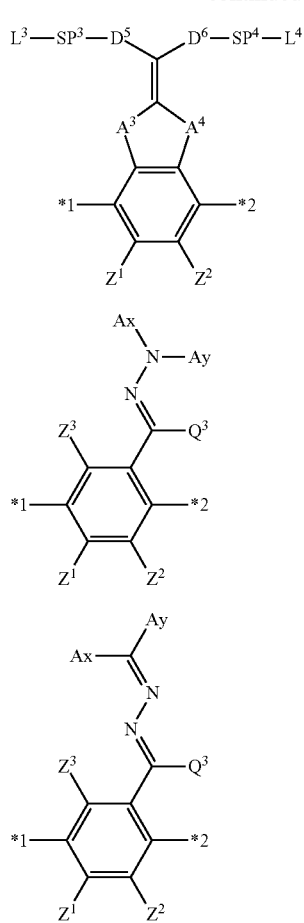

(Ar-3)

(Ar-4)

(Ar-5)

Here, in Formulae (Ar-1), $Q^1$ represents N or CH, $Q^2$ represents —S—, —O—, or —N($R^5$)—, $R^5$ represents a hydrogen atom or an alkyl group having 1 to 6 carbon atoms, and $Y^1$ represents an aromatic hydrocarbon group having 6 to 12 carbon atoms or an aromatic heterocyclic group having 3 to 12 carbon atoms, each of which may have a substituent.

Specific examples of the alkyl group having 1 to 6 carbon atoms represented by $R^5$ include a methyl group, an ethyl group, a propyl group, an isopropyl group, an n-butyl group, an isobutyl group, a sec-butyl group, a tert-butyl group, an n-pentyl group, and an n-hexyl group.

Examples of the aromatic hydrocarbon group having 6 to 12 carbon atoms represented by $Y^1$ include aryl groups such as a phenyl group, a 2,6-diethylphenyl group, and a naphthyl group.

Examples of the aromatic heterocyclic group having 3 to 12 carbon atoms represented by $Y^1$ include heteroaryl groups such as a thienyl group, a thiazolyl group, a furyl group, and a pyridyl group.

Furthermore, examples of the substituent which may be contained in $Y^1$ include an alkyl group, an alkoxy group, and a halogen atom.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a tert-butyl group, and a cyclohexyl group) is more preferable, an alkyl group having 1 to 4 carbon atoms is still more preferable, and the methyl group or the ethyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, and a methoxy ethoxy group) is more preferable, an alkoxy group having 1 to 4 carbon atoms is still more preferable, and the methoxy group or the ethoxy group is particularly preferable.

Examples of the halogen atom include a fluorine atom, a chlorine atom, a bromine atom, and an iodine atom, and among those, the fluorine atom or the chlorine atom is preferable.

In addition, in Formulae (Ar-1) to (Ar-5), $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$NR^6R^7$, or —$SR^8$, $R^6$ to $R^8$ each independently represent a hydrogen atom or an alkyl group having 1 to 6 carbon atoms, and $Z^1$ and $Z^2$ may be bonded to each other to form an aromatic ring.

As the monovalent aliphatic hydrocarbon group having 1 to 20 carbon atoms, an alkyl group having 1 to 15 carbon atoms is preferable and an alkyl group having 1 to 8 carbon atoms is more preferable. Specifically, a methyl group, an ethyl group, an isopropyl group, a tert-pentyl group (1,1-dimethylpropyl group), a tert-butyl group, or a 1,1-dimethyl-3,3-dimethyl-butyl group is still more preferable, and the methyl group, the ethyl group, or the tert-butyl group is particularly preferable.

Examples of the monovalent alicyclic hydrocarbon group having 3 to 20 carbon atoms include monocyclic saturated hydrocarbon groups such as a cyclopropyl group, a cyclobutyl group, a cyclopentyl group, a cyclohexyl group, a cycloheptyl group, a cyclooctyl group, a cyclodecyl group, a methylcyclohexyl group, and an ethylcyclohexyl group; monocyclic unsaturated hydrocarbon groups such as a cyclobutenyl group, a cyclopentenyl group, a cyclodecenyl group, a cycloheptenyl group, a cyclooctenyl group, a cyclodecenyl group, a cyclopentadienyl group, a cyclohexadienyl group, a cyclooctadienyl group, and cyclodecadiene; and polycyclic saturated hydrocarbon groups such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$]dodecyl group, and an adamantyl group.

Specific examples of the monovalent aromatic hydrocarbon group having 6 to 20 carbon atoms include a phenyl group, a 2,6-diethylphenyl group, a naphthyl group, and a biphenyl group, and an aryl group having 6 to 12 carbon atoms (particularly a phenyl group) is preferable.

Examples of the halogen atom include a fluorine atom, a chlorine atom, a bromine atom, and an iodine atom, and among those, the fluorine atom, the chlorine atom, or the bromine atom is preferable.

On the other hand, specific examples of the alkyl group having 1 to 6 carbon atoms represented by each of $R^6$ and $R^8$ include a methyl group, an ethyl group, a propyl group, an isopropyl group, an n-butyl group, an isobutyl group, a sec-butyl group, a tert-butyl group, and an n-pentyl group and an n-hexyl group.

In addition, in Formulae (Ar-2) and (Ar-3), $A^3$ and $A^4$ each independently represent a group selected from the group consisting of —O—, —N($R^9$)—, —S—, and —CO—, and $R^9$ represents a hydrogen atom or a substituent.

Examples of the substituent represented by $R^9$ include the same substituents which may be contained in $Y^1$ in Formula (Ar-1).

Furthermore, in Formula (Ar-2), X represents a hydrogen atom or a non-metal atom of Groups 14 to 16 to which a substituent may be bonded.

Moreover, examples of the non-metal atom of Groups 14 to 16 represented by X include an oxygen atom, a sulfur atom, a nitrogen atom having a substituent, and a carbon atom having a substituent, and specific examples of the substituent include an alkyl group, an alkoxy group, an alkyl-substituted alkoxy group, a cyclic alkyl group, an aryl group (for example, a phenyl group and a naphthyl group), a cyano group, an amino group, a nitro group, an alkylcarbonyl group, a sulfo group, and a hydroxyl group.

Furthermore, in Formula (Ar-3), $D^5$ and $D^6$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—. $R^1$, $R^2$, $R^3$, and $R^4$ each independently represent a hydrogen atom, a fluorine atom, or an alkyl group having 1 to 4 carbon atoms.

Moreover, in Formula (Ar-3), $SP^3$ and $SP^4$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent. Examples of the substituent include the same ones as those for the substituent which may be contained in $Y^1$ in Formula (Ar-1).

Furthermore, in Formula (Ar-3), $L^3$ and $L^4$ each independently represent a monovalent organic group, and at least one of $L^3$, $L^4$, or $L^1$ or $L^2$ in Formula (I) represents a polymerizable group.

Moreover, in Formulae (Ar-4) to (Ar-5), Ax represents an organic group having 2 to 30 carbon atoms, which has at least one aromatic ring selected from the group consisting of an aromatic hydrocarbon ring and an aromatic heterocyclic ring.

Furthermore, in Formulae (Ar-4) to (Ar-5), Ay represents a hydrogen atom, an alkyl group having 1 to 6 carbon atoms which may have a substituent, or an organic group having 2 to 30 carbon atoms, which has at least one aromatic ring selected from the group consisting of an aromatic hydrocarbon ring and an aromatic heterocyclic ring.

Here, the aromatic rings in Ax and Ay may have a substituent, and Ax and Ay may be bonded to each other to form a ring.

In addition, $Q^3$ represents a hydrogen atom or an alkyl group having 1 to 6 carbon atoms which may have a substituent.

Examples of Ax and Ay include ones described in paragraphs [0039] to [0095] of WO2014/010325A.

Incidentally, specific examples of the alkyl group having 1 to 6 carbon atoms represented by $Q^3$ include a methyl group, an ethyl group, a propyl group, an isopropyl group, an n-butyl group, an isobutyl group, a sec-butyl group, a tert-butyl group, an n-pentyl group, and an n-hexyl group. Examples of the substituent include the same ones as the substituents which may be contained in $Y^1$ in Formula (Ar-1).

Preferred examples of the liquid crystal compound represented by Formula (I) are shown below, but are not limited to these liquid crystal compounds. Further, the 1,4-cyclohexylene groups in the following formulae are all a trans-1,4-cyclohexylene group.

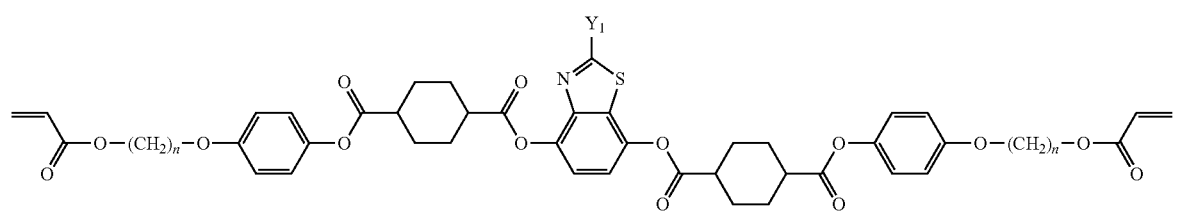

| No | Y1 | n |
|---|---|---|
| II-1-1 | 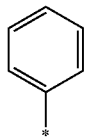 | 6 |
| II-1-2 | 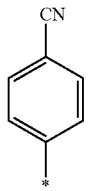 | 6 |

-continued
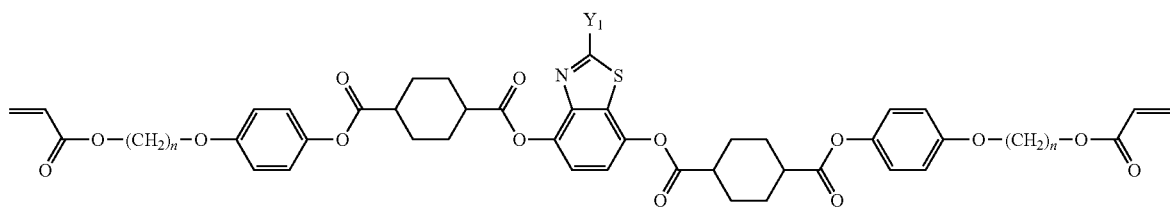
| No | Y1 | n |
|---|---|---|
| II-1-3 | *-C6H4-NO2 (para) | 6 |
| II-1-4 | *-pyridin-4-yl | 6 |
| II-1-5 | *-C6H4-CH=CH-C6H5 | 6 |
| II-1-6 | *-C6H4-NO2 (para) | 11 |
| II-1-7 | *-C6H4-NO2 (para) | 8 |
| II-1-8 | *-C6H4-NO2 (para) | 4 |

-continued
| No | Y1 | n |
|---|---|---|
| II-1-9 | 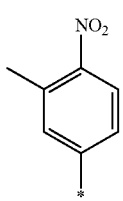 | 6 |
| II-1-10 | 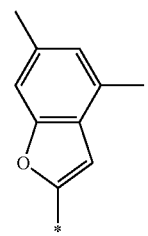 | 6 |
| II-1-11 | 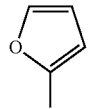 | 6 |
| II-1-12 | 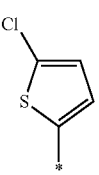 | 6 |
| II-1-13 | 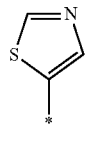 | 6 |
| II-1-14 | 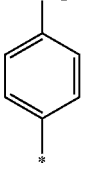 | 6 |
| II-1-15 | | 6 |

II-1-16
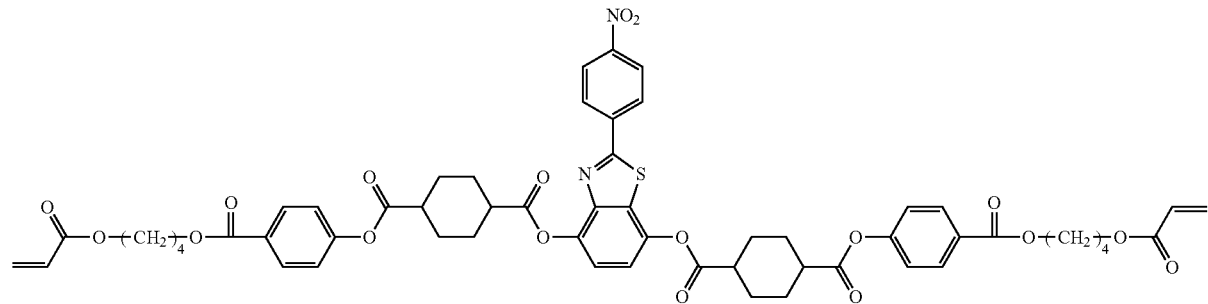
II-1-17
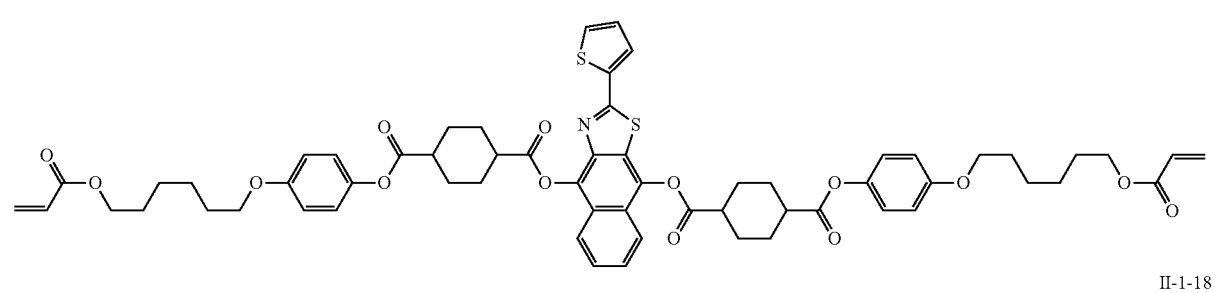
II-1-18
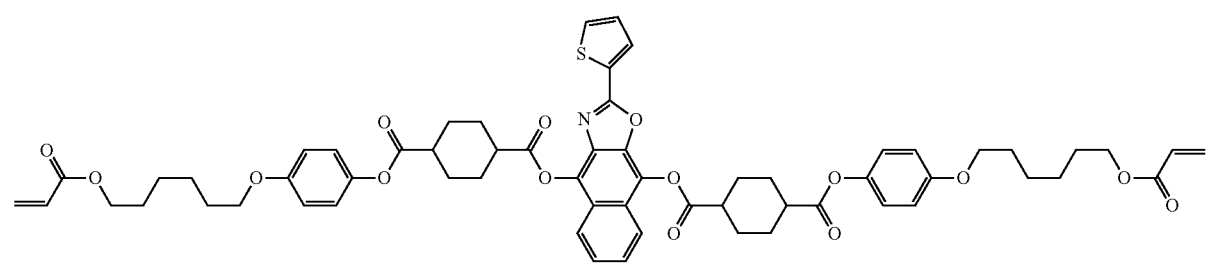

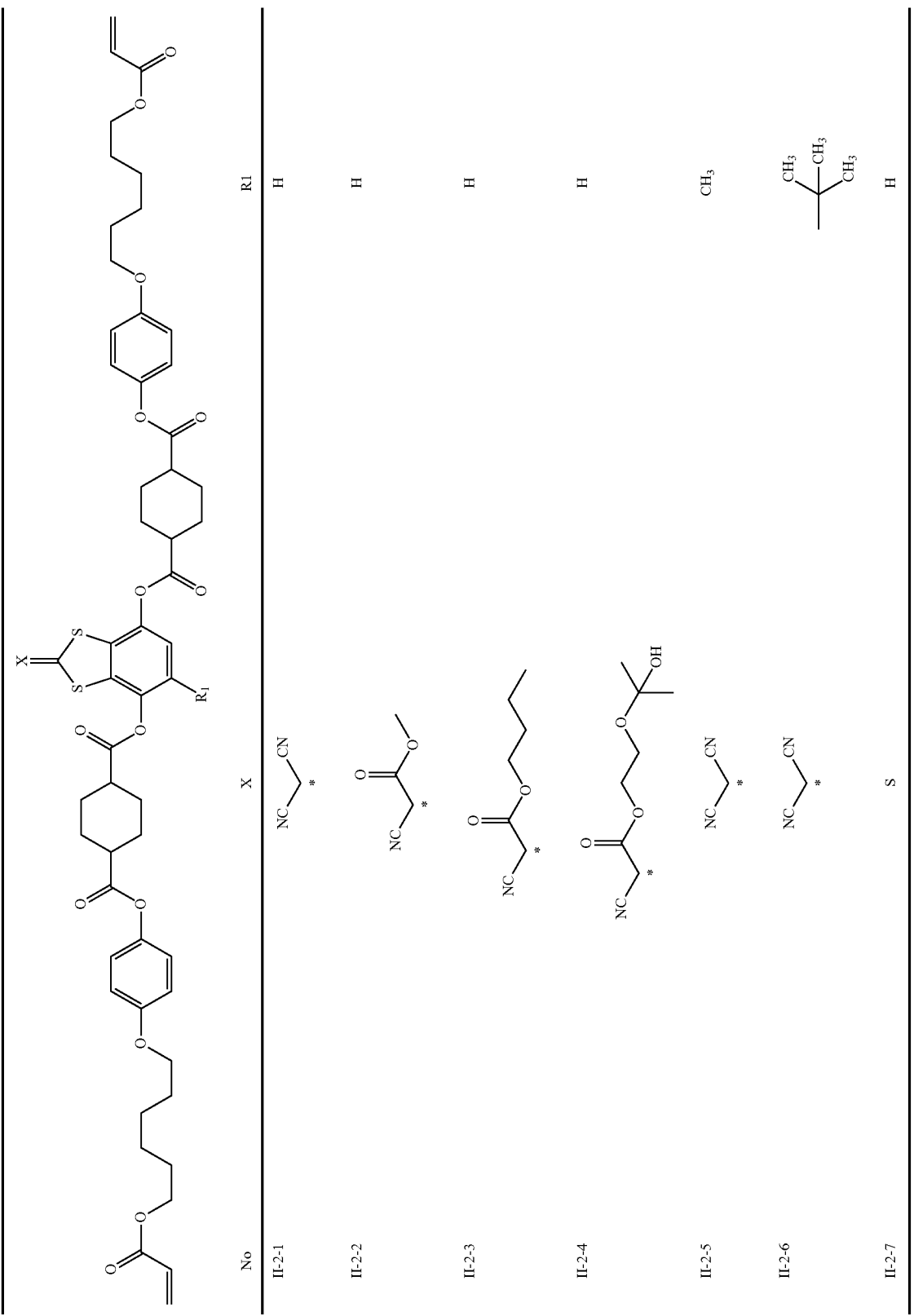

Furthermore, in the formulae, "*" represents a bonding position.
II-2-8
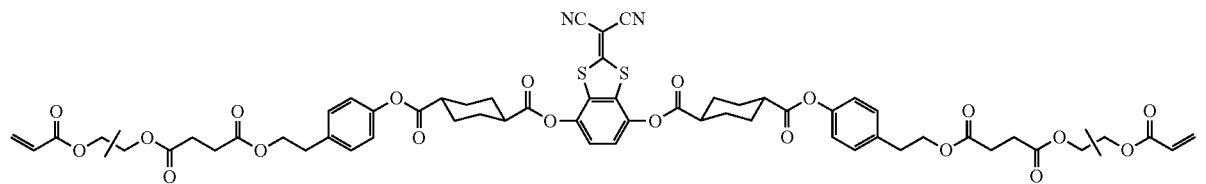
II-2-9
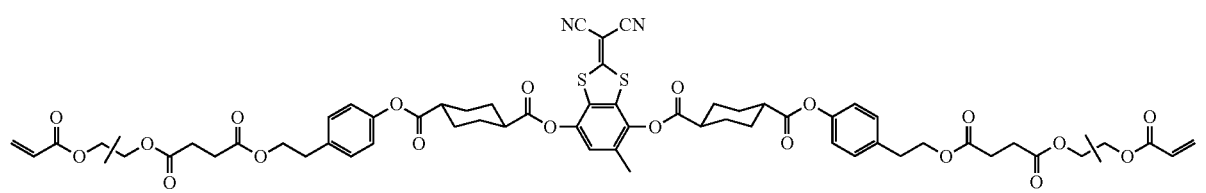
Moreover, a group adjacent to the acryloyloxy group in Formulae II-2-8 and II-2-9 represents a propylene group (a group in which a methyl group is substituted with an ethylene group), and represents a mixture of position isomers having different positions of the methyl groups.

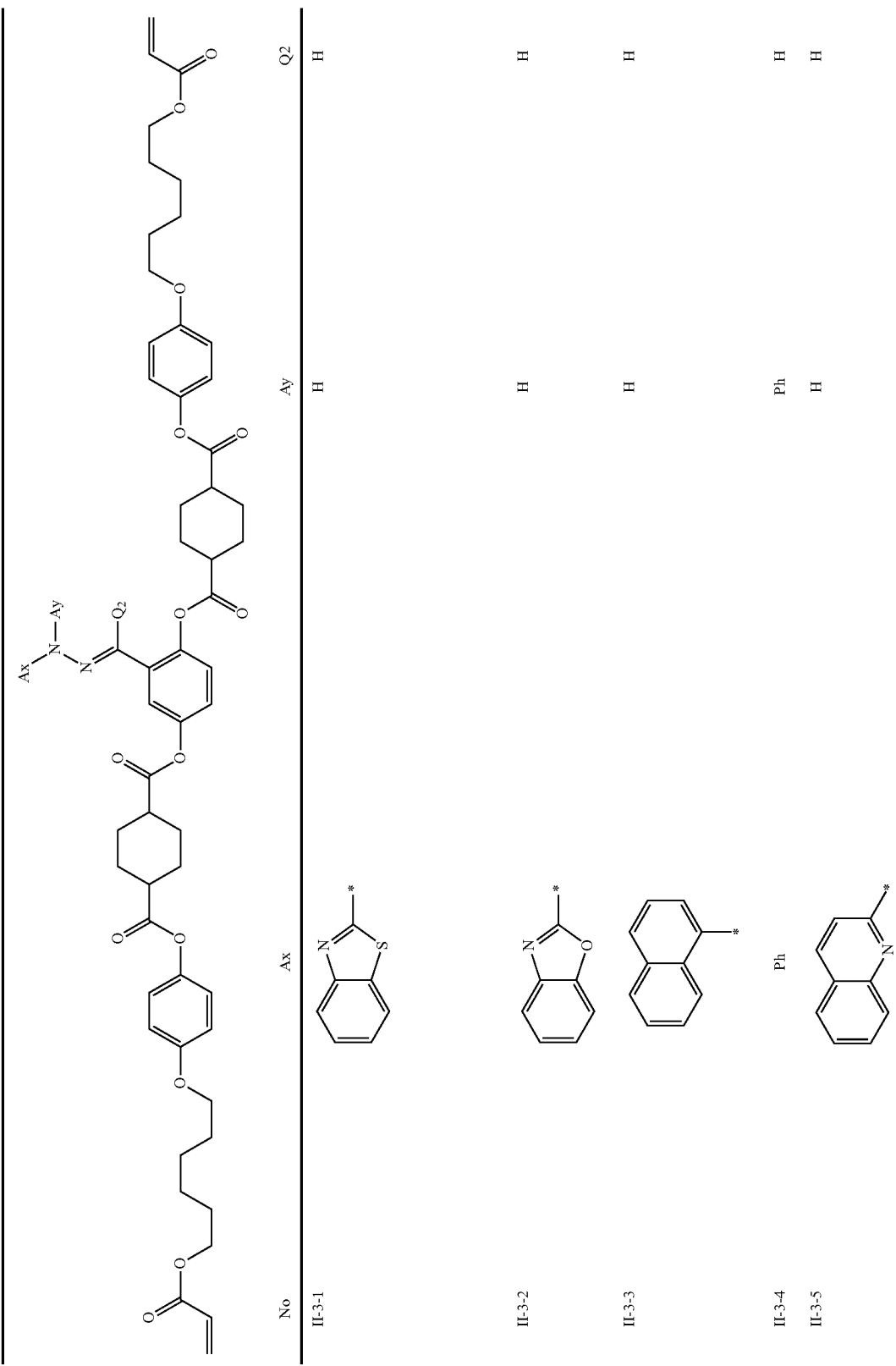

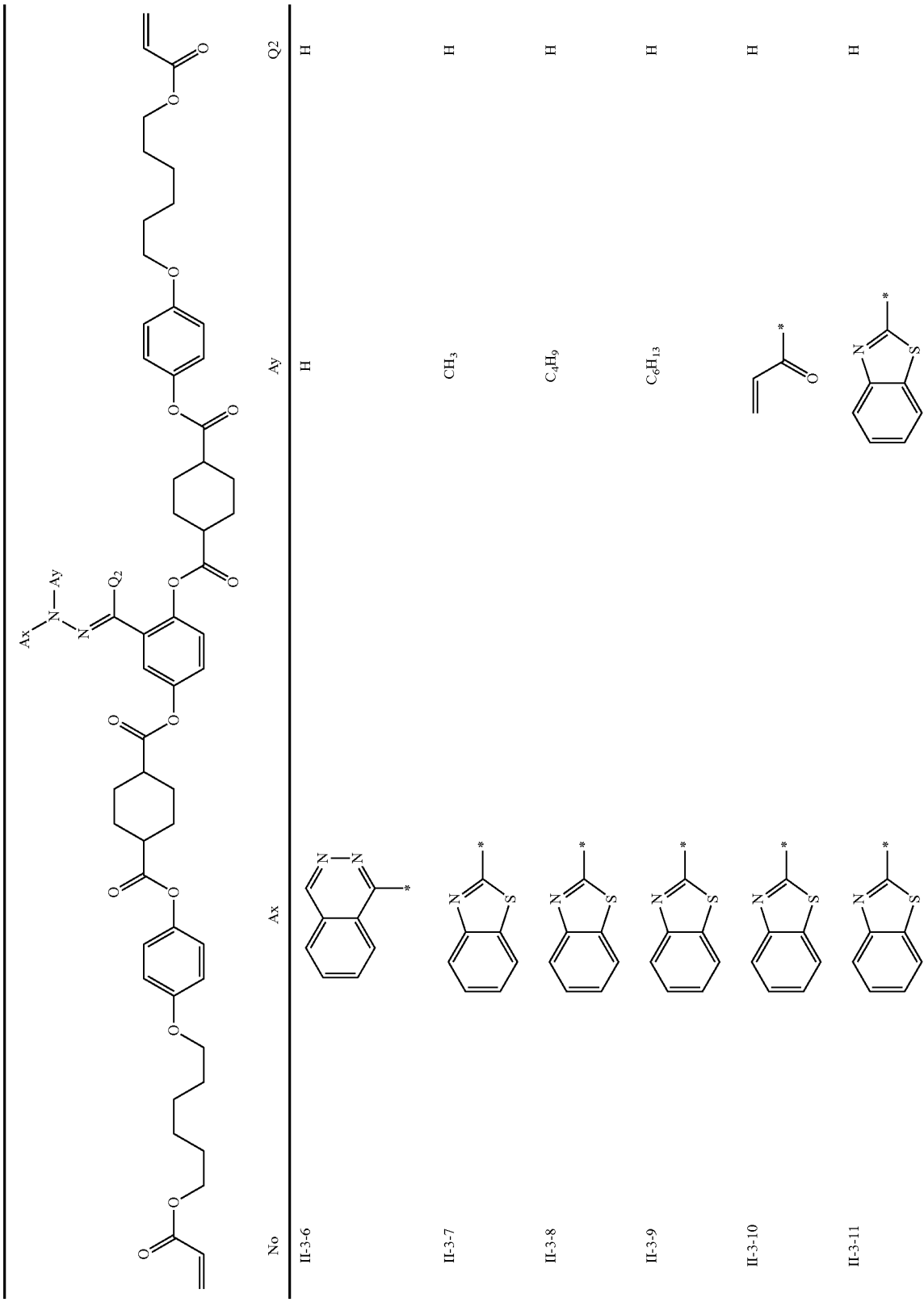

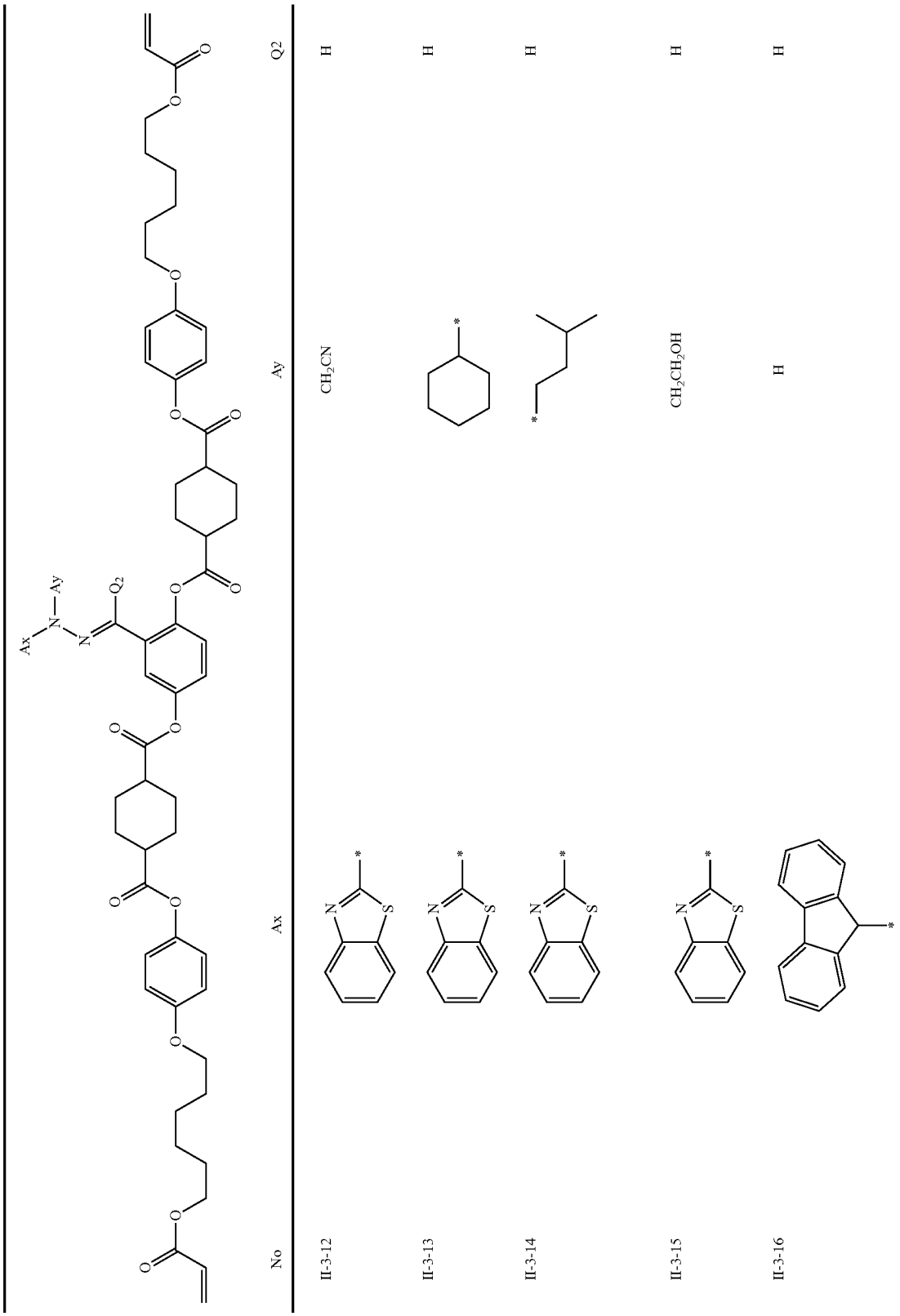

-continued
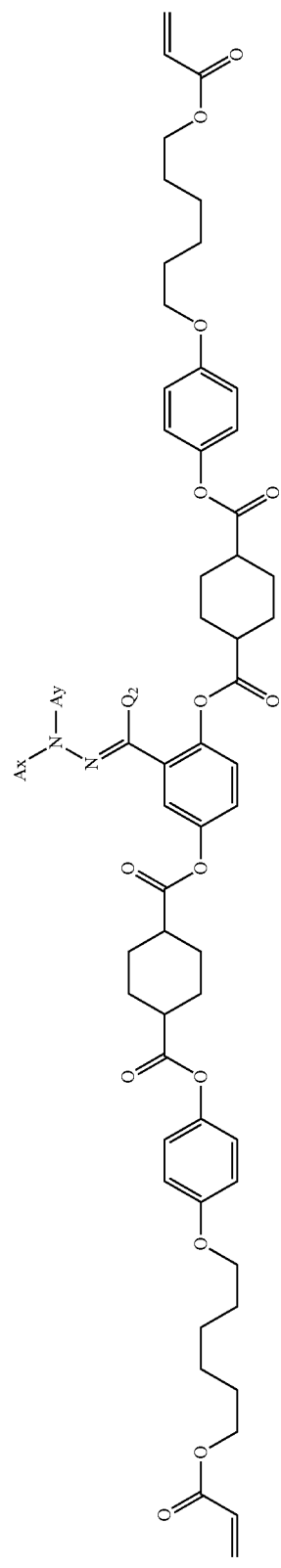
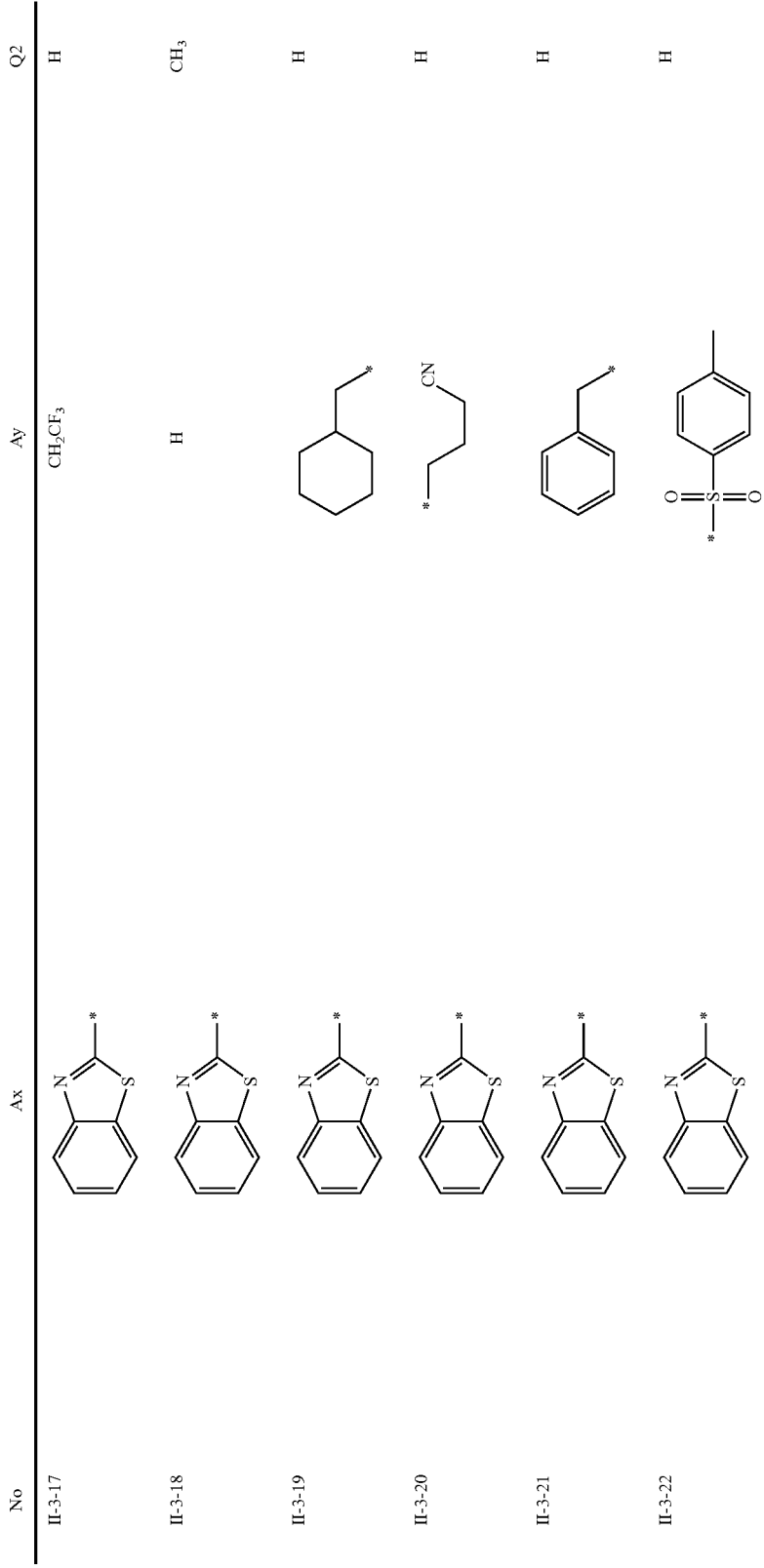
| No | Ax | Ay | Q2 |
|---|---|---|---|
| II-3-17 | benzothiazol-2-yl | CH$_2$CF$_3$ | H |
| II-3-18 | benzothiazol-2-yl | H | CH$_3$ |
| II-3-19 | benzothiazol-2-yl | cyclohexylmethyl | H |
| II-3-20 | benzothiazol-2-yl | 3-cyanopropyl | H |
| II-3-21 | benzothiazol-2-yl | benzyl | H |
| II-3-22 | benzothiazol-2-yl | tosyl | H |

-continued
| No | Ax | Ay | Q2 |
|---|---|---|---|
| II-3-23 | 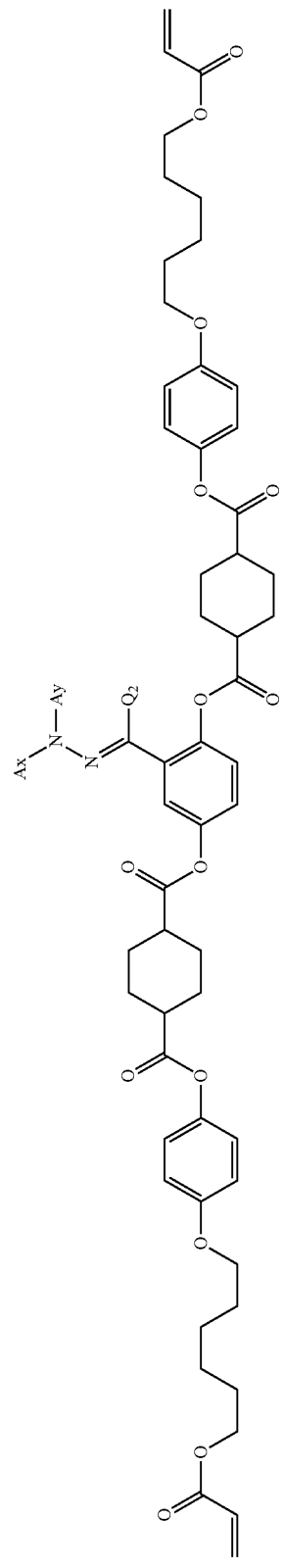 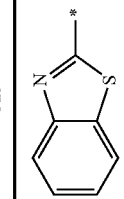 | 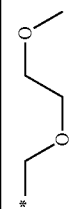 | H |
| II-3-24 | 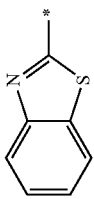 | 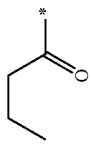 | H |
| II-3-25 | 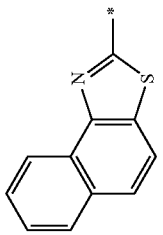 | C$_6$H$_{13}$ | H |

II-3-26
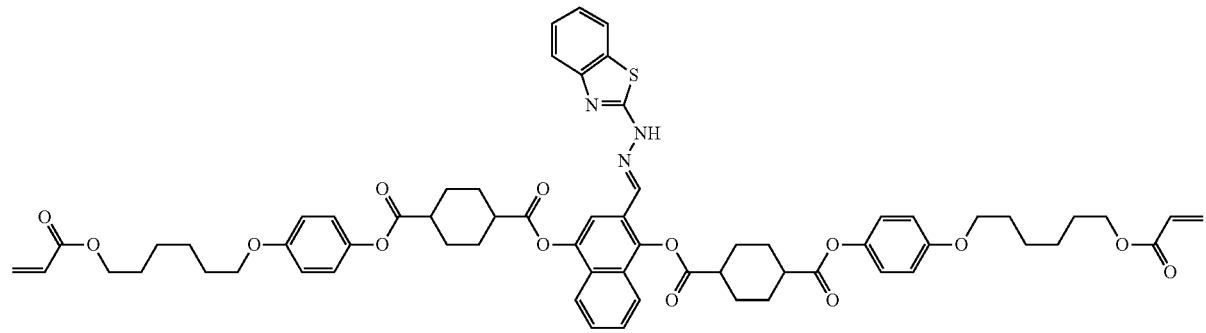
II-3-27
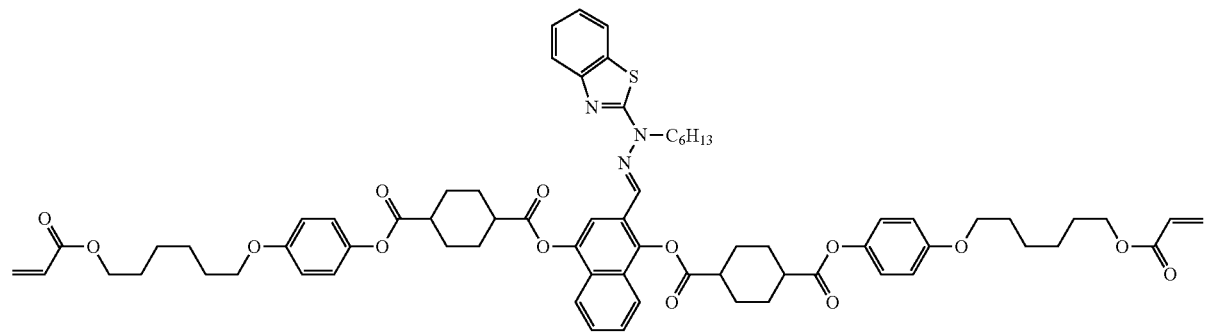
II-3-28
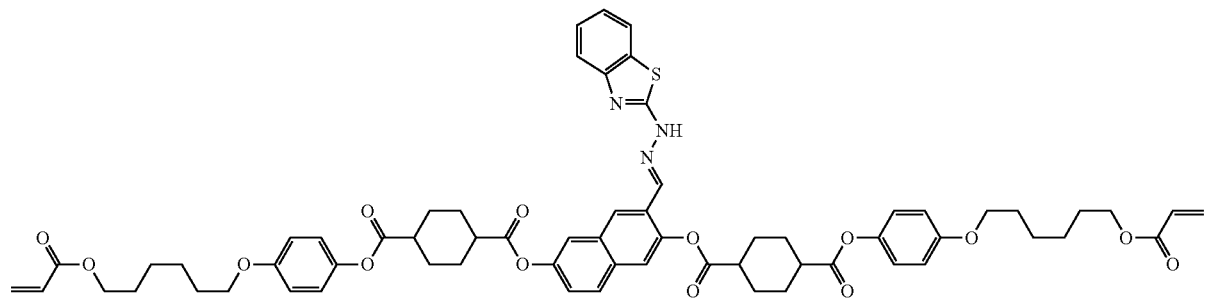
II-3-29
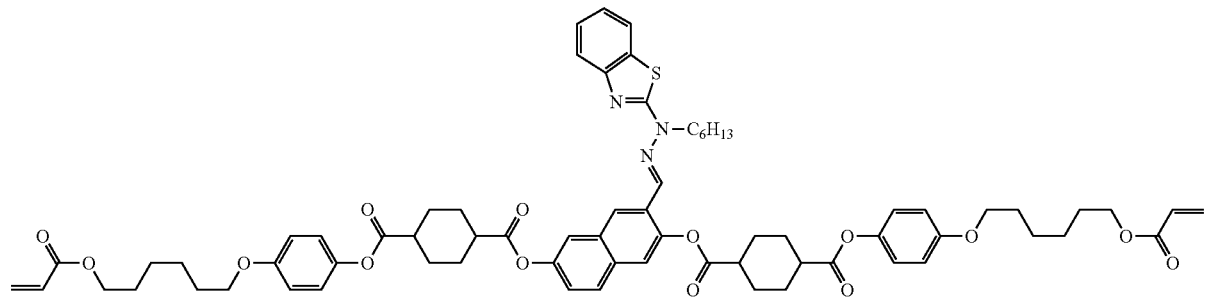

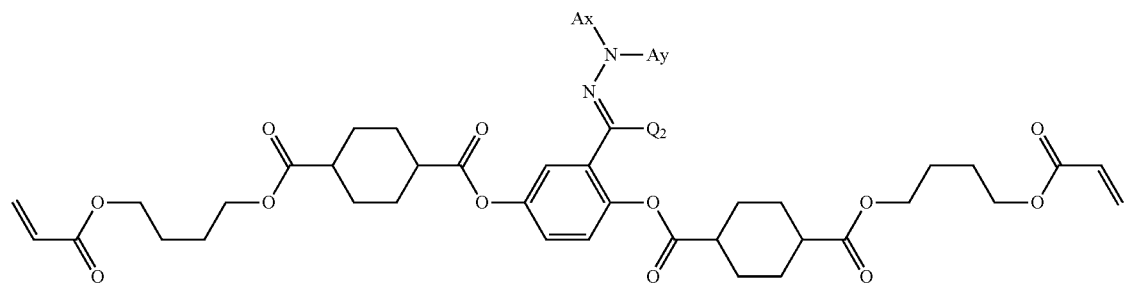
| No | Ax | Ay | Q2 |
|---|---|---|---|
| II-3-30 | benzothiazol-2-yl | H | H |
| II-3-31 | benzoxazol-2-yl | H | H |
| II-3-32 | naphthalen-1-yl | H | H |
| II-3-33 | Ph | Ph | H |
| II-3-34 | quinolin-2-yl | H | H |
| II-3-35 | phthalazin-1-yl | H | H |
| II-3-36 | benzothiazol-2-yl | $CH_3$ | H |
| II-3-37 | benzothiazol-2-yl | $C_4H_9$ | H |
| II-3-38 | benzothiazol-2-yl | $C_6H_{13}$ | H |
| II-3-39 | benzothiazol-2-yl | acryloyl | H |

-continued
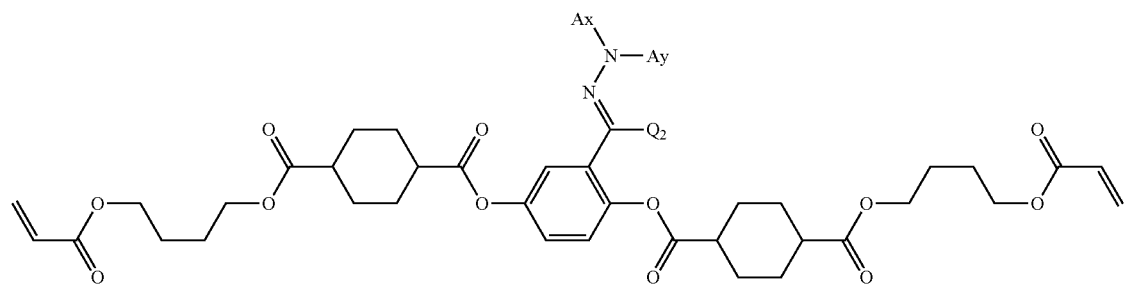
| No | Ax | Ay | Q2 |
|---|---|---|---|
| II-3-40 | benzothiazol-2-yl | benzothiazol-2-yl | H |
| II-3-41 | benzothiazol-2-yl | CH$_2$CN | H |
| II-3-42 | benzothiazol-2-yl | cyclohexyl | H |
| II-3-43 | benzothiazol-2-yl | isobutyl | H |
| II-3-46 | benzothiazol-2-yl | CH$_2$CH$_2$OH | H |
| II-3-45 | fluoren-9-yl | H | H |
| II-3-46 | benzothiazol-2-yl | CH$_2$CF$_3$ | H |
| II-3-47 | benzothiazol-2-yl | H | CH$_3$ |
| II-3-48 | benzothiazol-2-yl | cyclohexylmethyl | H |
| II-3-49 | benzothiazol-2-yl | *-CH$_2$CH$_2$CN | H |

-continued
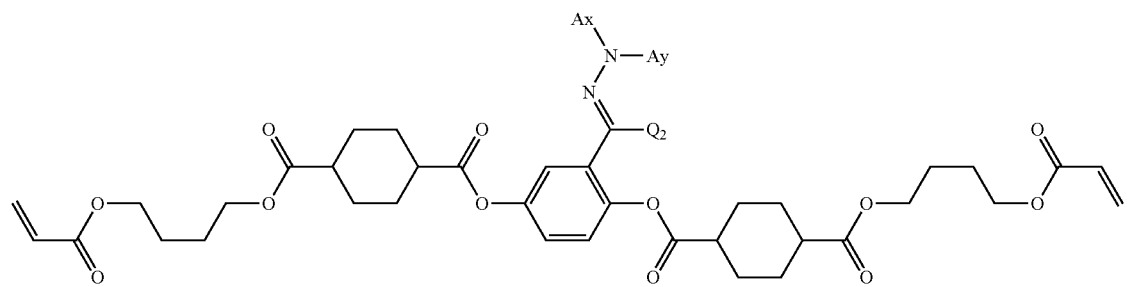
| No | Ax | Ay | Q2 |
|---|---|---|---|
| II-3-50 | benzothiazol-2-yl | benzyl | H |
| II-3-51 | benzothiazol-2-yl | *-S(O)₂-C₆H₄-CH₃ (tosyl) | H |
| II-3-52 | benzothiazol-2-yl | *-CH₂-O-CH₂CH₂-O-CH₃ | H |
| II-3-53 | benzothiazol-2-yl | butanoyl | H |
| II-3-54 | naphtho[1,2-d]thiazol-2-yl | $C_6H_{13}$ | H |
II-3-55
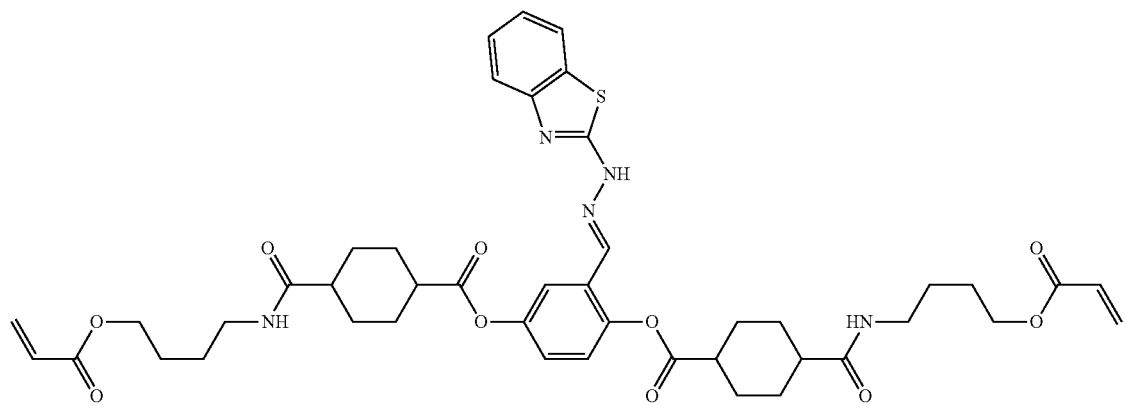

II-4-1
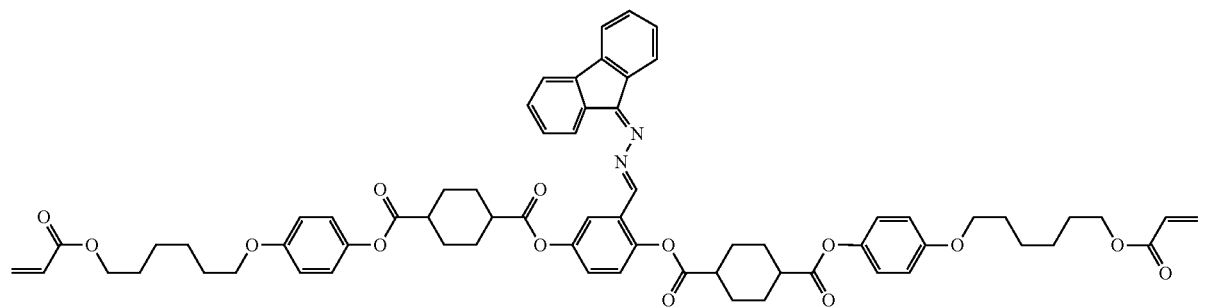
II-4-2
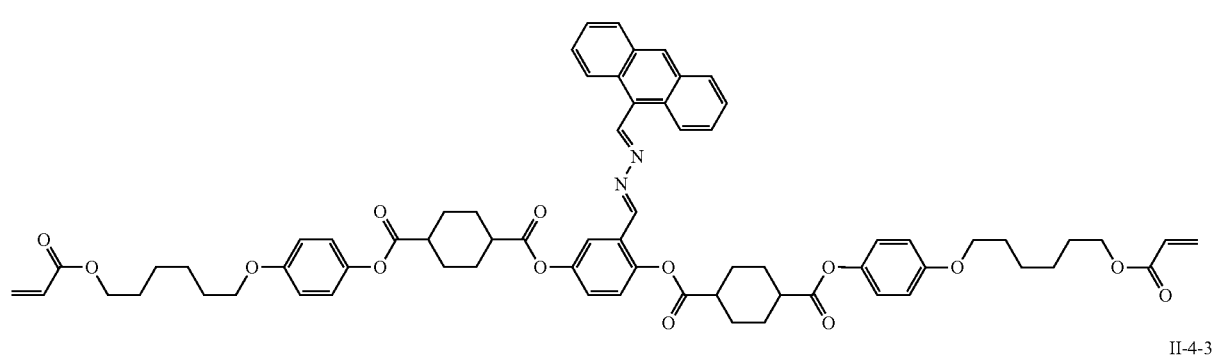
II-4-3
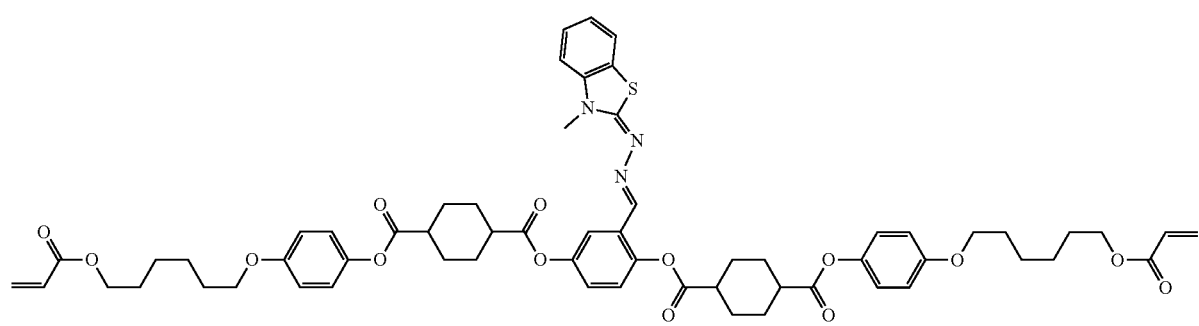
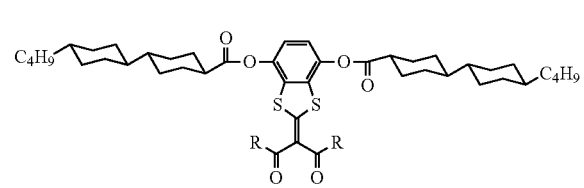
(10)
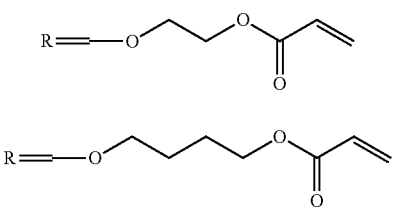
(11)
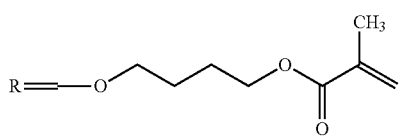
(12)
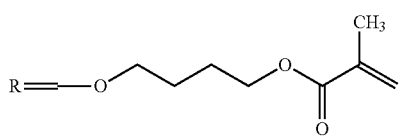
-continued
(13)
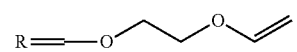
(14)
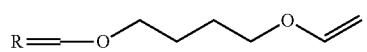
(15)
(16)
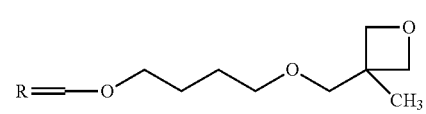
(17)
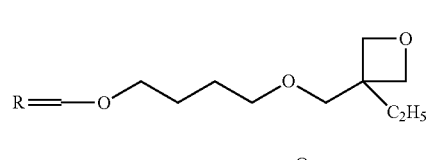
(18)
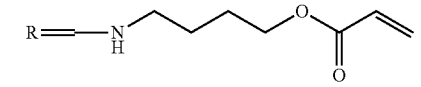

-continued

R═══CH₃ (19)

The pKa of the compound used for formation of Ar in Formula (I) is preferably 8.0 to 10.0, more preferably 8.1 to 9.5, and still more preferably 8.2 to 9.0. By adjusting the pKa of the compound used for formation of Ar to be within the range, the compatibility between the polymerizable liquid crystal compound and the aromatic polyether-based compound is improved. Thus, the durability and the light fastness of the optically anisotropic film are further improved.

In the present invention, the pKa of the compound used for formation of Ar refers to a first acid dissociation constant (pKa1). The Ar portion in Formula (I) is also referred to as a core portion of the polymerizable liquid crystal compound, and in a case where the pKa of the compound used for formation of the core portion is in a range of 5.8 to 10.0, the polymerizable liquid crystal compound having reverse-wavelength dispersion properties is easily obtained.

Here, the pKa means a pKa in an aqueous solution and is described in, for example, in Chemical Handbook (II) (Revised 4$^{th}$ Edition, 1993, compiled by the Chemical Society of Japan, Maruzen Company, Ltd.), and a lower value thereof indicates higher acid strength. Specifically, the pKa in an aqueous solution can be calculated by measuring the acid dissociation constant at 25° C., using an infinite-dilution aqueous solution, or a value based on Hammett substituent constants and the database of well-known literature can also be determined by computation using the following software package 1. All the values of pKa described in the present specification indicate values (pKa calculated) determined by computation using this software package.

<Software Package 1>

Advanced Chemistry Development (ACD/Labs) Software V 8.14 for Solaris (1994-2007 ACD/Labs).

Specific examples of the compound used for formation of Ar in Formula (I) include the following compounds including phenol structures.

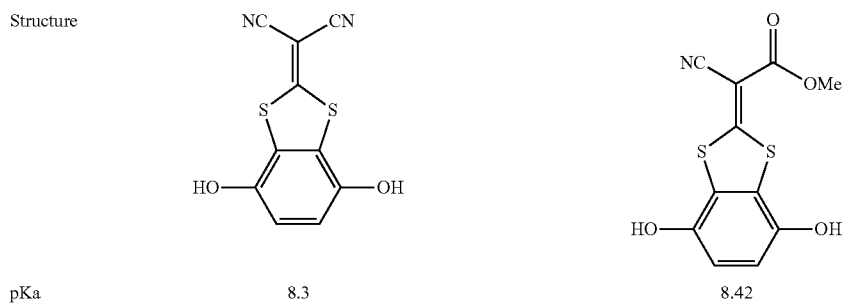

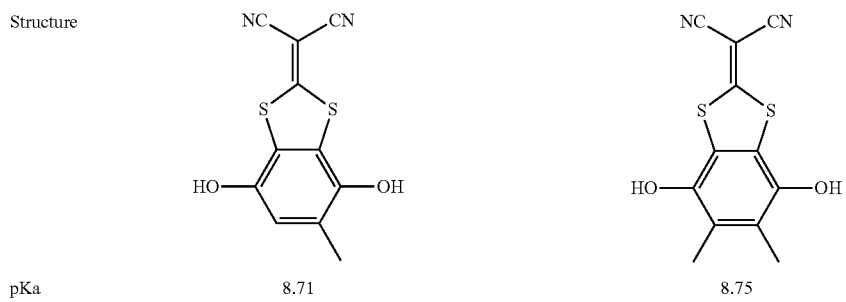

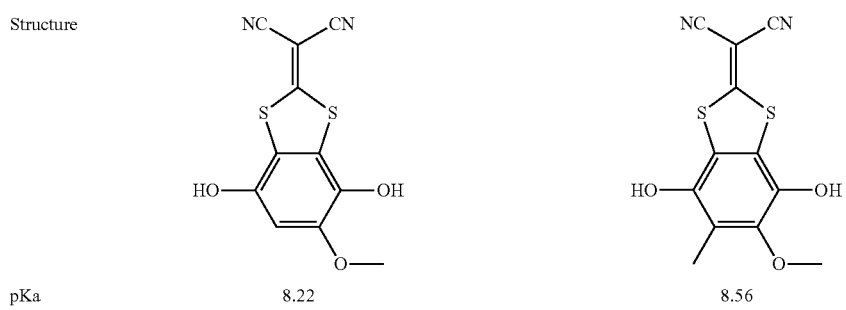

| | | |
|---|---|---|
| Structure | 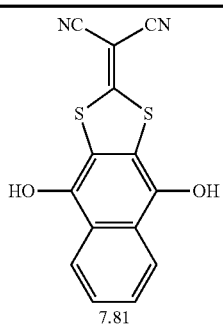 | 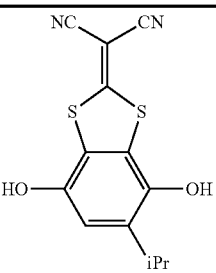 |
| pKa | 7.81 | 8.66 |
| Structure | 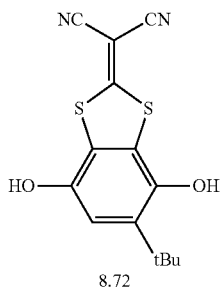 | 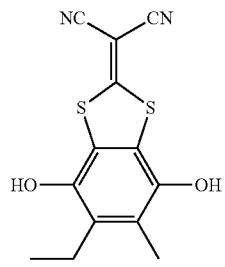 [SMILES: CCc1c(C)c(O)c2c(c1O)SC(=C(C#N)C#N)S2] |
| pKa | 8.72 | 9 |
| Structure | 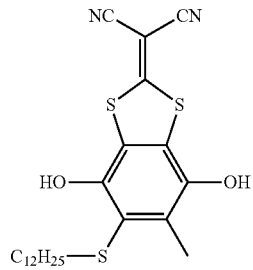 | 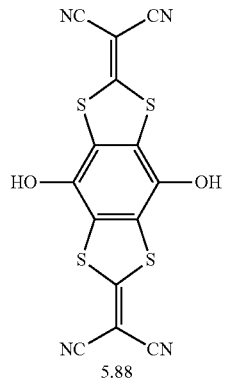 |
| pKa | 7.88 | 5.88 |
| Structure | 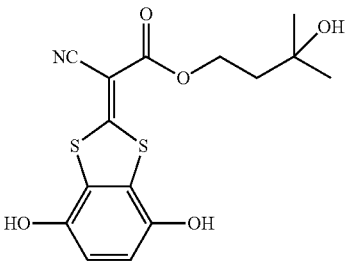 [SMILES: CC(C)(O)CCOC(=O)C(C#N)=C1Sc2c(O)ccc(O)c2S1] | 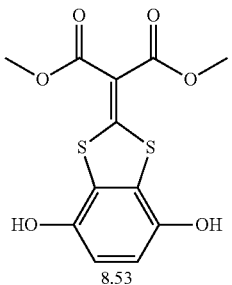 |
| pKa | 8.41 | 8.53 |
| Structure | 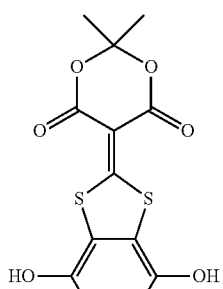 | 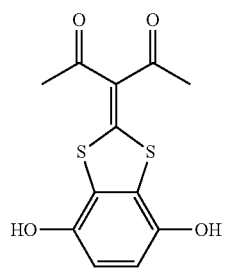 |
| pKa | 8.57 | 8.49 |

-continued
| | | |
|---|---|---|
| Structure | 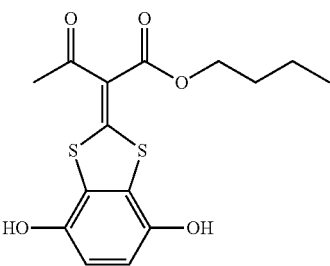 [SMILES: CCCCOC(=O)C(C(C)=O)=C1Sc2c(O)ccc(O)c2S1] | 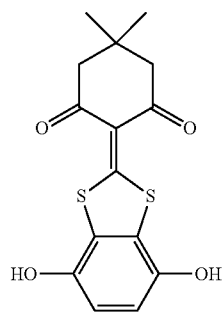 [SMILES: CC1(C)CC(=O)C(=C2Sc3c(O)ccc(O)c3S2)C(=O)C1] |
| pKa | 8.5 | 8.45 |
| Structure | 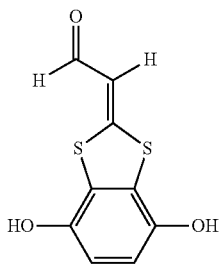 [SMILES: O=CC=C1Sc2c(O)ccc(O)c2S1] | 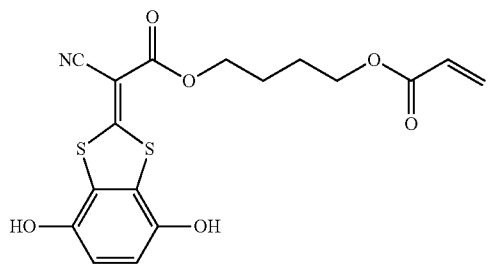 [SMILES: C=CC(=O)OCCCCOC(=O)C(C#N)=C1Sc2c(O)ccc(O)c2S1] |
| pKa | 8.85 | 8.4 |
| Structure | 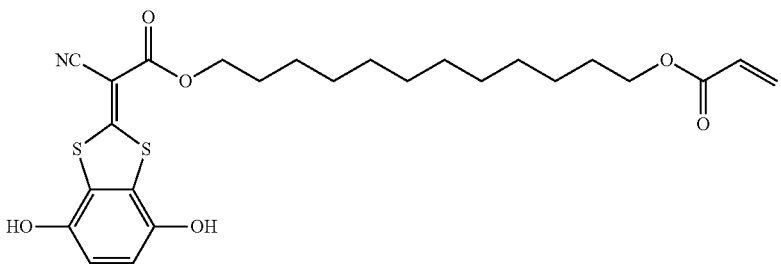 [SMILES: C=CC(=O)OCCCCCCCCCCCCOC(=O)C(C#N)=C1Sc2c(O)ccc(O)c2S1] | |
| pKa | 8.41 | |
| Structure | 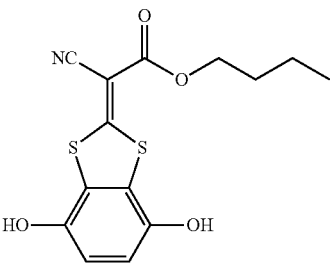 [SMILES: CCCCOC(=O)C(C#N)=C1Sc2c(O)ccc(O)c2S1] | 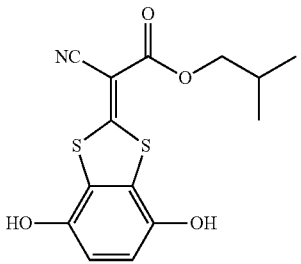 [SMILES: CC(C)COC(=O)C(C#N)=C1Sc2c(O)ccc(O)c2S1] |
| pKa | 8.41 | 8.4 |
| Structure | 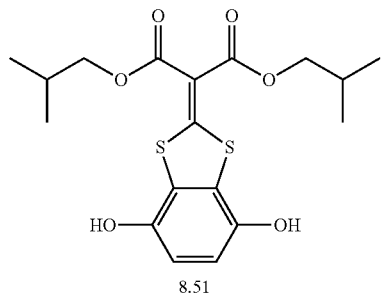 | 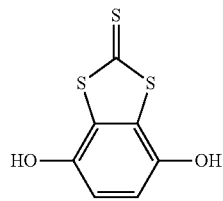 [SMILES: Oc1ccc(O)c2sc(=S)sc12] |
| pKa | 8.51 | 7.84 |

-continued
| Structure | 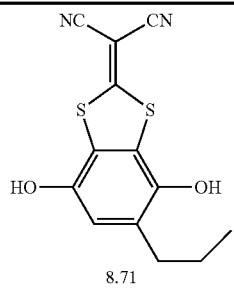 | 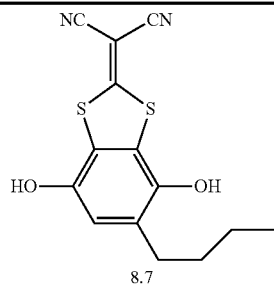 |
|---|---|---|
| pKa | 8.71 | 8.7 |
| Structure | 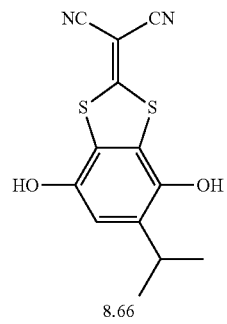 | 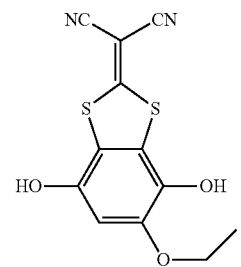 [SMILES: CCOc1cc(O)c2c(c1O)SC(=C(C#N)C#N)S2] |
| pKa | 8.66 | 8.26 |
| Structure | 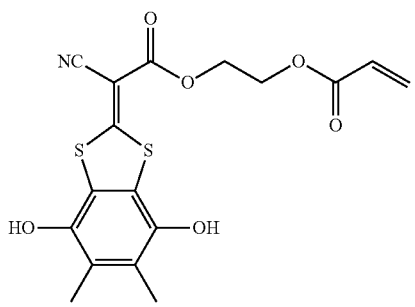 [SMILES: C=CC(=O)OCCOC(=O)C(C#N)=C1Sc2c(O)c(C)c(C)c(O)c2S1] | |
| pKa | 8.83 | |
40
| Structure | 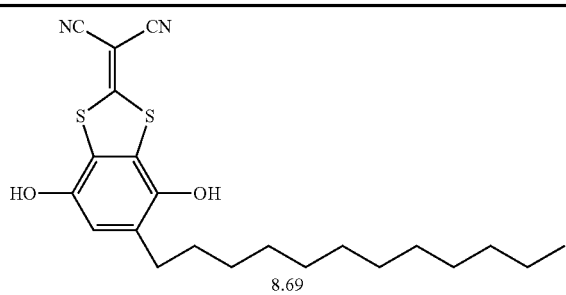 |
|---|---|
| pKa | 8.69 |
| Structure | 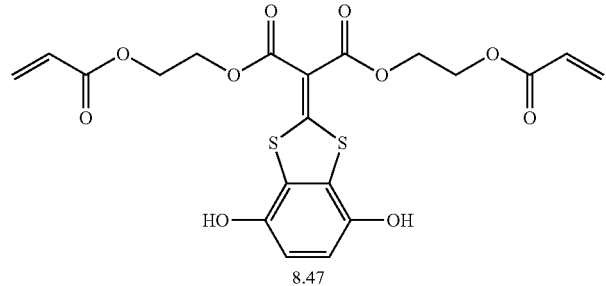 |
| pKa | 8.47 |

-continued

| Structure | | |
|---|---|---|
| pKa | 8.48 | 8.67 |
| Structure | | |
| pKa | 8.79 | 8.99 |
| Structure | | |
| pKa | 8.79 | 8.19 |
| Structure | | |
| pKa | 8.78 | 8.48 |
| Structure | | |
| pKa | 8.57 | 8.33 |

-continued
| Structure | 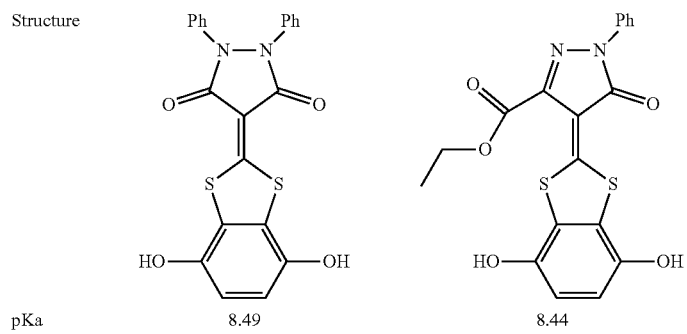 | 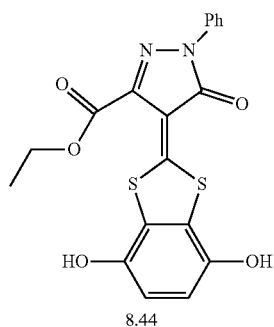 |
|---|---|---|
| pKa | 8.49 | 8.44 |
| Structure | 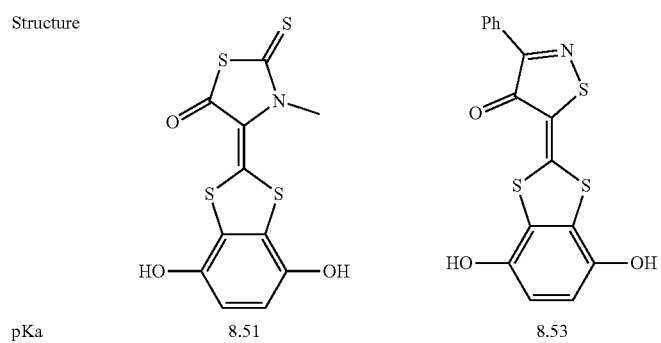 | 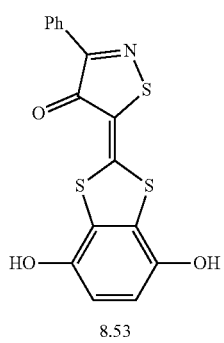 |
|---|---|---|
| pKa | 8.51 | 8.53 |
| Structure | 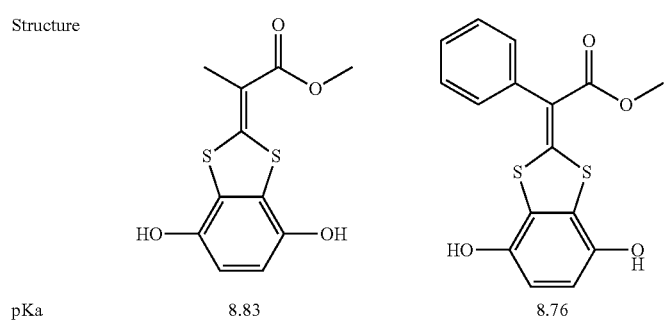 | 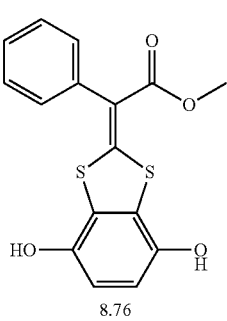 |
|---|---|---|
| pKa | 8.83 | 8.76 |
| Structure | 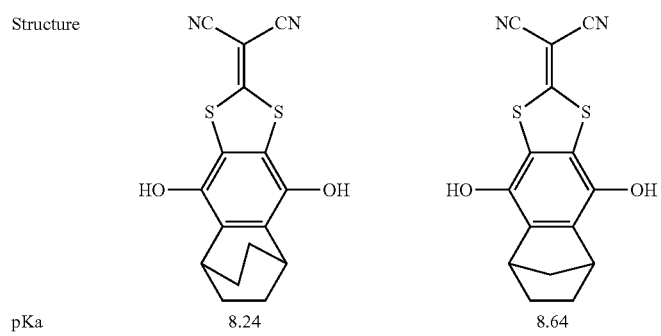 | 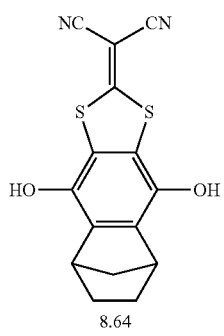 |
|---|---|---|
| pKa | 8.24 | 8.64 |

| Structure | 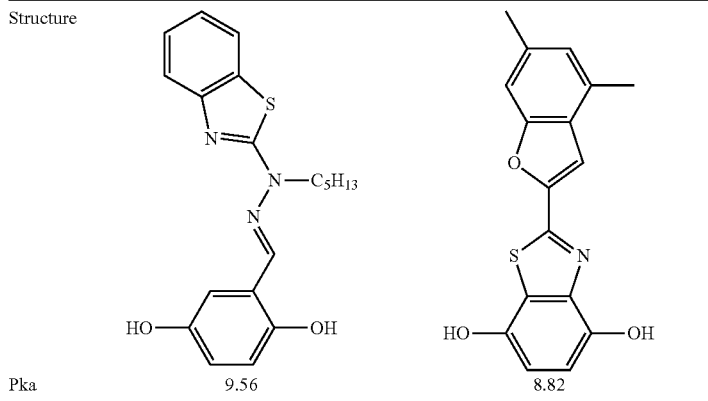 |
|---|---|
| Pka | 9.56       8.82 |

The polymerizable liquid crystal composition of the embodiment of the present invention may contain a liquid crystalline compound having forward wavelength dispersion properties (hereinafter also referred to as "forward dispersion"), in addition to the above-mentioned polymerizable liquid crystal compound having reverse-wavelength dispersion properties.

Here, in the present specification, the liquid crystalline compound having "forward wavelength dispersion properties" refers to a compound in which an in-plane retardation (Re) value decreases with an increase in a measurement wavelength as the Re value at a specific wavelength (visible light range) of a retardation film manufactured using the liquid crystalline compound is measured.

In the present invention, in a case where the liquid crystalline compound exhibiting forward wavelength dispersion properties is contained, the content thereof is not particularly limited, but is preferably 1 to 40 parts by mass, and more preferably 10 to 30 parts by mass, with respect to 100 parts by mass of a total amount of the above-mentioned polymerizable liquid crystal compound having reverse-wavelength dispersion properties and the liquid crystalline compound exhibiting forward wavelength dispersion properties.

[Aromatic Polyether-Based Compound]

In the present invention, the aromatic polyether-based compound means a compound having a skeleton in which two or more hydrogen atoms in one aromatic ring are substituted with etheric oxygen atoms. Examples of the aromatic ring include a benzene ring and an aromatic heterocyclic ring (for example, a thiophene ring and a pyrrole ring).

The aromatic polyether-based compound may have a plurality of aromatic rings in one molecule. In this case, two or more hydrogen atoms in each of the plurality of aromatic rings may be substituted with etheric oxygen atoms.

From the viewpoint that the light fastness of the optically anisotropic film is further improved, the aromatic polyether-based compound preferably includes at least one compound selected from the group consisting of Formula (A) and Formula (B) which will be described later.

<Compound Represented by Formula (A)>

First, the compound represented by Formula (A) will be described.

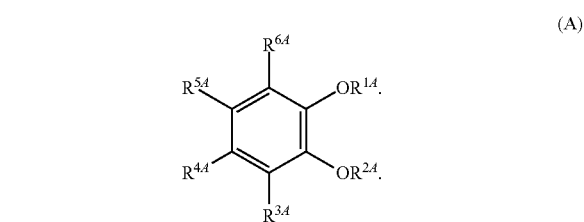

In Formula (A), $R^{1A}$ and $R^{2A}$ each independently represent a monovalent organic group, and $R^{3A}$, $R^{4A}$, $R^{5A}$, and $R^{6A}$ each independently represent a hydrogen atom or a monovalent substituent. $R^{1A}$ and $R^{2A}$, $R^{2A}$ and $R^{3A}$, $R^{3A}$ and $R^{4A}$, $R^{4A}$ and $R^{5A}$, $R^{5A}$ and $R^{6A}$, or $R^{6A}$ and $R^{1A}$ may be bonded to each other to form a ring.

Furthermore, the oxygen atom bonded to each of $R^{1A}$ and $R^{2A}$ shown in Formula (A) represents an etheric oxygen atom.

The monovalent organic group represented by each of $R^{1A}$ and $R^{2A}$ may be an alkyl group (which may be linear, branched, or cyclic, and preferably has 1 to 20 carbon atoms), an alkenyl group (preferably having 1 to 20 carbon atoms), an aryl group (which may be a monocycle or a fused ring and preferably has 6 to 20 carbon atoms), a heterocyclic group (for example, a tetrahydropyranyl group and a pyrimidyl group), —Si($R^{7A}$)$_3$ ($R^{7A}$'s each independently represent a hydrogen atom or an alkyl group, provided that at least one $R^{7A}$'s is an alkyl group), a monovalent group formed by removing one hydrogen atom from the compound represented by Formula (A), a monovalent group formed by removing one hydrogen atom from the compound represented by Formula (B), and a group formed by combination of these groups.

In addition, the monovalent organic group represented by each of $R^{1A}$ and $R^{2A}$ may include —O—, provided that —O— is not directly bonded to the etheric oxygen atom shown in Formula (A).

The monovalent organic group represented by each of $R^{1A}$ and $R^{2A}$ may have a substituent such as a group represented by ($R^{8A}$)$_2$NC(=O)—, urea ($R^{8A}$—NHC(=O)NH—), and a hydroxy group. $R^{8A}$'s each independently represent a hydrogen atom, an aryl group, or an alkyl group. In a case where $R^{8A}$ is an aryl group or an alkyl group, the group may further have a substituent.

Examples of the monovalent substituent in each of $R^{3A}$, $R^{4A}$, $R^{5A}$, and $R^{6A}$ include a halogen atom, an alkyl group (which may be linear, branched, or cyclic, and preferably has 1 to 20 carbon atoms), an alkenyl group (preferably having 1 to 20 carbon atoms), an aryl group (which may be a monocycle or a fused ring, and preferably has 6 to 20 carbon atoms), a heterocyclic group (for example, a tetrahydropyranyl group and a pyrimidyl group), a group represented by $(R^{9A})_2NC(=O)-$, urea $(R^{9A}-NHC(=O)NH-)$, a monovalent group formed by removing one hydrogen atom from the compound represented by Formula (A), a monovalent group formed by removing one hydrogen atom from the compound represented by Formula (B), and a group formed by combination of two or more of these groups. $R^{9A}$'s each independently represent a hydrogen atom, an alkyl group, or an aryl group. Further, the alkyl group or the aryl group in $R^{9A}$ may have a substituent represented by $R^{10A}SO_2$-($R^{10A}$ represents an alkyl group).

In a case where $R^{3A}$, $R^{4A}$, $R^{5A}$, or $R^{6A}$ is an alkyl group, an alkenyl group, an aryl group, a monovalent group formed by removing one hydrogen atom from the compound represented by Formula (A), or a monovalent group formed by removing one hydrogen atom from the compound represented by Formula (B), the group may include a bond represented by —O—.

In a case where $R^{1A}$ and $R^{2A}$ are bonded to each other to form a ring (hetero ring), the number of carbon atoms constituting the ring is preferably 3 to 5. The ring thus formed may have a substituent such as an alkyl group.

In a case where $R^{2A}$ and $R^{3A}$, or $R^{6A}$ and $R^{1A}$ are bonded to each other to form a ring (hetero ring), the number of carbon atoms constituting the ring is preferably 4 to 6. The ring thus formed may have a substituent such as an alkyl group.

In a case where $R^{3A}$ and $R^{4A}$, $R^{4A}$ and $R^{5A}$, or $R^{5A}$ and $R^{6A}$ are bonded to each other to form a ring (hydrocarbon ring or hetero ring), the number of carbon atoms constituting the ring is preferably 5 to 7. The ring thus formed may have a substituent such as an alkyl group and an alkoxy group. Further, the substituents of the ring formed may further be bonded to each other to form a ring, and in this case, a ring formed by the bonding of $R^{3A}$ and $R^{4A}$, $R^{4A}$ and $R^{5A}$, or $R^{5A}$ and $R^{6A}$ and a ring formed by the mutual bonding of the substituents may constitute a spiro ring or a fused ring.

An example of suitable aspects of the compound represented by Formula (A) may be a compound represented by Formula (C) or Formula (D).

(Compound Represented by Formula (C))

The compound represented by Formula (C) will be described.

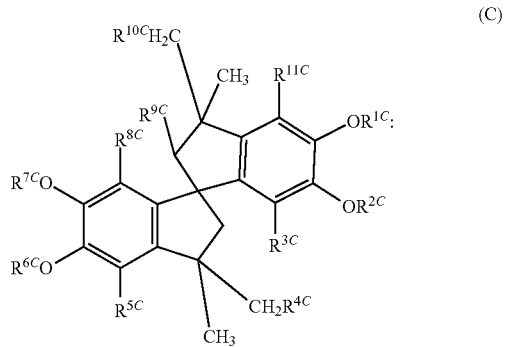

(C)

In Formula (C), $R^{1C}$, $R^{2C}$, $R^{6C}$, and $R^{7C}$ each independently represent a monovalent organic group, $R^{3C}$, $R^{5C}$, $R^{8C}$, and $R^{11C}$ each independently represent a hydrogen atom or a monovalent substituent, an $R^{4C}$, $R^{9C}$ and $R^{10C}$ each independently represent a hydrogen atom or a monovalent organic group.

Furthermore, the oxygen atom bonded to each of $R^{1C}$, $R^{2C}$, $R^{6C}$, and $R^{7C}$ shown in Formula (C) represents an etheric oxygen atom.

Specific examples of the monovalent organic group represented by each of $R^{1C}$, $R^{2C}$, $R^{6C}$, and $R^{7C}$ are the same as those of the monovalent organic group represented by each of $R^{1A}$ and $R^{2A}$.

Specific examples of the monovalent substituent represented by each of $R^{3C}$, $R^{5C}$, $R^{8C}$, and $R^{11C}$ are the same as those of the monovalent substituent represented by each of $R^{3A}$, $R^{4A}$, $R^{5A}$, and $R^{6A}$.

Examples of the monovalent organic group represented by each of $R^{4C}$, $R^{9C}$, and $R^{10C}$ include an alkyl group (which may be linear, branched, or cyclic, and preferably has 1 to 20 carbon atoms), an alkenyl group (preferably having 1 to 20 carbon atoms), and an aryl group (which may be a monocycle or a fused ring, and preferably has 6 to 20 carbon atoms), and these groups may have a substituent such as a halogen atom and an alkoxy group.

(Compound Represented by Formula (D))

The compound represented by Formula (D) will be described.

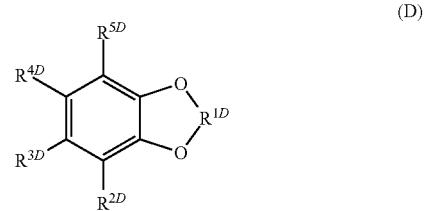

(D)

In Formula (D), $R^{1D}$ represents an alkylene group having 1 to 3 carbon atoms, and $R^{2D}$, $R^{3D}$, $R^{4D}$, and $R^{5D}$ each independently represent a hydrogen atom or a monovalent substituent. Further, $R^{2D}$ and $R^{3D}$, or $R^{3D}$ and $R^{4D}$ may be bonded to each other to form a ring.

Furthermore, the oxygen atom bonded to $R^{1D}$ shown in Formula (D) represents an etheric oxygen atom.

The alkylene group having 1 to 3 carbon atoms represented by $R^{1D}$ may be substituted with at least one substituent selected from the group consisting of a halogen atom, an alkyl group (which may be linear, branched, or cyclic, and preferably has 1 to 20 carbon atoms), an aryl group (which may be a monocycle or a fused ring, and preferably has 6 to 20 carbon atoms), an alkoxy group, an aryloxy group, a group represented by =S, and a group represented by =O. Specific examples of the substituent in $R^{1D}$ are the same as the substituents of Z in General Formula (I) in JP1987-010420B (JP-S62-010420B).

$R^{1D}$ is preferably an unsubstituted alkylene group, or an alkylene group substituted with an alkyl group or an aryl group.

Examples of the monovalent substituent represented by each of $R^{2D}$, $R^{3D}$, $R^{4D}$, and $R^{5D}$ include a halogen atom, an alkyl group, an aryl group (which may be a monocycle or a fused ring), an alkoxy group, an aryloxy group, an alkylthio group, an acyl group, an acylamino group, a sulfonamido group, a diacylamino group, a carboxy group, a sulfo group, and a hydroxy group, and these substituents may be further substituted. Specific examples of each group are the same as those of $R^1$, $R^2$, $R^3$, and $R^4$ in General Formula (I) in JP1987-010420B (JP-S62-010420B), respectively.

As $R^{2D}$, $R^{3D}$, $R^{4D}$, and $R^{5D}$, a hydrogen atom, a halogen atom, an alkyl group, an alkoxy group, or an alkylthio group is preferable.

In a case where $R^{2D}$ and $R^{3D}$, or $R^{3D}$ and $R^{4D}$ are bonded to each other to form a ring, examples of the ring include a hydrocarbon ring and a hetero ring.

Examples of the hydrocarbon ring that can be formed by the bonding of $R^{2D}$ and $R^{3D}$, or $R^{3D}$ and $R^{4D}$ include an indane ring, a spiroindane ring, a naphthalene ring, and a tetrahydronaphthalene ring. These hydrocarbon rings may be substituted with a group exemplified as a substituent of the hydrocarbon ring formed by ring closure of $R^1$ and $R^2$, or $R^2$ and $R^3$ in General Formula (I) in JP1987-010420B (JP-S62-010420B).

Examples of the hetero ring that can be formed by the bonding of $R^{2D}$ and $R^{3D}$, or $R^{3D}$ and $R^{4D}$ include a chroman ring, a coumaran ring, a spirochroman ring, and a spirocoumaran ring. These hetero rings may be substituted with a group exemplified as a substituent of the hetero ring formed by ring closure of $R^1$ and $R^2$, or $R^2$ and $R^3$ in General Formula (I) in JP1987-010420B (JP-S62-010420B).

Out of $R^{2D}$ and $R^{3D}$, and $R^{3D}$ and $R^{4D}$, $R^{3D}$ and $R^{4D}$ are preferably bonded to each other to form a ring.

The compound represented by Formula (D) may be a compound having a skeleton represented by Formula (D-1). The compound having a skeleton represented by Formula (D-1) comprises a structure in which $R^{3D}$ and $R^{4D}$ in Formula (D) are bonded to each other to form a spiroindane ring, and the spiroindane ring is substituted with a compound represented by Formula (d1).

The definition of $R^{6D}$ in Formula (d1) and Formula (D-1) is the same as that of $R^{1D}$ in Formula (D), and $R^{1D}$ in Formula (D-1) represents $R^{1D}$ in Formula (D).

(d1)

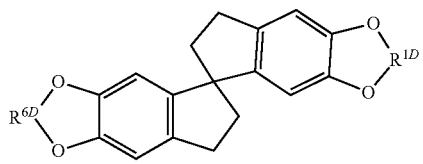

(D-1)

The compound represented by Formula (D) may be a compound having a skeleton represented by Formula (D-2) or a compound having a skeleton represented by Formula (D-3).

The compound having a skeleton represented by Formula (D-2) comprises a structure in which $R^{3D}$ and $R^{4D}$ in Formula (D) are bonded to each other to form a spirochroman ring, and the spirochroman ring is substituted with the compound represented by Formula (d1).

The compound having a skeleton represented by Formula (D-3) comprises a structure in which $R^{3D}$ and $R^{4D}$ in Formula (D) are bonded to each other to form a spirocoumaran ring, and the spirocoumaran ring is substituted with the compound represented by Formula (d1).

The definition of $R^{6D}$ in Formula (D-2) and Formula (D-3) is the same as that of $R^{1D}$ in Formula (D), and $R^{1D}$ in Formula (D-2) and Formula (D-3) represents $R^{1D}$ in Formula (D).

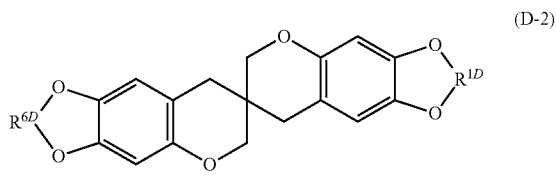

(D-2)

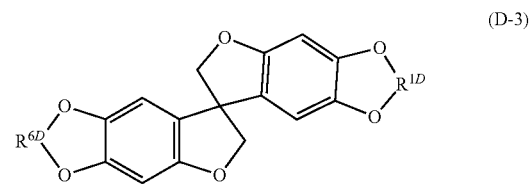

(D-3)

Specific examples of the compounds represented by Formula (A), Formula (C), and Formula (D) are shown below.

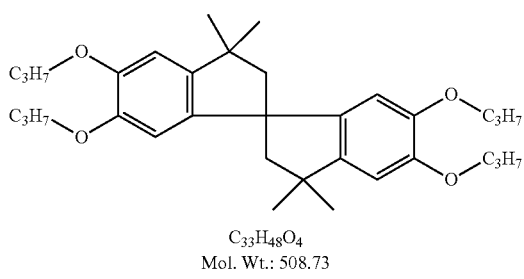

$C_{33}H_{48}O_4$
Mol. Wt.: 508.73

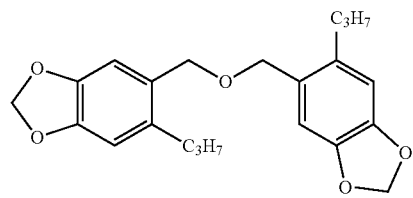

$C_{22}H_{26}O_5$
Mol. Wt.: 370.44

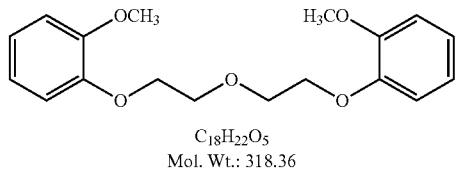

$C_{18}H_{22}O_5$
Mol. Wt.: 318.36

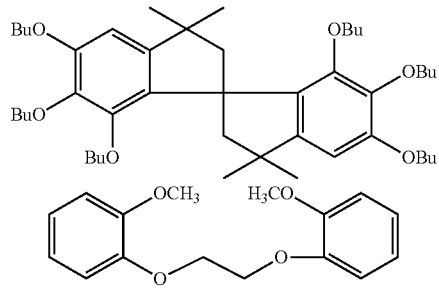

$C_{16}H_{18}O_4$
Mol. Wt.: 274.31

-continued
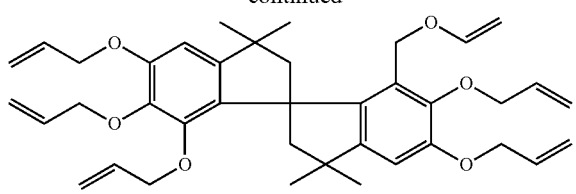
C₄₀H₅₀O₆
Mol. Wt.: 626.82
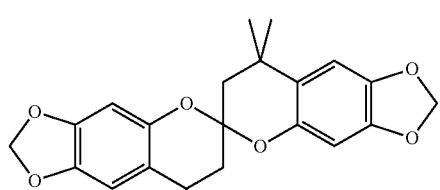
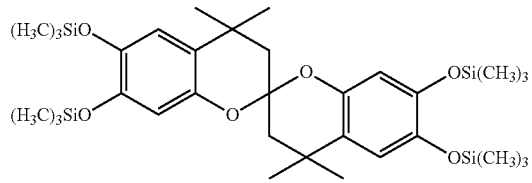
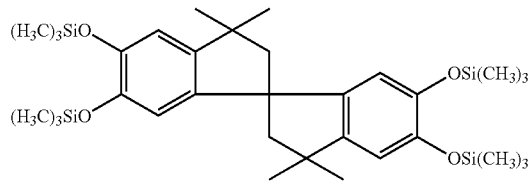
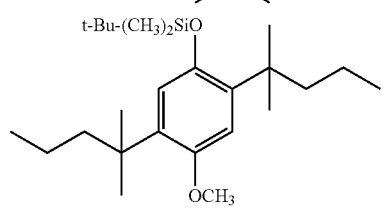
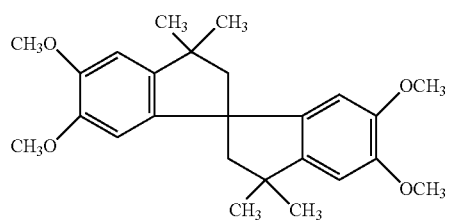
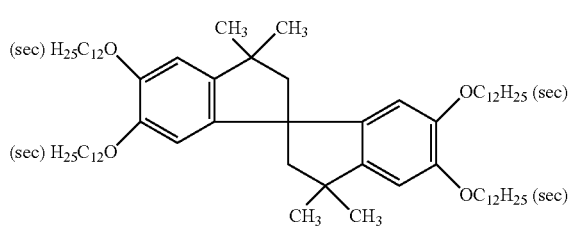
-continued
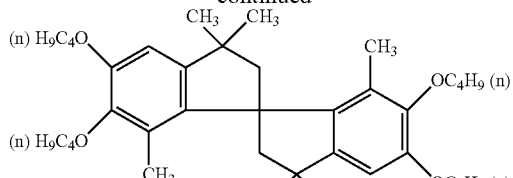
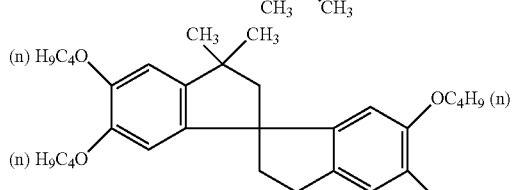
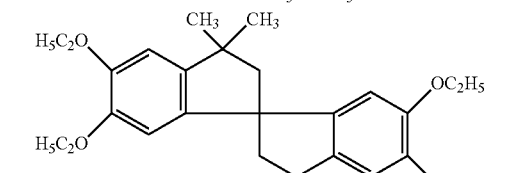
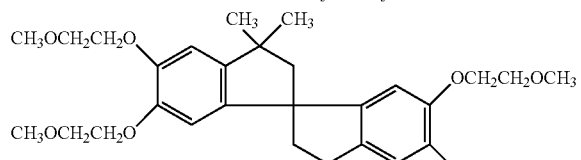
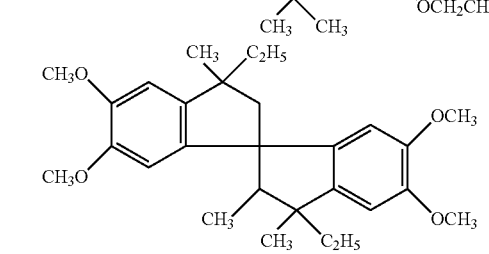
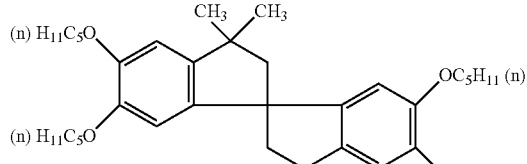
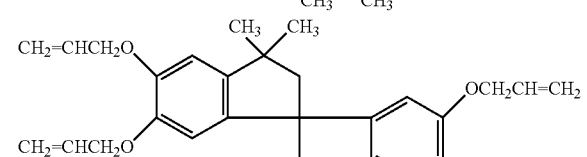
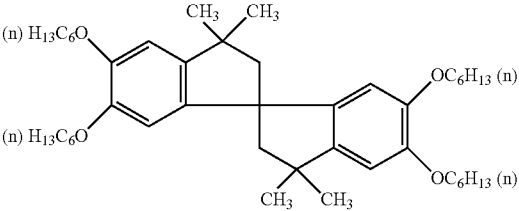

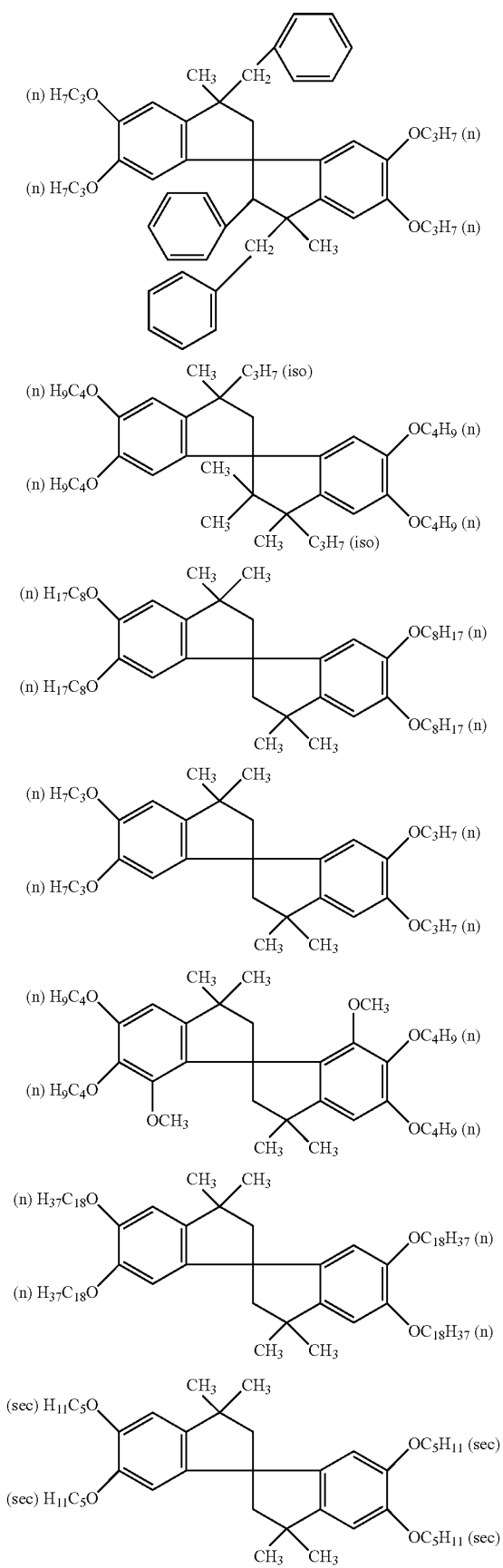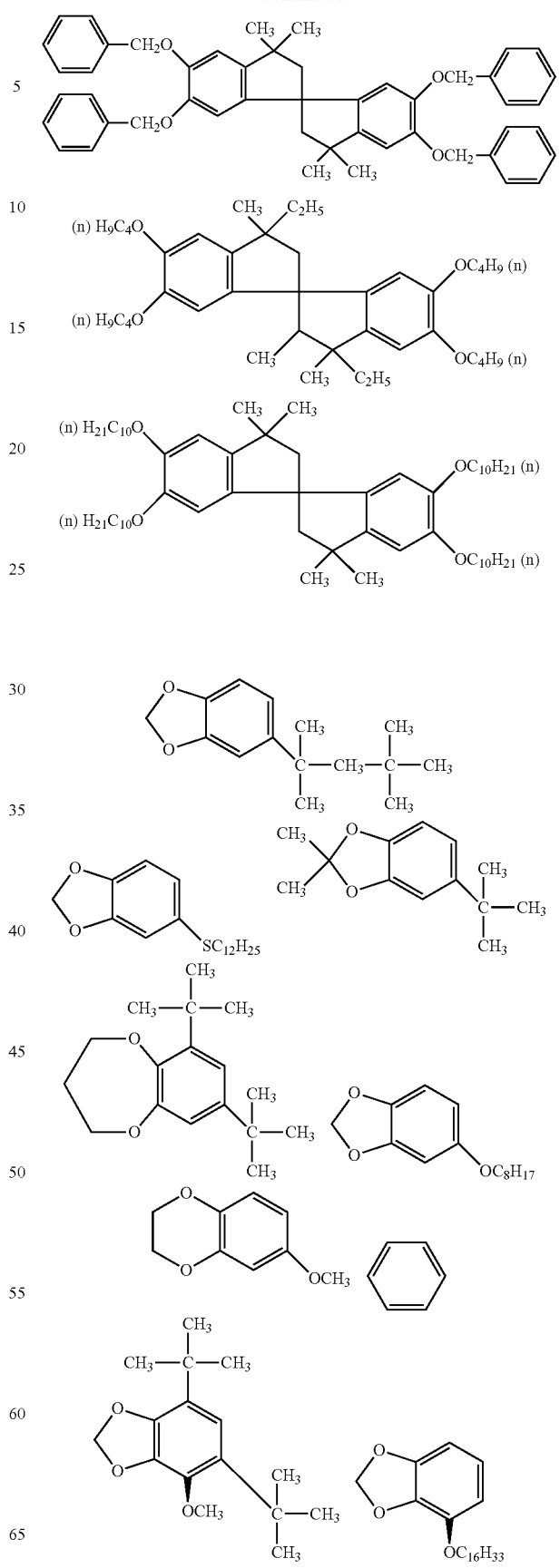

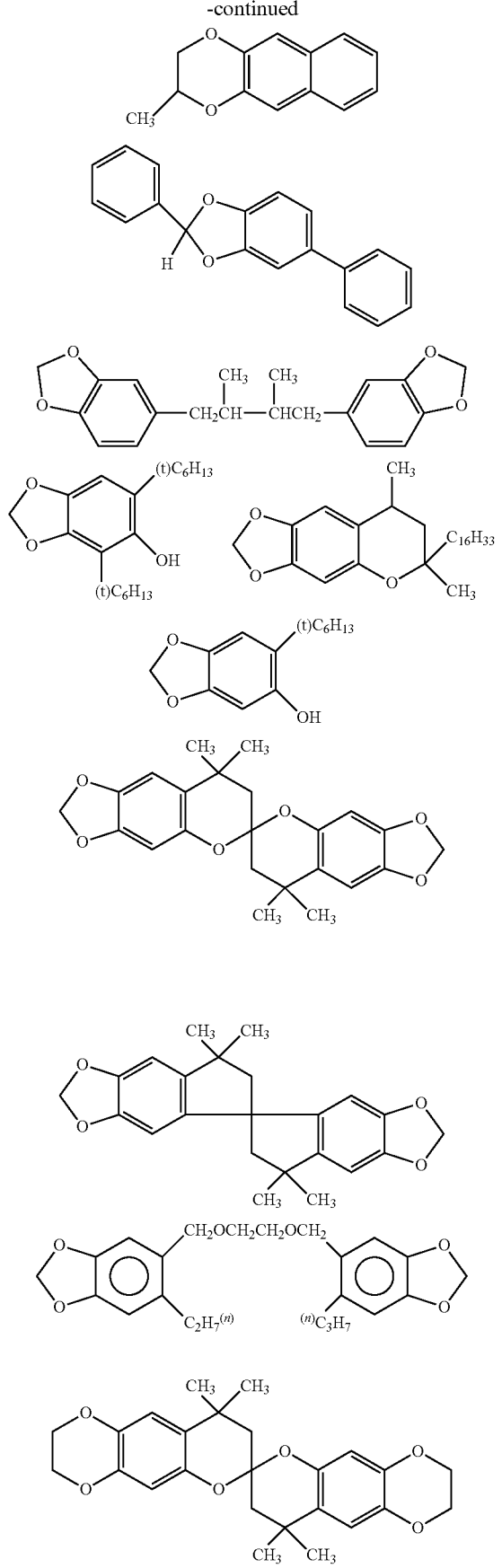
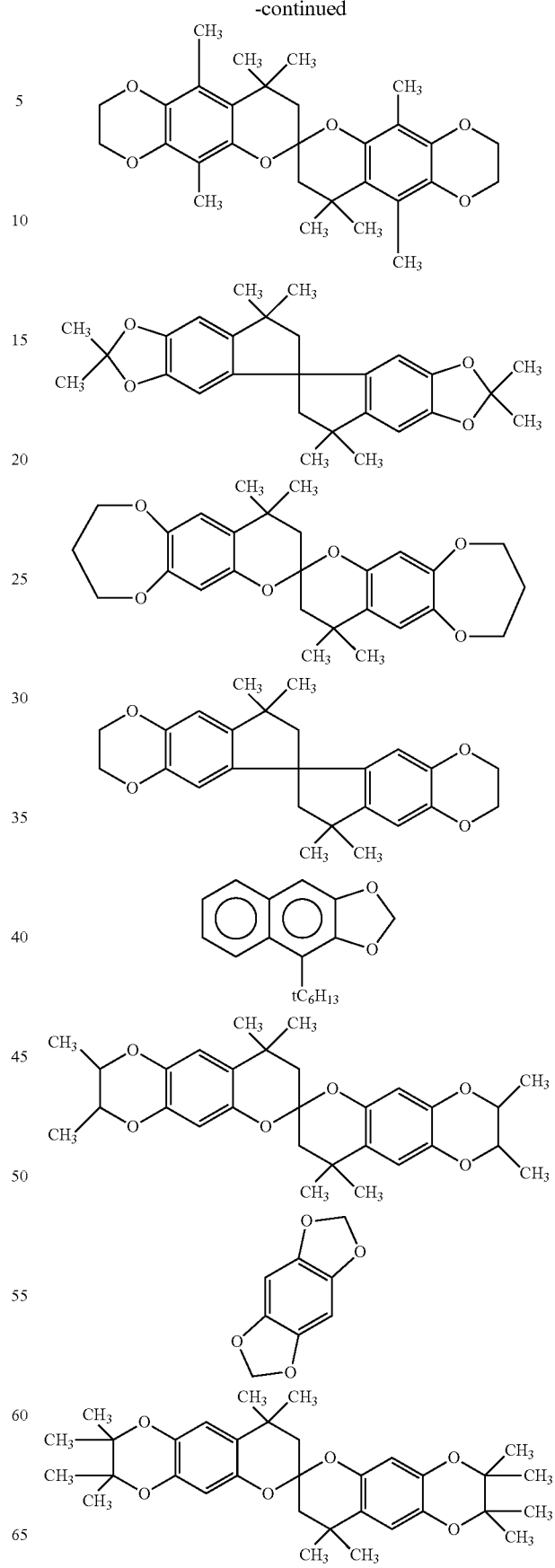

-continued

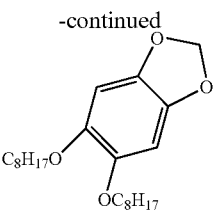

<Compound Represented by Formula (B)>

Next, the compound represented by Formula (B) will be described.

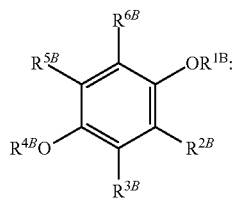

In Formula (B), $R^{1B}$ and $R^{4B}$ each independently represent a monovalent organic group, and $R^{2B}$, $R^{3B}$, $R^{5B}$, and $R^{6B}$ each independently represent a hydrogen atom or a monovalent substituent. $R^{1B}$ and $R^{2B}$, $R^{2B}$ and $R^{3B}$, $R^{3B}$ and $R^{4B}$, $R^{4B}$ and $R^{5B}$, $R^{5B}$ and $R^{6B}$, or $R^{6B}$ and $R^{1B}$ may be bonded to each other to form a ring.

Furthermore, the oxygen atom bonded to each of $R^{1B}$ and $R^{4B}$ shown in Formula (B) represents an etheric oxygen atom.

Specific examples of the monovalent organic group represented by each of $R^{1B}$ and $R^{4B}$ are the same as those of the monovalent organic group represented by each of $R^{1A}$ and $R^{2A}$.

Specific examples of the monovalent substituent represented by each of $R^{2B}$, $R^{3B}$, $R^{5B}$, and $R^{6B}$ are the same as those of the monovalent substituent represented by each of $R^{3A}$, $R^{4A}$, $R^{5A}$, and $R^{6A}$.

In a case where $R^{1B}$ and $R^{2B}$, $R^{3B}$ and $R^{4B}$, $R^{4B}$ and $R^{5B}$, or $R^{6B}$ and $R^{1B}$ are bonded to each other to form a ring (hetero ring), the number of carbon atoms constituting the ring is preferably 4 to 6. The ring thus formed may have a substituent such as an alkyl group and an alkoxy group. Further, the substituents of the ring formed may further be bonded to each other to form a ring, and in this case, a ring formed by the bonding of $R^{1B}$ and $R^{2B}$, $R^{3B}$ and $R^{4B}$, $R^{4B}$ and $R^{5B}$, or $R^{6B}$ and $R^{1B}$ and a ring formed by the mutual bonding of the substituents may constitute a spiro ring or a fused ring.

In a case where $R^{2B}$ and $R^{3B}$, or $R^{5B}$ and $R^{6B}$ are bonded to each other to form a ring (a hydrocarbon ring or a hetero ring), the number of carbon atoms constituting the ring is preferably 5 to 7. Further, the ring thus formed may have a substituent such as an alkyl group.

An example of suitable aspects of the compound represented by Formula (B) may be a compound represented by Formula (E) or Formula (F).

(Compound Represented by Formula (E))

The compound represented by Formula (E) will be described.

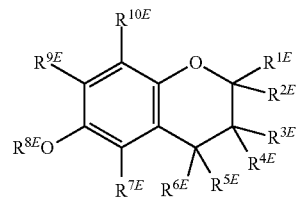

In Formula (E), $R^{1E}$, $R^{2E}$, $R^{3E}$, $R^{4E}$, $R^{5E}$, and $R^{6E}$ each independently represent a hydrogen atom or a monovalent organic group, $R^{7E}$, $R^{9E}$, and $R^{10E}$ each independently represent a hydrogen atom or a monovalent substituent, and $R^{8E}$ represents a monovalent organic group. $R^{1E}$ and $R^{2E}$, or $R^{3E}$ and $R^{4E}$ may be bonded to each other to form a ring.

Furthermore, the oxygen atom bonded to the benzene ring shown in Formula (E) represents an etheric oxygen atom.

The monovalent organic group represented by each of $R^{1E}$, $R^{2E}$, $R^{3E}$, $R^{4E}$, $R^{5E}$, and $R^{6E}$ may be an alkyl group (which may be linear, branched, or cyclic, and preferably has 1 to 20 carbon atoms), an alkenyl group (preferably having 1 to 20 carbon atoms), an alkoxy group (which may be linear, branched, or cyclic, and preferably has 1 to 20 carbon atoms), an aryl group (which may be a monocycle or a fused ring, and preferably has 6 to 20 carbon atoms), and a group formed by combination of these groups, and these groups may have a substituent such as a halogen atom.

Specific examples of the monovalent substituent represented by each of $R^{7E}$, $R^{9E}$, and $R^{10E}$ are the same as those of the monovalent substituent represented by each of $R^{3A}$, $R^{4A}$, $R^{5A}$, and $R^{6A}$.

The monovalent organic group represented by $R^{8E}$ is the same as the monovalent organic group represented by $R^{1A}$ and $R^{2A}$.

In a case where $R^{1E}$ and $R^{2E}$, or $R^{3E}$ and $R^{4E}$ are bonded to each other to form a ring (a hydrocarbon ring or a hetero ring), the number of carbon atoms constituting the ring is preferably 4 to 6. The ring thus formed may have a substituent such as an alkyl group and an alkoxy group. Further, the substituents of the ring formed may further be bonded to each other to form a ring, and in this case, a ring formed by the bonding of $R^{1E}$ and $R^{2E}$, or $R^{3E}$ and $R^{4E}$ and a ring formed by the mutual bonding of the substituents may constitute a fused ring.

Examples of the compound represented by Formula (E), in which $R^{1E}$ and $R^{2E}$ are bonded to each other to form a ring, include a compound having a skeleton represented by Formula (E-1).

The compound having a skeleton represented by Formula (E-1) is a compound having a spirochroman ring structure. $R^{8E}$ in Formula (E-1) represents $R^{8E}$ in Formula (E).

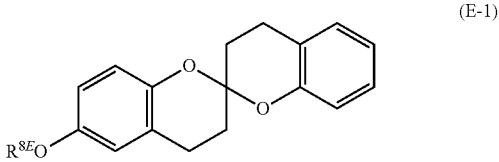

(Compound Represented by Formula (F))

The compound represented by Formula (F) will be described.

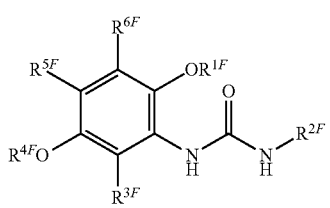

(F)

In Formula (F), $R^{1F}$ and $R^{4F}$ each independently represent a monovalent organic group, and $R^{2F}$, $R^{3F}$, $R^{5F}$, and $R^{6F}$ each independently represent a hydrogen atom or a monovalent substituent.

The monovalent organic group represented by each of $R^{1F}$ and $R^{4F}$ is the same as the monovalent organic group represented by each of $R^{1A}$ and $R^{2A}$.

The monovalent substituent represented by each of $R^{2F}$, $R^{3F}$, $R^{5F}$, and $R^{6F}$ is the same as the monovalent substituent represented by each of $R^{3A}$, $R^{4A}$, $R^{5A}$, and $R^{6A}$.

Specific examples of the compound represented by each of Formulae (B), (E), and (F) are shown below.

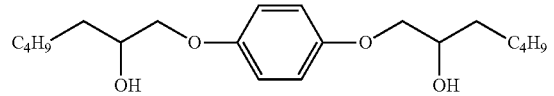

$C_{20}H_{34}O_4$
Mol. Wt.: 338.48

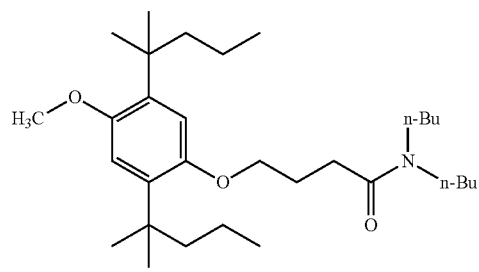

$C_{31}H_{55}NO_3$
Mol. Wt.: 489.77

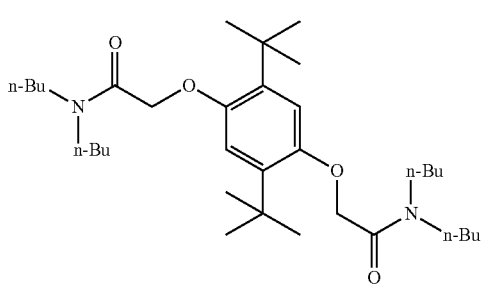

$C_{34}H_{60}N_2O_4$
Mol. Wt.: 560.85

-continued

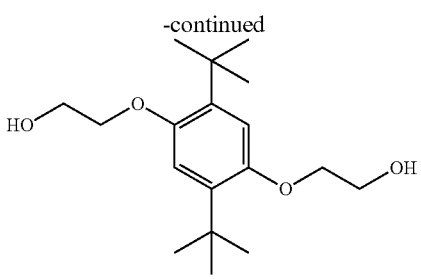

$C_{18}H_{30}O_4$
Mol. Wt.: 310.43

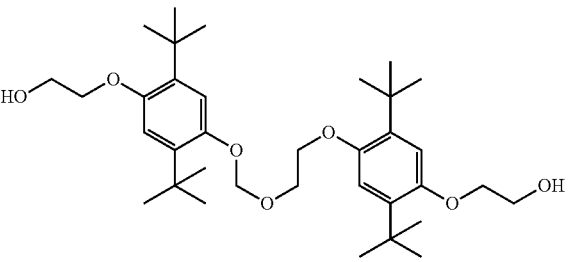

$C_{36}H_{58}O_7$
Mol. Wt.: 602.84

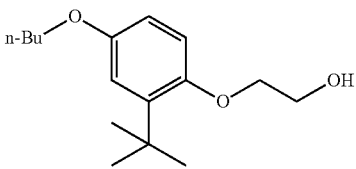

$C_{16}H_{26}O_3$
Mol. Wt.: 266.38

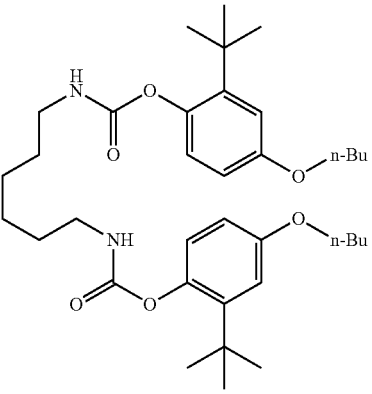

$C_{36}H_{56}N_2O_6$
Mol. Wt.: 612.84

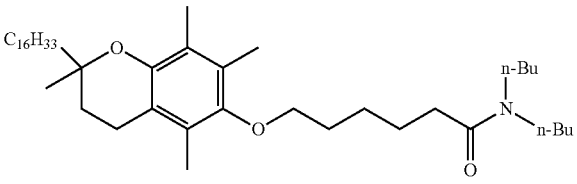

$C_{43}H_{77}NO_3$
Mol. Wt.: 656.08

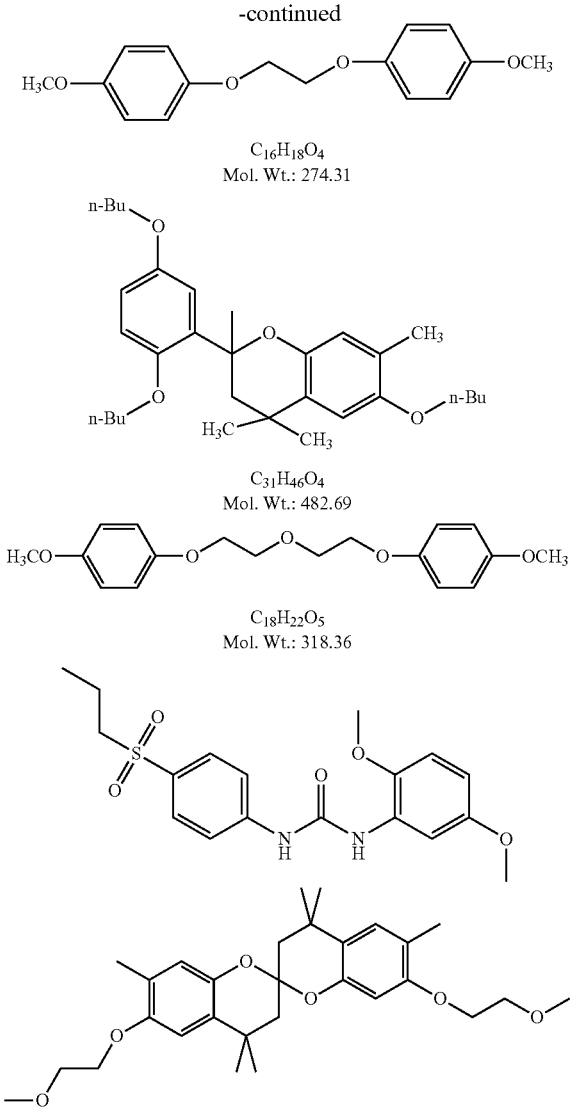

The content of the aromatic polyether-based compound is preferably 0.1 to 50 parts by mass, more preferably 0.5 to 30 parts by mass, still more preferably 1 to 20 parts by mass, and particularly preferably 5 to 20 parts by mass, with respect to 100 parts by mass of the polymerizable liquid crystal compound included in the polymerizable liquid crystal composition of the embodiment of the present invention. By adjusting the content of the aromatic polyether-based compound to be within the range, the light fastness of the optically anisotropic film is further improved.

The aromatic polyether-based compounds may be used alone or in combination of two or more kinds thereof. In a case where two or more kinds of the aromatic polyether-based compounds are used in combination, the total amount thereof is preferably within the range.

[Polymerization Initiator]

The polymerizable liquid crystal composition of the embodiment of the present invention preferably contains a polymerization initiator.

The polymerization initiator to be used is preferably a photopolymerization initiator capable of initiating a polymerization reaction upon irradiation with ultraviolet rays.

Examples of the photopolymerization initiator include α-carbonyl compounds (described in each of the specifications of U.S. Pat. Nos. 2,367,661A and 2,367,670A), acyloin ethers (described in the specification of U.S. Pat. No. 2,448,828A), α-hydrocarbon-substituted aromatic acyloin compounds (described in the specification of U.S. Pat. No. 2,722,512A), multinuclear quinone compounds (as described in each of the specifications of U.S. Pat. Nos. 3,046,127A and 2,951,758A), combinations of triarylimidazole dimer and p-aminophenyl ketone (as described in the specification of U.S. Pat. No. 3,549,367A), acridine and phenazine compounds (described in each of the specifications of JP1985-105667A (JP-S60-105667A) and U.S. Pat. No. 4,239,850A), oxadiazole compounds (described in the specification of U.S. Pat. No. 4,212,970A), and acyl phosphine oxide compounds (described in each of the specifications of JP1988-040799B (JP-S63-040799B), JP1993-029234B (JP-H05-029234B), JP1998-095788A (JP-H10-095788A), and JP1998-029997A (JP-H10-029997A)).

Specific examples of the photopolymerization initiator include Irgacure series (for example, Irgacure 651, Irgacure 754, Irgacure 184, Irgacure 2959, Irgacure 907, Irgacure 369, Irgacure 379, Irgacure 819, and Irgacure OXE-01), available from BASF, Darocure series (for example, Darocure TPO and Darocure 1173), Quantacure PDO, and Ezacure series (for example, Ezacure TZM, Ezacure TZT, and Ezacure KTO46) available from Lamberti.

In a case where the polymerization initiator is contained, the content of the polymerization initiator is preferably 0.5 to 10 parts by mass, and more preferably 1 to 10 parts by mass, with respect to 100 parts by mass of the polymerizable liquid crystal compound included in the polymerizable liquid crystal composition of the embodiment of the present invention.

The polymerization initiators may be used alone or in combination of two or more kinds thereof. In a case where two or more kinds of the polymerization initiators are used in combination, the total amount thereof is preferably within the range.

[Solvent]

The polymerizable liquid crystal composition of the embodiment of the present invention preferably contains a solvent from the viewpoint of workability for forming an optically anisotropic film, and the like.

Specific examples of the solvent include ketones (for example, acetone, 2-butanone, methyl isobutyl ketone, and cyclohexanone), ethers (for example, dioxane and tetrahydrofuran), aliphatic hydrocarbons (for example, hexane), alicyclic hydrocarbons (for example, cyclohexane), aromatic hydrocarbons (for example, toluene, xylene, and trimethylbenzene), halogenated carbons (for example, dichloromethane, dichloroethane, dichlorobenzene, and chlorotoluene), esters (for example, methyl acetate, ethyl acetate, and butyl acetate), water, alcohols (for example, ethanol, isopropanol, butanol, and cyclohexanol), cellosolves (for example, methyl cellosolve and ethyl cellosolve), cellosolve acetates, sulfoxides (for example, dimethyl sulfoxide), and amides (for example, dimethylformamide and dimethylacetamide), and these may be used alone or in combination of two or more kinds thereof.

[Other Components]

The polymerizable liquid crystal composition of the embodiment of the present invention may contain other components than the above components, and examples of such other components include an antioxidant (for example, a phenol-based antioxidant), a liquid crystal compound other than the above liquid crystal compounds, an air interface alignment agent (leveling agent), a surfactants, a tilt angle control agent, an alignment aid, a plasticizer, and a cross-linking agent.

[Optically Anisotropic Film]

An optically anisotropic film of an embodiment of the present invention is an optically anisotropic film obtained by polymerization of the polymerizable liquid crystal composition.

In the present invention, examples of the method for forming the optically anisotropic film include a method in which the polymerizable liquid crystal composition containing the polymerizable liquid crystal compound, the aromatic polyether-based compound, the polymerization initiator, the solvent, and the like as described above is used to form a desired alignment state and then fixed by polymerization.

Here, the polymerization condition is not particularly limited, but in the polymerization by irradiation with light, ultraviolet rays are preferably used. The irradiation dose is preferably 10 mJ/cm$^2$ to 50 J/cm$^2$, more preferably 20 mJ/cm$^2$ to 5 J/cm$^2$, still more preferably 30 mJ/cm$^2$ to 3 J/cm$^2$, and particularly preferably 50 to 1,000 mJ/cm$^2$. In addition, the polymerization may be carried out under a heating condition in order to accelerate the polymerization reaction.

Moreover, in the present invention, the optically anisotropic film can be formed on an optional support in the optical film of an embodiment of the present invention which will be described later or a polarizer in a polarizing plate of an embodiment of the present invention which will be described later.

[Optical Film]

The optical film of the embodiment of the present invention is an optical film having the optically anisotropic film of the embodiment of the present invention.

Figure 1B:
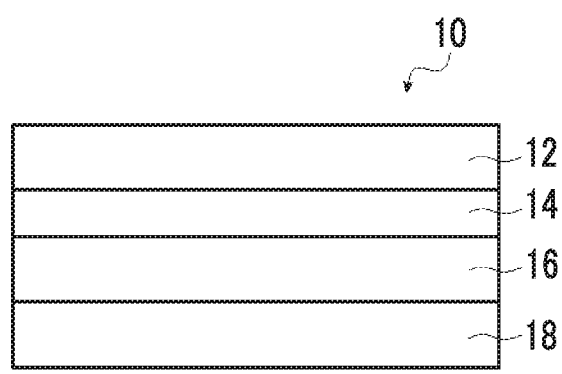
FIG. 1B is a schematic cross-sectional view showing an example of an optical film of the embodiment of the present invention.
Figure 1C:
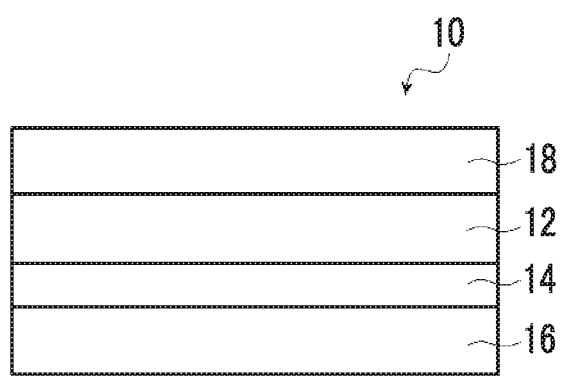
FIG. 1C is a schematic cross-sectional view showing an example of an optical film of the embodiment of the present invention.

FIG. 1A, FIG. 1B, and FIG. 1C (these drawings are hereinafter simply abbreviated as "FIG. 1" unless it is necessary that they are particularly distinguished from each other) are each a cross-sectional view schematically showing an example of the optical film of the embodiment of the present invention.

Furthermore, FIG. 1 is a schematic view, and the thicknesses relationship, the positional relationship, and the like among the respective layers do not necessarily coincide with actual ones. Any of the support, the alignment film and the hard coat layer shown in FIG. 1 are both an optional constitutional member.

An optical film 10 shown in FIG. 1 has a support 16, an alignment film 14, and an optically anisotropic film 12 in this order.

In addition, the optical film 10 may have a hard coat layer 18 on the side of the support 16 opposite to the side on which the alignment film 14 is provided as shown in FIG. 1B, and may have the hard coat layer 18 on the side of the optically anisotropic film 12 opposite to the side on which the alignment film 14 is provided as shown in FIG. 1C.

Hereinafter, various members used for the optical film of the embodiment of the present invention will be described in detail.

[Optically Anisotropic Film]

The optically anisotropic film contained in the optical film of the embodiment of the present invention is the above-mentioned optically anisotropic film of the embodiment of the present invention.

In the optical film of the embodiment of the present invention, the thickness of the optically anisotropic film is not particularly limited, but is preferably 0.1 to 10 μm, and more preferably 0.5 to 5 μm.

In the optical film of the embodiment of the present invention, it is preferable that the above-mentioned optically anisotropic film of the embodiment of the present invention is a positive A plate or a positive C plate from the viewpoint of optical designs.

Here, the A plate encompasses two kinds of plates, that is, a positive A plate and a negative A plate, and in a case where a refractive index in the slow axis direction in the film plane (a direction in which the refractive index becomes a maximum in the plane) is represented by nx, a refractive index in the direction in-plane orthogonal to the in-plane slow axis is represented by ny, and a refractive index in the thickness direction is represented by nz, the positive A plate satisfies the relationship of Formula (A1) and the negative A plate satisfies the relationship of Formula (A2). In addition, in the positive A plate, Rth represents a positive value, and in the negative A plate, Rth represents a negative value.

$$nx>ny\approx nz \quad \text{Formula (A1)}$$

$$ny<nx\approx nz \quad \text{Formula (A2)}$$

Furthermore, "≈" encompasses a case where the both are completely the same as well as a case where the both are substantially the same. The expression, "substantially the same" has the following meanings: for example, a case where (ny−nz)×d (in which d is the thickness of a film) is −10 to 10 nm, and preferably −5 to 5 nm is also included "ny≈nz", and a case where (nx−nz)×d is −10 to 10 nm, and preferably −5 to 5 nm is also included in "nx≈nz".

In addition, the C plate encompasses two kinds of plates, that is, a positive C plate and a negative C plate, the positive C plate satisfies the relationship of Formula (C1), and the negative C plate satisfies the relationship of Formula (C2). In addition, in the positive C plate, Rth represents a negative value, and in the negative C plate, Rth represents a positive value.

$$nz>nx\approx ny \quad \text{Formula (C1)}$$

$$nz<nx\approx ny \quad \text{Formula (C2)}$$

Furthermore, "≈" encompasses a case where the both are completely the same as well as a case where the both are substantially the same. The expression, "substantially the same" has the following meanings: for example, a case where (nx−ny)×d (in which d is the thickness of a film) is 0 to 10 nm, and preferably 0 to 5 nm is also included "nx≈ny".

From the viewpoint of optical designs, it is preferable that the optical film of the embodiment of the present invention is an optical film having the above-mentioned two or more layers of the optically anisotropic films of the embodiment of the present invention, in which at least one of the layers is a positive A plate and at least one of the other layers is a positive C plate.

[Support]

The optical film of the embodiment of the present invention may have a support as a base material for forming an optically anisotropic film as described above.

Such a support is preferably transparent, and specifically, the support preferably has a light transmittance of 80% or more.

Examples of such a support include a glass substrate and a polymer film. Examples of the material for the polymer film include cellulose-based polymers; acrylic polymers having acrylic acid ester polymers such as polymethyl methacrylate and a lactone ring-containing polymer; thermoplastic norbornene-based polymers; polycarbonate-based polymers; polyester-based polymers such as polyethylene terephthalate and polyethylene naphthalate; styrene-based polymers such as polystyrene and an acrylonitrile-styrene copolymer (AS resin); polyolefin-based polymers such as polyethylene, polypropylene, and an ethylene-propylene copolymer; vinyl chloride-based polymers; amide-based polymers such as nylon and aromatic polyamide; imide-based polymers; sulfone-based polymers; polyether sulfone-based polymers; polyether ether ketone-based polymers; polyphenylene sulfide-based polymers; vinylidene chloride-based polymers; vinyl alcohol-based polymers; vinyl butyral-based polymers; arylate-based polymers; polyoxymethylene-based polymers; epoxy-based polymers; and polymers containing a mixture of these polymers.

In addition, in an aspect, the polarizer which will be described later may also function as such a support.

In the present invention, the thickness of the support is not particularly limited, but is preferably 5 to 60 μm, and more preferably 5 to 30 μm.

[Alignment Film]

In a case where the optical film of the embodiment of the present invention has the above-mentioned optional support, it is preferable that the optical film has an alignment film between the support and the optically anisotropic film. Further, in an aspect, the above-mentioned support may also function as an alignment film.

The alignment film generally has a polymer as a main component. The materials for the polymer material for an alignment film are described in many documents, and many commercially available products can be used.

The polymer material used in the present invention is preferably a polyvinyl alcohol or a polyimide, or a derivative thereof. Particularly, a modified or non-modified polyvinyl alcohol is preferable.

Examples of the alignment film that can be used in the present invention include the alignment films described in Line 24 on Page 43 to Line 8 on Page 49 of WO01/088574A; the modified polyvinyl alcohols described in paragraphs [0071] to [0095] of JP3907735B; and the liquid crystal alignment film formed by a liquid crystal aligning agent described in JP2012-155308A.

In the present invention, for a reason that deterioration in the surface state can be prevented by avoiding a contact with the surface of the alignment film upon formation of the alignment film, an optical alignment film is also preferably used as the alignment film.

The optical alignment film is not particularly limited, but the polymer materials such as a polyamide compound and a polyimide compound described in paragraphs [0024] to of WO2005/096041A; the liquid crystal alignment film formed by a liquid crystal aligning agent having an optical aligned group described in JP2012-155308A; LPP-JP265CP, trade name, manufactured by Rolic technologies Ltd.; or the like can be used.

In addition, in the present invention, the thickness of the alignment film is not particularly limited, but from the viewpoint of forming an optically anisotropic film having a uniform film thickness by alleviating the surface roughness present on the support, the thickness is preferably 0.01 to 10 μm, more preferably 0.01 to 1 μm, and still more preferably 0.01 to 0.5 μm.

[Hard Coat Layer]

The optical film of the embodiment of the present invention preferably has a hard coat layer in order to impart film physical strength. Specifically, the hard coat layer may be provided on the side of the support opposite to the side on which the alignment film is provided (refer to FIG. 1B) or may be provided on the side of the optically anisotropic film opposite to the side on which the alignment film is provided (refer to FIG. 1C).

As the hard coat layer, those described in paragraphs [0190] to [0196] of JP2009-098658A can be used.

[Other Optically Anisotropic Films]

The optical film of the embodiment of the present invention may have other optically anisotropic films, in addition to the optically anisotropic film of the embodiment of the present invention.

That is, the optical film of the embodiment of the present invention may have a laminated structure having the optically anisotropic film of the embodiment of the present invention and other optically anisotropic films.

Examples of such other optically anisotropic films include optically anisotropic films obtained using the above-mentioned polymerizable liquid crystal compound, and are not particularly limited.

Here, the liquid crystal compounds are generally classified into a rod-like type and a disk-like type according to the shape thereof. Further, each includes a low molecular type and a high molecular type. The term "high molecular" generally refers to having a degree of polymerization of 100 or more (Polymer Physics-Phase Transition Dynamics, by Masao Doi, page. 2, published by Iwanami Shoten, Publishers, 1992). In the present invention, any type of liquid crystal compound can be used, but a rod-like liquid crystal compound or a discotic liquid crystal compound (disk-like liquid crystal compound) is preferably used. Two or more kinds of rod-like liquid crystal compounds, two or more kinds of disk-like liquid crystal compounds, or a mixture of the rod-like liquid crystal compound and the disk-like liquid crystal compound may be used. In order to fix the above-mentioned liquid crystal compound, it is more preferable that the liquid crystal compound is formed of a rod-like liquid crystal compound or disk-like liquid crystal compound having a polymerizable group, and it is still more preferable that the liquid crystal compound has two or more polymerizable groups in one molecule. In the case of a mixture of two or more kinds of the liquid crystal compounds, at least one kind of the liquid crystal compound preferably has two or more polymerizable groups in one molecule.

As the rod-like liquid crystal compound, for example, the rod-like liquid crystal compounds described in claim 1 of JP1999-513019A (JP-H11-513019A) or paragraphs [0026] to [0098] of JP2005-289980A can be preferably used, and as the discotic liquid crystal compounds, for example, the discotic liquid crystal compounds described in paragraphs [0020] to [0067] of JP2007-108732A and paragraphs [0013] to [0108] of JP2010-244038A can be preferably used, but the liquid crystal compounds are not limited thereto.

[Ultraviolet Absorber]

The optical film of the embodiment of the present invention preferably includes an ultraviolet absorber in consideration of the effect of external light (particularly ultraviolet rays), and more preferably includes an ultraviolet absorber on a support.

As the ultraviolet absorber, any known ultraviolet absorbers that can express ultraviolet absorptivity can be used. Among such ultraviolet absorbers, a benzotriazole-based or hydroxyphenyltriazine-based ultraviolet absorber is preferable since that has high ultraviolet absorptivity and can be used to obtain ultraviolet absorptivity (ultraviolet shielding ability) for use in an electron image display device. Further, a combination of two or more kinds of ultraviolet absorbers having different maximum absorption wavelengths can be used in order to extend the absorption range of ultraviolet rays.

[Polarizing Plate]

A polarizing plate of an embodiment of the present invention has the above-mentioned optical film of the embodiment of the present invention and a polarizer.

[Polarizer]

A polarizer contained in a polarizing plate of an embodiment of the present invention is not particularly limited as long as it is a member having a function of converting light into specific linearly polarized light, and an absorptive type polarizer and a reflective type polarizer, which are known in the related art, can be used.

An iodine-based polarizer, a dye-based polarizer using a dichroic dye, a polyene-based polarizer, or the like is used as the absorptive type polarizer. The iodine-based polarizer and the dye-based polarizer encompass a coating type polarizer and a stretching type polarizer, any of which can be applied, but a polarizer which is manufactured by allowing polyvinyl alcohol to adsorb iodine or a dichroic dye and performing stretching is preferable.

In addition, examples of a method of obtaining a polarizer by performing stretching and dyeing in a state of a laminated film in which a polyvinyl alcohol layer is formed on a basic material include the methods disclosed in JP5048120B, JP5143918B, JP4691205B, JP4751481B, and JP4751486B, and known technologies related to these polarizers can also be preferably used.

A polarizer in which thin films having different birefringence are laminated, a wire grid type polarizer, a polarizer in which a cholesteric liquid crystal having a selective reflection range and a ¼ wavelength plate are combined, or the like is used as the reflective type polarizer.

Among these, a polarizer including a polyvinyl alcohol-based resin (a polymer including —$CH_2$—CHOH— as a repeating unit, in particular, at least one selected from the group consisting of a polyvinyl alcohol and an ethylene-vinyl alcohol copolymer) is preferable from the viewpoint that the adhesiveness is more excellent.

In the present invention, the thickness of the polarizer is not particularly limited, but is preferably 3 μm to 60 μm, more preferably 5 μm to 30 μm, and still more preferably 5 μm to 15 μm.

[Adhesive Layer]

The polarizing plate of the embodiment of the present invention may have an adhesive layer arranged between the optically anisotropic film in the optical film of the embodiment of the present invention and the polarizer.

The adhesive layer used for the lamination of the optically anisotropic film and the polarizer represents, for example, a substance in which a ratio (tan δ=G"/G') between a storage elastic modulus G' and a loss elastic modulus G", each measured with a dynamic viscoelastometer, is 0.001 to 1.5, and examples thereof include a so-called adhesive or readily creepable substance. Examples of the adhesive that can be used in the present invention include a polyvinyl alcohol-based adhesive may be used, but the adhesive is not limited thereto.

[Image Display Device]

An image display device of an embodiment of the present invention is an image display device having the optical film of the embodiment of the present invention or the polarizing plate of the embodiment of the present invention.

The display element used in the image display device of the embodiment of the present invention is not particularly limited, and examples thereof include a liquid crystal cell, an organic electroluminescent (hereinafter abbreviated as "EL") display panel, and a plasma display panel.

Among those, the liquid crystal cell and the organic EL display panel are preferable, and the liquid crystal cell is more preferable. That is, as the image display device of the embodiment of the present invention, a liquid crystal display device using a liquid crystal cell as a display element or an organic EL display device using an organic EL display panel as a display element is preferable, and the liquid crystal display device is more preferable.

[Liquid Crystal Display Device]

A liquid crystal display device that is an example of the image display device of the embodiment of the present invention is a liquid crystal display device having the above-mentioned polarizing plate of the embodiment of the present invention and a liquid crystal cell.

Furthermore, in the present invention, it is preferable that the polarizing plate of the embodiment of the present invention is used as the polarizing plate of the front side, out of the polarizing plates provided on the both sides of the liquid crystal cell, and it is more preferable that the polarizing plate of the embodiment of the present invention is used as the polarizing plates on the front and rear sides.

Hereinafter, the liquid crystal cell constituting the liquid crystal display device will be described in detail.

<Liquid Crystal Cell>

A liquid crystal cell for use in the liquid crystal display device is preferably in a vertical alignment (VA) mode, an optically compensated bend (OCB) mode, an in-plane-switching (IPS) mode, or a twisted nematic (TN) mode, but is not limited thereto.

In the liquid crystal cell in a TN mode, rod-like liquid crystal molecules are aligned substantially horizontally in a case where no voltage is applied and are further aligned in a twisted manner in a range of 60° to 120°. The liquid crystal cell in a TN mode is most often used in a color TFT liquid crystal display device and described in many literatures.

In the liquid crystal cell in a VA mode, rod-like liquid crystal molecules are aligned substantially vertically in a case where no voltage is applied. Examples of the liquid crystal cells in a VA mode include (1) a narrowly defined VA mode liquid crystal cell (described in JP1990-176625A (JP-H02-176625A)) in which rod-like liquid crystal molecules are aligned substantially vertically in a case where no voltage is applied and are aligned substantially horizontally in a case where a voltage is applied, (2) a multi-domain VA mode (MVA mode) liquid crystal cell for enlarging the viewing angle (SID97, described in Digest of tech. Papers (Proceedings) 28 (1997) 845), (3) a liquid crystal cell in a mode (n-ASM mode) in which rod-like liquid crystal molecules are aligned substantially vertically in a case where no voltage is applied and are aligned in twisted multi-domain alignment in a case where a voltage is applied (Proceedings of Japanese Liquid Crystal Conference, 58 and 59 (1998)), and (4) a liquid crystal cell in a SURVIVAL mode (presented in LCD International 98). Further, the liquid crystal cell may be of any of a patterned vertical alignment (PVA) type, an optical alignment type, and a polymer-sustained alignment (PSA) type. Details of these modes are described in detail in JP2006-215326A and JP2008-538819A.

In the liquid crystal cell in an IPS mode, rod-like liquid crystal molecules are aligned substantially parallel with respect to a substrate and application of an electric field parallel to the substrate surface causes the rod-like liquid crystal molecules to respond planarly. The IPS mode displays black in a case where no electric field is applied and a pair of upper and lower polarizing plates have absorption axes which are orthogonal to each other. A method of improving the viewing angle by reducing light leakage during black display in an oblique direction using an optical compensation sheet is disclosed in JP1998-054982A (JP-H10-054982A), JP1999-202323A (JP-H11-202323A), JP1997-292522A (JP-H09-292522A), JP1999-133408A (JP-H11-133408A), JP1999-305217A (JP-H11-305217A), JP1998-307291A (JP-H10-307291 A), and the like.

[Organic EL Display Device]

Suitable examples of the organic EL display device which is an example of the image display device of the embodiment of the present invention include an aspect which includes, from the visible side, the polarizing plate of the embodiment of the present invention, a plate having a λ/4 function (hereinafter referred to also as "λ/4 plate") and an organic EL display panel in this order.

Here, an expression, a "plate having a λ/4 function" refers to a plate having a function of converting linearly polarized light at a specific wavelength into circularly polarized light (or circularly polarized light into linearly polarized light). Specific examples of an aspect in which a λ/4 plate is of a single layer structure include a stretched polymer film, and a retardation film in which an optically anisotropic film having a λ/4 function is provided on a support, and specific examples of an embodiment in which a λ4 plate is of a multilayer structure include a broadband λ/4 plate in which the λ4 plate and a λ/2 plate are laminated on each other.

Furthermore, the organic EL display panel is a display panel configured using an organic EL device in which an organic light emitting layer (organic electroluminescent layer) is sandwiched between electrodes (between a cathode and an anode). The configuration of the organic EL display panel is not particularly limited but any known configuration is adopted.

The image display device of the embodiment of the present invention is preferably an organic EL display device including an organic EL display panel and a circularly polarizing plate arranged on the organic EL display panel.

In particular, in the present invention, an aspect in which the circularly polarizing plate includes a polarizer and the above-mentioned optical film of the embodiment of the present invention is more preferable, and an aspect in which the circularly polarizing plate has a polarizer and an optical film having two or more layers of the optically anisotropic films, in which at least one of the layers is a positive A plate and at least one of the other layers is a positive C plate, is still more preferable.

EXAMPLES

Hereinafter, the present invention will be described in more detail with reference to Examples. The materials, the amounts of materials used, the proportions, the treatment details, the treatment procedure, and the like shown in Examples below may be modified, as appropriate, as long as the modifications do not depart from the spirit of the present invention. Therefore, the scope of the present invention should not be construed as being limited to Examples shown below.

[Polymerizable Liquid Crystal Compound]

In the preparation of polymerizable liquid crystal compositions, the following polymerizable liquid crystal compounds 1 to 7 were prepared.

<Synthesis of Polymerizable Liquid Crystal Compound 1 (Reverse Dispersion Liquid Crystal 1)>

According to the following scheme, compounds represented by Formulae A to C (hereinafter also simply referred to as compounds A to C, respectively) were synthesized.

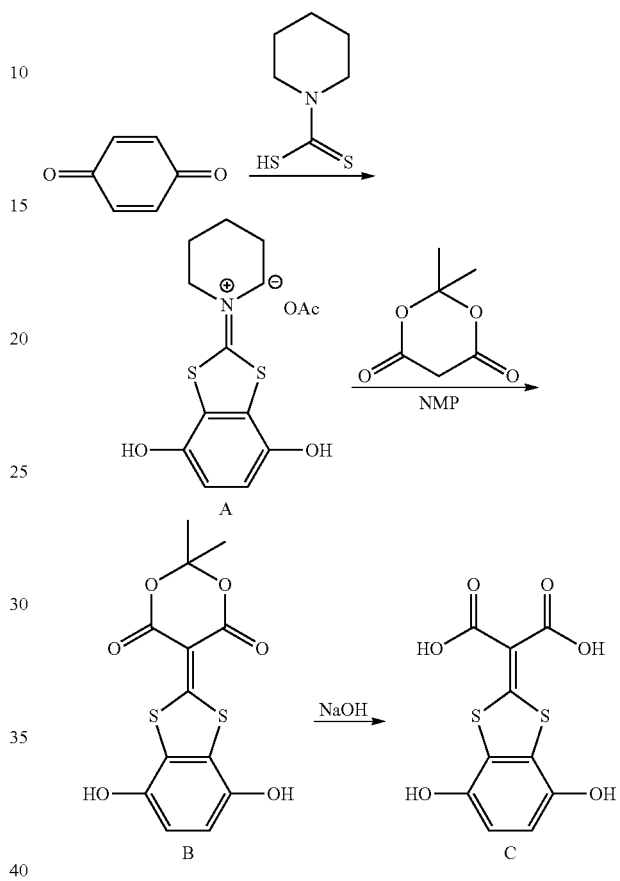

(Synthesis of Compound A)

The synthesis of the compound A was performed by the method described in "Journal of Organic Chemistry" (2004); 69(6); p. 2164-2177.

(Synthesis of Compound B)

30.0 g (0.0916 mol) of the compound A, 19.8 g (0.137 mol) of Meldrum's acid, and 200 mL of N-methyl-2-pyrrolidone (NMP) were mixed and stirred at 55° C. for 2 hours.

Thereafter, the mixture was cooled to room temperature, 200 mL of water was added to the mixture, and the precipitated crystal was filtered.

The obtained crystal was washed with a mixed solution of water and NMP at 1:1 to obtain 28.4 g (0.0870 mol) of a compound B (yield: 95%).

(Compound C)

51.5 g (0.158 mol) of the compound B and 315 mL of THF were mixed, and 395 mL (0.789 mol) of a 2 M aqueous sodium hydroxide solution was added dropwise thereto under ice-cooling.

Subsequently, the mixture was warmed to room temperature and stirred for 2 hours, and then 263 mL (0.789 mol) 3 N aqueous hydrochloric acid was added dropwise thereto under ice-cooling.

Subsequently, 300 mL of water and 180 mL of isopropyl alcohol (IPA) were added thereto and the precipitated solid was filtered.

The obtained solid was stirred with acetonitrile, suspended, and then filtered to obtain 25 g (0.0868 mol) of a compound C (yield: 55%).

Subsequently, according to the following scheme, a compound D represented by Formula D was synthesized.

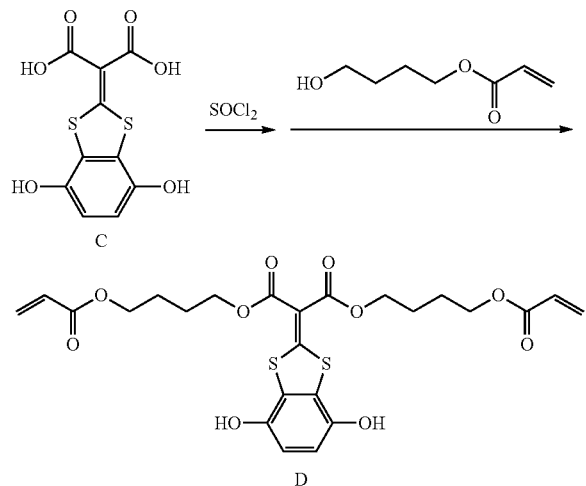

(Synthesis of Compound D)

50 g (0.175 mol) of the compound C, BHT (1.9 g, 8.74 mmol), 300 mL of THF, and 150 mL of N,N-dimethylacetamide (DMAc) were mixed, and 87.3 g (0.734 mol) of thionyl chloride was added dropwise thereto under ice-cooling.

Subsequently, the mixture was stirred for 2 hours under ice-cooling, and then 126 g (0.874 mol) of 4-hydroxybutylacrylic acid ester was added dropwise thereto.

Subsequently, the mixture was warmed to room temperature, the mixture was stirred for 2 hours and then extracted by the addition of 400 mL of 5% saline, 100 mL of ethyl acetate, and 200 mL of tetrahydrofuran (THF).

The organic layer was washed twice with 200 mL of 10% saline, then the organic layer was dried over magnesium sulfate, and the solvent was distilled off under reduced pressure. The obtained crude product was stirred with acetonitrile, suspended, and filtered to obtain 57 g (0.107 mol) of a compound D (yield: 61%).

(Synthesis of Reverse Dispersion Liquid Crystal 1)

According to the following scheme, 12.7 g (0.107 mmol) of thionyl chloride was added to a solution of 22.1 g (0.0928 mol) of a compound E represented by Formula E in 40 ml of toluene, and a catalytic amount of N,N-dimethylformamide was added thereto. The mixture was warmed to 65° C. as it was and then stirred for 2 hours, and the solvent was distilled off.

Subsequently, 25 g (0.0464 mol) of the compound D, BHT (0.51 g, 2.32 mmol), and THF (125 mL) were added to the mixture, and 10.3 g (0.102 mol) of triethylamine was added dropwise thereto under ice-cooling.

Subsequently, the mixture was warmed to room temperature, stirred for 2 hours, and then extracted by the addition of 100 ml of 1 M aqueous hydrochloric acid and 40 ml of ethyl acetate.

The organic layer was washed with 10% saline, then 400 ml of methanol was added to the organic layer, and the precipitated solid was filtered to obtain 38 g (0.0389 mol) of a reverse dispersion liquid crystal 1 represented by Formula 1 (yield: 84%).

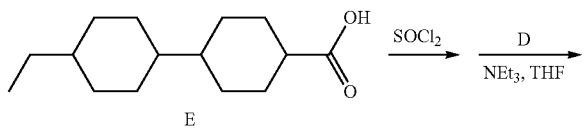

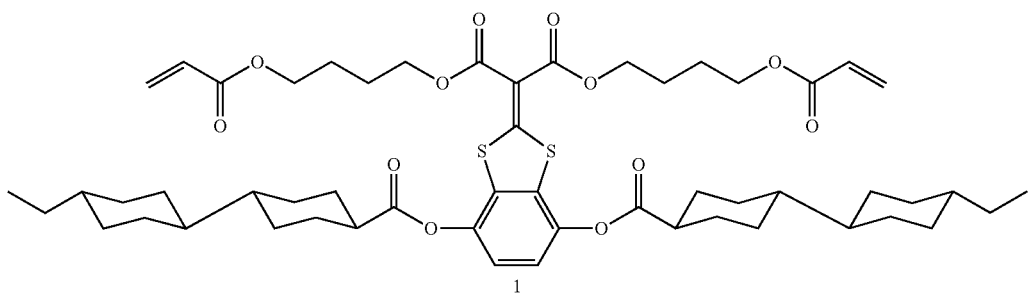

<Synthesis of Polymerizable Liquid Crystal Compound 2 (Reverse Dispersion Liquid Crystal 2)>

According to the method described in paragraphs [0462] to [0477] of JP2011-207765A, a reverse dispersion liquid crystal 2 represented by Formula 2 was synthesized.

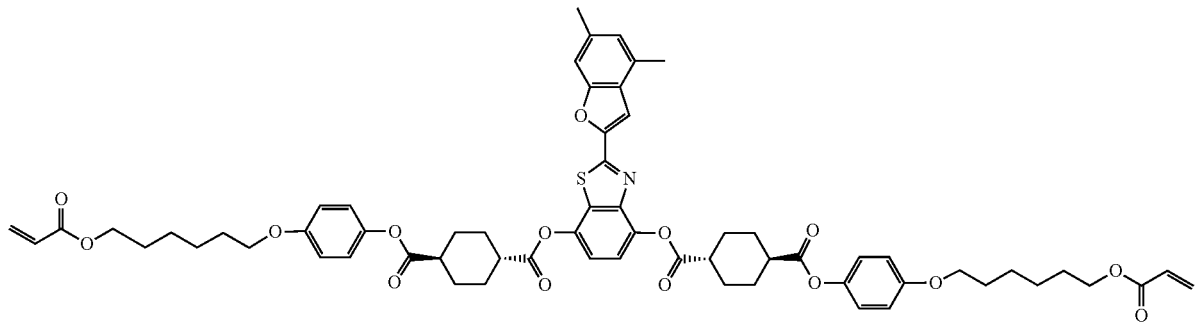

<Synthesis of Polymerizable Liquid Crystal Compound 3 (Reverse Dispersion Liquid Crystal 3)>

According to the method described in paragraphs [0205] to [0217] of WO2014/010325A, a reverse dispersion liquid crystal 3 represented by Formula 3 was synthesized.

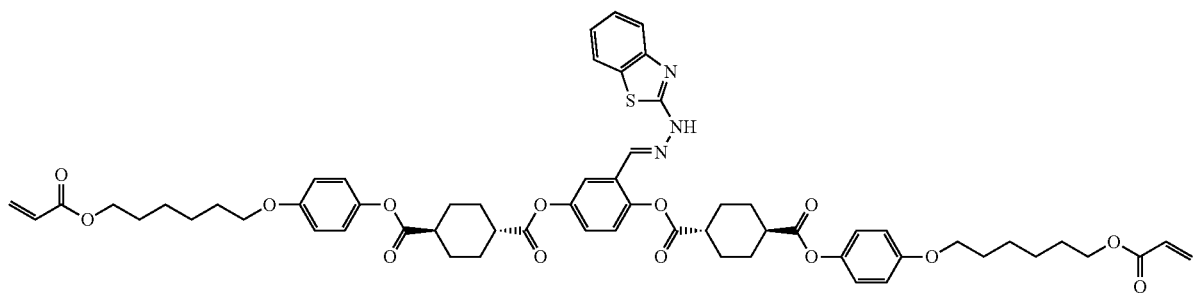

<Synthesis of Polymerizable Liquid Crystal Compound 4 (Forward Dispersion Liquid Crystal 1)>

In accordance with the method described in Reference 1 (Makromol. Chem. 190, page 59 (1991)), a forward dispersion liquid crystal 1 represented by the following formula was synthesized.

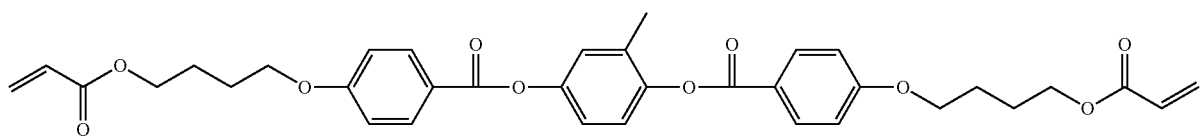 [SMILES: C=CC(=O)OCCCCOc1ccc(C(=O)Oc2ccc(OC(=O)c3ccc(OCCCCOC(=O)C=C)cc3)c(C)c2)cc1]

<Synthesis of Polymerizable Liquid Crystal Compound 5 (Reverse Dispersion Liquid Crystal 4)>

A side-chain carboxylic acid F represented by Formula F and a phenol G represented by Formula C were synthesized, and a reverse dispersion liquid crystal 4 represented by Formula 5 was synthesized by the following route.

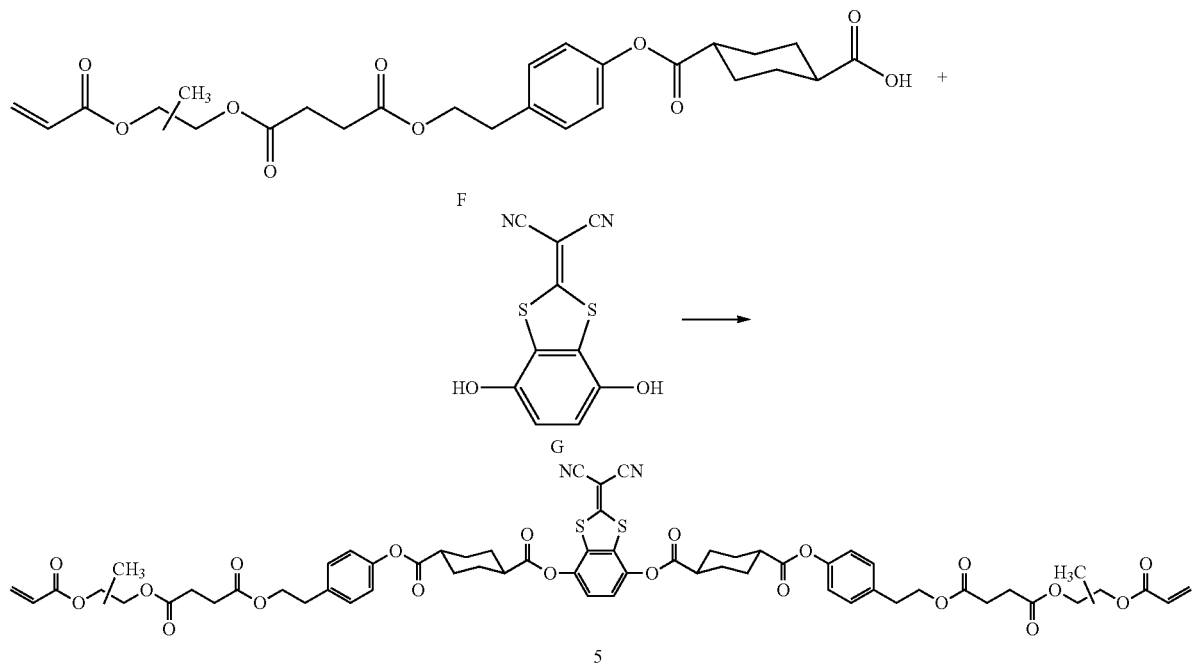

(Synthesis of Side-Chain Carboxylic Acid F)

According to the compound (I-4C) described in JP2016-081035A, a side-chain carboxylic acid F of the reverse dispersion liquid crystal 4 was synthesized.

$^1$H-NMR (Nuclear Magnetic Resonance) of the obtained side-chain carboxylic acid F is shown below.

$^1$H-NMR (solvent: CDCl$_3$) δ (ppm):

[Major Isomer]

1.27 (d, 3H), 1.45-1.73 (m, 4H), 2.10-2.32 (m, 4H), 2.32-2.45 (m, 1H), 2.48-2.70 (m, 1H), 2.62 (s, 4H), 2.93 (t, 2H), 4.15 (dd, 1H), 4.25 (dd, 1H), 4.29 (t, 2H), 5.20 (m, 1H), 5.85 (dd, 1H), 6.13 (dd, 1H), 6.42 (dd, 1H), 6.95-7.06 (m, 2H), 7.16-7.25 (m, 2H)

[Minor Isomer]

1.29 (d, 3H), 1.45-1.73 (m, 4H), 2.10-2.32 (m, 4H), 2.32-2.45 (m, 1H), 2.48-2.70 (m, 1H), 2.62 (s, 4H), 2.93 (t, 2H), 4.13 (dd, 1H), 4.22 (dd, 1H), 4.29 (t, 2H), 5.20 (m, 1H), 5.84 (dd, 1H), 6.11 (dd, 1H), 6.41 (dd, 1H), 6.95-7.06 (m, 2H), 7.16-7.25 (m, 2H)

(Synthesis of Phenol G)

The synthesis of the phenol G can be performed with reference to the method described in Justus Liebigs Annalen der Chemie, 726, 103-109 (1969).

In a nitrogen stream, 21.79 g (334 mmol) of potassium hydroxide at a content of 86% was dissolved in 70 ml of isopropyl alcohol and 85 ml of water. To this solution was added a solution obtained by dissolving 11.03 g (167 mmol) of malononitrile in 12 ml of isopropyl alcohol at an inner temperature of 5° C. or lower while stirring the mixture under ice-cooling.

Subsequently, 13.35 g (175 mmol) of carbon disulfide was added dropwise thereto at an inner temperature of 10° C. or lower, and then the mixture was stirred for 30 minutes under ice-cooling. To this reaction liquid was slowly added dropwise a mixed solution of 36.46 g (338 mmol) of 1,4-benzoquinone, 21.96 ml (384 mmol) of acetic acid, and 200 ml of acetone while keeping the inner temperature at 2° C. or lower. The mixture was stirred at the same temperature for 30 minutes and then warmed to 25° C., and 365 ml of water was added thereto.

Subsequently, the precipitated crystal was collected by filtration and washed with 835 ml of water and then with a mixed solution of water/acetone (90 ml/90 ml) to obtain a crude product.

Subsequently, the crude product and 100 ml of THF were mixed and stirred in a nitrogen stream, and warmed to 40° C., and then 150 ml of water was added dropwise thereto at 40° C.

Thereafter, the mixture was cooled to 5° C. to precipitate a crystal, followed by stirring at 5° C. for 1 hour. The precipitated crystal was collected by filtration, washed with a mixed solution of THF/water (40 ml/120 ml), and then dried at 60° C. under reduced pressure to obtain 31.3 g (yield: 75%) of a phenol G as a pale yellow solid.

$^1$H-NMR of the obtained phenol G is shown below.

$^1$H-NMR (DMSO-d$_6$) δ (ppm): 6.80 (s, 2H), 10.51 (s, 2H)

(Synthesis of Reverse Dispersion Liquid Crystal 4)

According to the compound (I-4) described in JP2016-081035A, a reverse dispersion liquid crystal 4 was synthesized.

$^1$H-NMR of the obtained reverse dispersion liquid crystal 4 is shown below.

$^1$H-NMR (solvent: CDCl$_3$) δ (ppm):

[Major Isomer]

1.27 (d, 6H), 1.56-1.79 (m, 8H), 2.22-2.40 (m, 8H), 2.55-2.75 (m, 4H), 2.62 (s, 8H), 2.94 (t, 4H), 4.15 (dd, 2H), 4.25 (dd, 2H), 4.28 (t, 4H), 5.20 (m, 2H), 5.86 (dd, 2H), 6.13 (dd, 2H), 6.43 (dd, 2H), 6.99-7.06 (m, 4H), 7.20-7.25 (m, 4H), 7.32 (s, 2H)

[Minor Isomer]

1.29 (d, 6H), 1.56-1.79 (m, 8H), 2.22-2.40 (m, 8H), 2.55-2.75 (m, 4H), 2.62 (s, 8H), 2.94 (t, 4H), 4.12 (dd, 2H), 4.22 (dd, 2H), 4.28 (t, 4H), 5.20 (m, 2H), 5.84 (dd, 2H), 6.11 (dd, 2H), 6.41 (dd, 2H), 6.99-7.06 (m, 4H), 7.20-7.25 (m, 4H), 7.32 (s, 2H)

<Synthesis of Polymerizable Liquid Crystal Compound 6 (Reverse Dispersion Liquid Crystal 5)>

A side-chain carboxylic acid F represented by Formula F and a phenol H represented by Formula H were synthesized, and a reverse dispersion liquid crystal 5 represented by Formula 6 was synthesized by the following route.

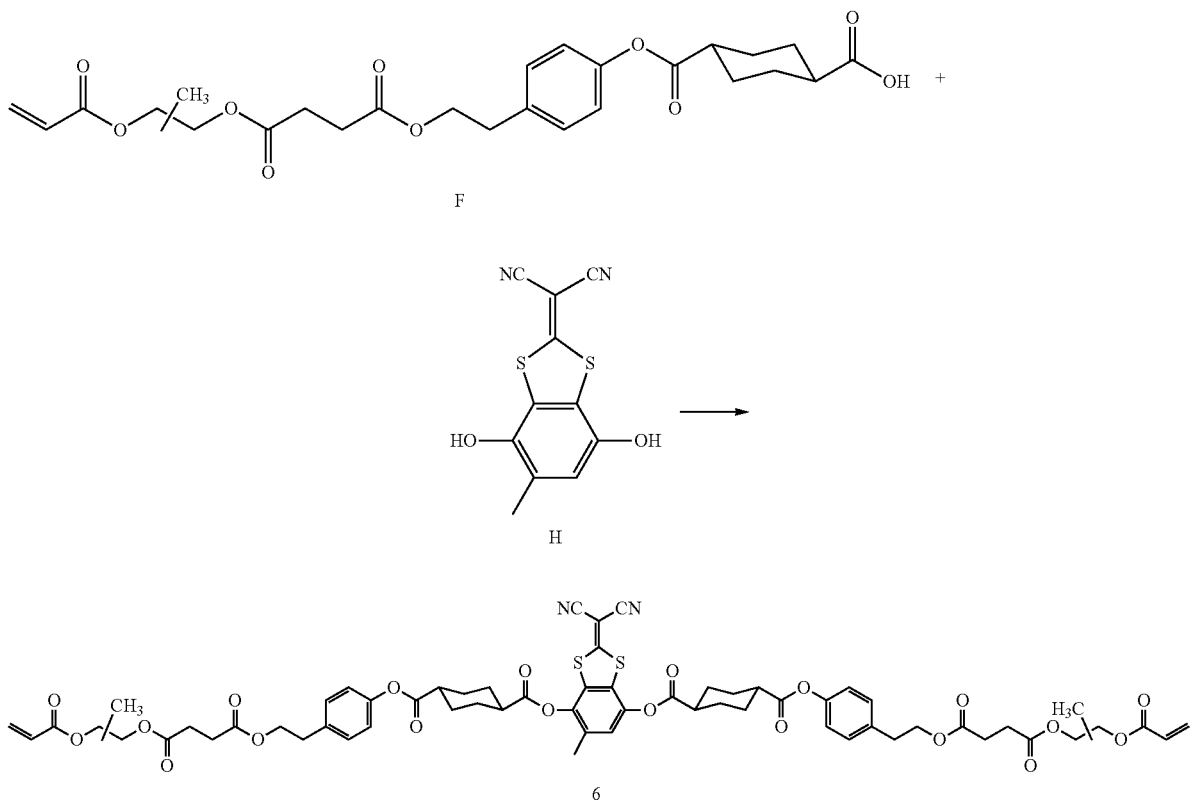

(Synthesis of Phenol H)

In a nitrogen stream, 19.57 g (300 mmol) of potassium hydroxide at a content of 86% was dissolved in 60 ml of isopropyl alcohol and 75 ml of water. To this solution was added a solution obtained by dissolving 9.91 g (150 mmol) of malononitrile in 10.5 ml of isopropyl alcohol at an inner temperature of 5° C. or lower while stirring the mixture under ice-cooling.

Subsequently, 11.42 g (150 mmol) of carbon disulfide was added dropwise thereto at an inner temperature of 10° C. or lower, and then the mixture was stirred for 30 minutes under ice-cooling. Subsequently, 2.57 ml (45 mmol) of acetic acid was added to adjust the pH of the reaction liquid to 6. To this reaction liquid was slowly added dropwise a mixed solution of 36.26 g (298 mmol) of p-toluquinone, 16.98 ml (298 mmol) of acetic acid, and 150 ml of acetone while keeping the inner temperature at 5° C. or lower. The mixture was stirred at the same temperature for 30 minutes and then warmed to 50° C., and 395 ml of water was added thereto.

The mixture was stirred for 30 minutes, then the temperature was lowered to 15° C., and the precipitated crystal was collected by filtration and washed with 790 ml of water to obtain a crude product.

Subsequently, the crude product, 155 ml of acetonitrile, and 155 ml of water were mixed in a nitrogen stream, stirred at room temperature for 1 hour, and then cooled to 5° C., and the mixture was further stirred for 30 minutes. The precipitated crystal was collected by filtration, washed with a mixed solution of acetonitrile/water (50 ml/60 ml) which had been ice-cooled, and then dried at 60° C. under reduced pressure to obtain 32.6 g (yield: 83%) of a phenol H as a yellow solid.

$^1$H-NMR of the obtained phenol H is shown below.

$^1$H-NMR (solvent: DMSO-$d_6$) δ (ppm): 2.19 (s, 3H), 6.71 (s, 1H), 9.60 (br s, 1H), 10.55 (br s, 1H)

(Synthesis of Reverse Dispersion Liquid Crystal 5)

According to the compound (IV-4) described in JP2016-081035A, a reverse dispersion liquid crystal 5 was synthesized.

$^1$H-NMR of the obtained reverse dispersion liquid crystal 5 is shown below.

$^1$H-NMR (solvent: CDCl$_3$) δ (ppm):

[Major Isomer]

1.27 (d, 6H), 1.56-1.79 (m, 8H), 2.22 (s, 3H), 2.22-2.40 (m, 8H), 2.55-2.75 (m, 4H), 2.62 (s, 8H), 2.94 (t, 4H), 4.15 (dd, 2H), 4.25 (dd, 2H), 4.28 (t, 4H), 5.20 (m, 2H), 5.86 (dd, 2H), 6.13 (dd, 2H), 6.43 (dd, 2H), 6.99-7.06 (m, 4H), 7.20-7.25 (m, 4H), 7.25 (s, 1H)

[Minor Isomer]

1.29 (d, 6H), 1.56-1.79 (m, 8H), 2.22 (s, 3H), 2.22-2.40 (m, 8H), 2.55-2.75 (m, 4H), 2.62 (s, 8H), 2.94 (t, 4H), 4.12 (dd, 2H), 4.22 (dd, 2H), 4.28 (t, 4H), 5.20 (m, 2H), 5.84 (dd, 2H), 6.11 (dd, 2H), 6.41 (dd, 2H), 6.99-7.06 (m, 4H), 7.20-7.25 (m, 4H), 7.25 (s, 1H)

<Synthesis of Polymerizable Liquid Crystal Compound 7 (Forward Dispersion Liquid Crystal 2)>

According to the method described in JP6086884B, a forward dispersion liquid crystal 2 represented by the following formula was synthesized.

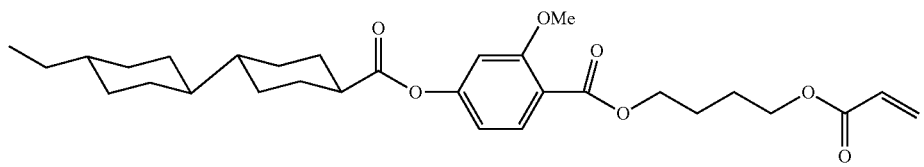 [SMILES: C=CC(=O)OCCCCOC(=O)c1ccc(OC(=O)C2CCC(C3CCC(CC)CC3)CC2)cc1OC]

<Measurement of pKa>

A pKa (first acid dissociation constant) of the compound (for example, the compound D in the polymerizable liquid crystal compound 1) used for the formation of a core portion of each polymerizable liquid crystal compound was determined by computation using the above-mentioned software package 1. The pKa is shown in Table 1.

[Additives]

In the preparation of the polymerizable liquid crystal composition, the following various additives were prepared.

20 mL of a dimethylacetamide solvent was put into a 300-mL flask, DL-α-tocopherol (4.31 g, 10 mmol), a halogen compound (a compound represented by Formula (HA-1), 3.37 g, 11 mmol), and 28% sodium methoxide (2.12 g, 11 mmol) as a base were added thereto, and the mixture was stirred at an inner temperature of 80° C. for 3 hours. Thereafter, water was added thereto, and the mixture was subjected to liquid separation ethyl acetate, dried over magnesium sulfate, and then concentrated to obtain 5.5 g of a compound (E-I).

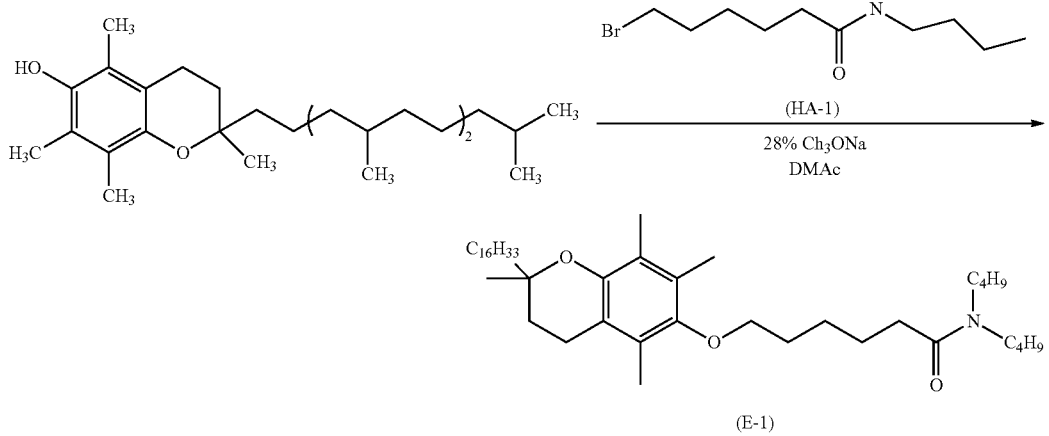

<Synthesis of Aromatic Polyether-Based Compound 1>

The aromatic polyether-based compound 1 is an aromatic diether-based compound (aromatic diether 1) represented by Formula (C-I), and was synthesized with reference to the method described in Synthesis Example 1 of JP1987-045545B (JP-S62-045545B).

(C-I)

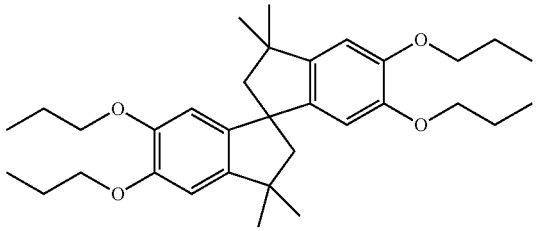

<Synthesis of Aromatic Polyether-Based Compound 2>

The aromatic polyether-based compound 2 is an aromatic diether-based compound (aromatic diether 2) represented by Formula (E-I), and was synthesized by the following method.

<Synthesis of Aromatic Polyether-Based Compound 3>

The aromatic polyether-based compound 3 is an aromatic diether-based compound (aromatic diether 3) represented by Formula (D-I), comprises a structure similar to the compound represented by (27) described in JP1987-010420B (JP-S62-010420B), and was synthesized by the following route.

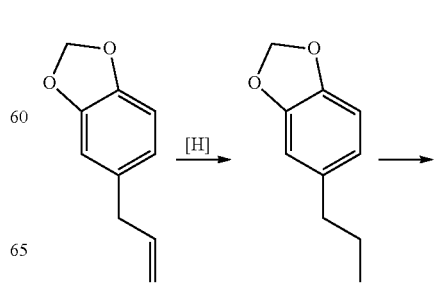

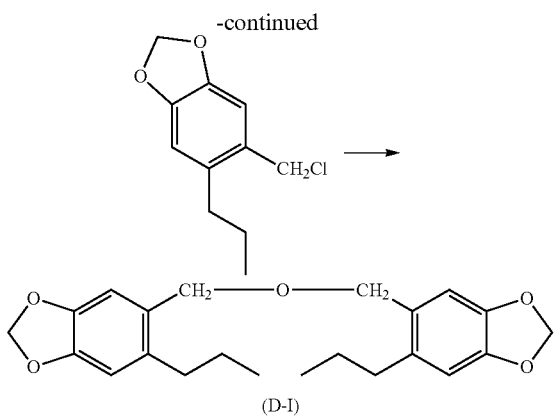

(D-I)

[Other Additives]
<Synthesis of Amine-Based Compound 1>

The amine-based compound 1 is an amine-based compound represented by the following formula, and was synthesized with reference to the method described in WO2005/051915A.

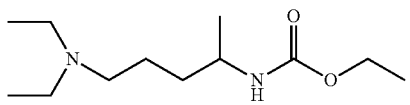

<Hindered Amine-Based Compound>

CHIMASSORB NOR 2020FDL (trade name, manufactured by BASF)

TINUVIN 765 (trade name, manufactured by BASF)

TINUVIN 770DF (trade name, manufactured by BASF)

<Hindered Phenol-Based Compound>

Irganox 1035FF (trade name, manufactured by BASF)

[Polymerization Initiator]

As the polymerization initiator, a compound represented by the following formula (the exemplary compound (A-1) described in JP2011-158655A) was prepared.

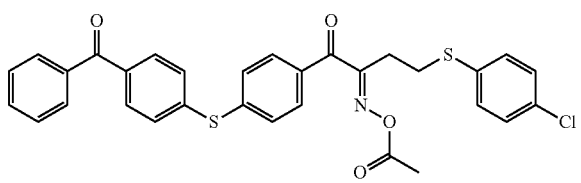 [SMILES: CC(=O)O/N=C(\CCSc1ccc(Cl)cc1)C(=O)c1ccc(Sc2ccc(C(=O)c3ccccc3)cc2)cc1]

[Air Interface Alignment agent (Leveling Agent)]

As the air interface alignment agent, a compound represented by the following formula (the leveling agent T-1 described in JP2016-053709A) was prepared.

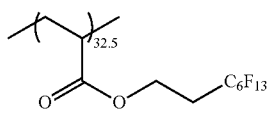

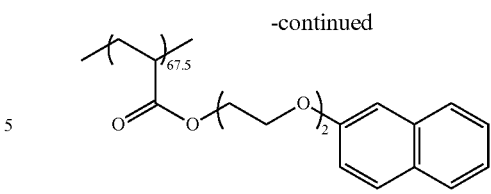

[Solvent]
As the solvent, chloroform was prepared.

Examples 1 to 19 and Comparative Examples 1 to 22

[Preparation of Polymerizable Liquid Crystal Composition]

A polymerizable liquid crystal compound, a polymerization initiator, an air interface alignment agent, and an additive were dissolved in a solvent (chloroform) to prepare each of polymerizable liquid crystal compositions of Examples and Comparative Examples. The type and the blend amount of each of the components are shown as in Table 1 below. Further, in Example 19, a combination of a reverse dispersion liquid crystal 4, a reverse dispersion liquid crystal 5, and a forward dispersion liquid crystal 1 was used as the polymerizable liquid crystal compound as shown Table 1 below, but the addition amounts thereof were 42:42:16 in terms of a mass ratio. In addition, in Table 1 below, the "addition amount ratio" means a content (parts by mass) of an additive with respect to 100 parts by mass of the polymerizable liquid crystal compound in the polymerizable liquid crystal composition.

Furthermore, each of the polymerizable liquid crystal compositions excluding only additives from the composition of each of the polymerizable liquid crystal compositions of Examples and Comparative Examples as a reference was prepared.

[Light Fastness Test]
<Manufacture of Sample>

By a spin-coating method (amount of a polymerizable liquid crystal composition applied: 80 μL, rotation speed: 1,500 rpm), the polymerizable liquid crystal composition was applied onto a glass substrate (EAGLE XG: manufactured by Corning Incorporated) cut to 2.5×3.0 cm and dried to manufacture a coating film on the glass substrate.

Subsequently, the coating film was warmed to 160° C. on a hot plate and irradiated by an ultraviolet irradiating device (manufactured by Nippon Bunka Seiko Co., Ltd.) at an irradiation dose of 500 mJ to manufacture a cured film.

<Measurement of Absorbance of Cured Film before Light Fastness Test>

An absorbance A of a cured film at an absorption maximum wavelength (absorbance of the cured film before a light fastness test) was measured using an infrared-visible measuring device (trade name "UV-3150", manufactured by Shimadzu Corporation). Specifically, a baseline correction was performed using the glass substrate on which the polymerizable liquid crystal composition had not been applied, and then an absorbance A of the cured film at the absorption maximum wavelength was measured.

<Measurement of Absorbance of Cured Film after Light Fastness Test>

First, the glass substrate was set in a Xenon irradiator (SX75 manufactured by Suga Test Instruments Co., Ltd.) so that the cured film of the polymerizable liquid crystal composition became a surface to be irradiated, and a sample was irradiated under a condition of 150 W/m² at a distance of 290 mm from a light source for 2 hours using a #275 filter, thereby obtaining a cured film after the light fastness test.

Subsequently, an absorbance B (absorbance of the cured film after the light fastness test) of the cured film after the light fastness at an absorption maximum wavelength was measured using an infrared-visible measuring device (trade name "UV-3150", manufactured by Shimadzu Corporation).

<Evaluation of Light Fastness>

Using the cured film of the polymerizable liquid crystal composition as a reference (containing no additive), the above-mentioned absorbance A and absorbance B were measured, and a light fastness residual rate X (%) was calculated by the following equation.

Similarly, using the cured film of each of the polymerizable liquid crystal compositions of Examples and Comparative Examples, the above-mentioned absorbance A and absorbance B were measured, and a light fastness residual rate (%) was calculated by the following equation.

$$\text{Light fastness residual rate (\%)} = (\text{Absorbance } B/\text{Absorbance } A) \times 100$$

From the values of the light fastness residual rate X and the light fastness residual rate Y, each obtained as described above, a light fastness improvement rate was calculated by the following equation, and the light fastness was evaluated in accordance with the following evaluation standard.

$$\text{Light fastness improvement rate (\%)} = \text{Light fastness residual rate } Y - \text{Light fastness residual rate } X$$

A: The light fastness improvement rate is 10% or more.

B: The light fastness residual rate is more than 5% and less than 10%.

C: The light fastness improvement rate is more than 0% and 5% or less.

D: The light fastness improvement rate is 0% or less.

<Evaluation Results>

The results of the evaluation tests above are shown in Table 1 below.

TABLE 1

| | Polymerizable liquid crystal compound | | | Additive | | | Polymerization initiator | Air interface alignment agent | Solvent | Evaluation results |
| | Type | pKa calculated | Addition amount (g) | Type | Addition amount (g) | Addition ratio | Addition amount (g) | Addition amount (g) | Addition amount (g) | Light fastness |
|---|---|---|---|---|---|---|---|---|---|---|
| Example 1 | Reverse dispersion liquid crystal 1 | 8.47 | 0.1 | Aromatic diether 1 | 0.001 | 1 | 0.0005 | 0.0002 | 3.18 | B |
| Example 2 | Reverse dispersion liquid crystal 1 | 8.47 | 0.1 | Aromatic diether 1 | 0.005 | 5 | 0.0005 | 0.0002 | 3.3 | A |
| Example 3 | Reverse dispersion liquid crystal 1 | 8.47 | 0.1 | Aromatic diether 1 | 0.01 | 10 | 0.0005 | 0.0002 | 3.46 | A |
| Example 4 | Reverse dispersion liquid crystal 1 | 8.47 | 0.1 | Aromatic diether 2 | 0.001 | 1 | 0.0005 | 0.0002 | 3.18 | A |
| Example 5 | Reverse dispersion liquid crystal 1 | 8.47 | 0.1 | Aromatic diether 2 | 0.005 | 5 | 0.0005 | 0.0002 | 3.3 | A |
| Example 6 | Reverse dispersion liquid crystal 1 | 8.47 | 0.1 | Aromatic diether 2 | 0.01 | 10 | 0.0005 | 0.0002 | 3.46 | A |
| Example 7 | Reverse dispersion liquid crystal 1 | 8.47 | 0.1 | Aromatic diether 2 | 0.02 | 20 | 0.0005 | 0.0002 | 3.77 | A |
| Example 8 | Reverse dispersion liquid crystal 1 | 8.47 | 0.1 | Aromatic diether 3 | 0.001 | 1 | 0.0005 | 0.0002 | 3.18 | B |
| Example 9 | Reverse dispersion liquid crystal 1 | 8.47 | 0.1 | Aromatic diether 3 | 0.005 | 5 | 0.0005 | 0.0002 | 3.3 | A |
| Example 10 | Reverse dispersion liquid crystal 1 | 8.47 | 0.1 | Aromatic diether 3 | 0.01 | 10 | 0.0005 | 0.0002 | 3.46 | A |
| Example 11 | Reverse dispersion liquid crystal 1 | 8.47 | 0.1 | Aromatic diether 3 | 0.02 | 20 | 0.0005 | 0.0002 | 3.77 | A |
| Example 12 | Reverse dispersion liquid crystal 2 | 8.82 | 0.1 | Aromatic diether 1 | 0.005 | 5 | 0.0005 | 0.0002 | 3.3 | A |
| Example 13 | Reverse dispersion liquid crystal 2 | 8.82 | 0.1 | Aromatic diether 2 | 0.005 | 5 | 0.0005 | 0.0002 | 3.3 | A |
| Example 14 | Reverse dispersion liquid crystal 2 | 8.82 | 0.1 | Aromatic diether 3 | 0.005 | 5 | 0.0005 | 0.0002 | 3.3 | A |
| Example 15 | Reverse dispersion liquid crystal 3 | 9.56 | 0.1 | Aromatic diether 1 | 0.005 | 5 | 0.0005 | 0.0002 | 3.3 | B |
| Example 16 | Reverse dispersion liquid crystal 3 | 9.56 | 0.1 | Aromatic diether 2 | 0.005 | 5 | 0.0005 | 0.0002 | 3.3 | B |
| Example 17 | Reverse dispersion liquid crystal 4 | 8.3 | 0.1 | Aromatic diether 1 | 0.005 | 5 | 0.0005 | 0.0002 | 3.3 | B |
| Example 18 | Reverse dispersion liquid crystal 5 | 8.71 | 0.1 | Aromatic diether 1 | 0.005 | 5 | 0.0005 | 0.0002 | 3.3 | B |
| Example 19 | Reverse dispersion liquid crystal 4 Reverse dispersion liquid crystal 5 Forward dispersion liquid crystal 2 | — | 0.1 | Aromatic diether 1 | 0.005 | 5 | 0.0005 | 0.0002 | 3.3 | B |
| Comparative Example 1 | Reverse dispersion liquid crystal 4 | 8.47 | 0.1 | Amine-based compound 1 | 0.001 | 1 | 0.0005 | 0.0002 | 3.18 | C |

TABLE 1-continued

| | Polymerizable liquid crystal compound | | Additive | | | Polymerization initiator | Air interface alignment agent Addition | Solvent Addition | Evaluation results |
| --- | --- | --- | --- | --- | --- | --- | --- | --- | --- |
| Type | pKa calculated | Addition amount (g) | Type | Addition amount (g) | Addition ratio | Addition amount (g) | amount (g) | amount (g) | Light fastness |
| Comparative Example 2 | Reverse dispersion liquid crystal 1 | 8.47 | 0.1 | Amine-based compound 1 | 0.005 | 5 | 0.0005 | 0.0002 | 3.3 | D |
| Comparative Example 3 | Reverse dispersion liquid crystal 1 | 8.47 | 0.1 | Amine-based compound 1 | 0.01 | 10 | 0.0005 | 0.0002 | 3.46 | D |
| Comparative Example 4 | Reverse dispersion liquid crystal 1 | 8.47 | 0.1 | CHIMASORB NOR 2020FDL | 0.001 | 1 | 0.0005 | 0.0002 | 3.18 | D |
| Comparative Example 5 | Reverse dispersion liquid crystal 1 | 8.47 | 0.1 | CHIMASORB NOR 2020FDL | 0.005 | 5 | 0.0005 | 0.0002 | 3.3 | C |
| Comparative Example 6 | Reverse dispersion liquid crystal 1 | 8.47 | 0.1 | CHIMASORB NOR 2020FDL | 0.01 | 10 | 0.0005 | 0.0002 | 3.46 | C |
| Comparative Example 7 | Reverse dispersion liquid crystal 1 | 8.47 | 0.1 | TINUVIN 765 | 0.001 | 1 | 0.0005 | 0.0002 | 3.18 | C |
| Comparative Example 8 | Reverse dispersion liquid crystal 1 | 8.47 | 0.1 | TINUVIN 765 | 0.005 | 5 | 0.0005 | 0.0002 | 3.3 | D |
| Comparative Example 9 | Reverse dispersion liquid crystal 1 | 8.47 | 0.1 | TINUVIN 765 | 0.01 | 10 | 0.0005 | 0.0002 | 3.46 | C |
| Comparative Example 10 | Reverse dispersion liquid crystal 1 | 8.47 | 0.1 | TINUVIN 770DF | 0.001 | 1 | 0.0005 | 0.0002 | 3.18 | D |
| Comparative Example 11 | Reverse dispersion liquid crystal 1 | 8.47 | 0.1 | TINUVIN 770DF | 0.005 | 5 | 0.0005 | 0.0002 | 3.3 | D |
| Comparative Example 12 | Reverse dispersion liquid crystal 1 | 8.47 | 0.1 | TINUVIN 770DF | 0.01 | 10 | 0.0005 | 0.0002 | 3.46 | C |
| Comparative Example 13 | Reverse dispersion liquid crystal 1 | 8.47 | 0.1 | Irganox 1035FF | 0.001 | 1 | 0.0005 | 0.0002 | 3.18 | C |
| Comparative Example 14 | Reverse dispersion liquid crystal 1 | 8.47 | 0.1 | Irganox 1035FF | 0.005 | 5 | 0.0005 | 0.0002 | 3.3 | D |
| Comparative Example 15 | Reverse dispersion liquid crystal 1 | 8.47 | 0.1 | Irganox 1035FF | 0.01 | 10 | 0.0005 | 0.0002 | 3.46 | D |
| Comparative Example 16 | Reverse dispersion liquid crystal 2 | 8.47 | 0.1 | Irganox 1035FF | 0.005 | 5 | 0.0005 | 0.0002 | 3.3 | D |
| Comparative Example 17 | Reverse dispersion liquid crystal 2 | 8.82 | 0.1 | Amine-based compound 1 | 0.005 | 5 | 0.0005 | 0.0002 | 3.3 | D |
| Comparative Example 18 | Reverse dispersion liquid crystal 2 | 8.82 | 0.1 | TINUVIN 765 | 0.005 | 5 | 0.0005 | 0.0002 | 3.3 | D |
| Comparative Example 19 | Reverse dispersion liquid crystal 2 | 8.82 | 0.1 | Irganox 1035FF | 0.005 | 5 | 0.0005 | 0.0002 | 3.3 | D |
| Comparative Example 20 | Reverse dispersion liquid crystal 3 | 9.56 | 0.1 | Amine-based compound 1 | 0.005 | 5 | 0.0005 | 0.0002 | 3.3 | D |
| Comparative Example 21 | Reverse dispersion liquid crystal 3 | 9.56 | 0.1 | TINUVIN 765 | 0.005 | 5 | 0.0005 | 0.0002 | 3.3 | D |
| Comparative Example 22 | Reverse dispersion liquid crystal 3 | 9.56 | 0.1 | Irganox 1035FF | 0.005 | 5 | 0.0005 | 0.0002 | 3.3 | D |
| Comparative Example 22 | Forward dispersion liquid crystal 1 | 10.8 | 0.1 | Aromatic diether 1 | 0.005 | 5 | 0.0005 | 0.0002 | 3.3 | D |

From the evaluation results shown in Table 1, it was found that in a case where a polymerizable liquid crystal composition containing an aromatic polyether-based compound is used as an additive, it is possible to form a film having excellent light fastness (Examples).

In contrast, it was found that in a case where a polymerizable liquid crystal composition containing no aromatic polyether-based compound is used as an additive, the light fastness of a film thus obtained is deteriorated (Comparative Examples 1 to 21).

In addition, it was found that in a case where a polymerizable liquid crystal compound having forward wavelength dispersion properties is used, the light fastness of a film thus obtained is deteriorated even with the addition of an aromatic polyether-based compound (Comparative Example 22).

[Preparation of Composition for Optical Alignment Film]

By a method which will be described later, a polymer, a low molecular compound, a crosslinking agent, and a crosslinking catalyst was synthesized or prepared.

<Synthesis of Polymer>

100.0 parts by mass of 2-(3,4-epoxycyclohexyl)ethyltrimethoxysilane, 500 parts by mass of methyl isobutyl ketone, and 10.0 parts by mass of triethylamine were introduced into a reaction vessel comprising a stirrer, a thermometer, a dropping funnel, and a reflux condenser, and mixed at room temperature. Subsequently, 100 parts by mass of deionized water was added dropwise from the dropping funnel for 30 minutes and then allowed to undergo a reaction at 80° C. for 6 hours while mixing under reflux. After completion of the reaction, the organic phase was extracted and washed until water after washing with a 0.2%-by-mass aqueous ammonium nitrate solution became neutral, and then the solvent and water were distilled off under reduced pressure to obtain an epoxy-containing polyorganosiloxane as a viscous transparent liquid.

The epoxy-containing polyorganosiloxane was subjected to $^1$H-NMR analysis, and it was thus found that a peak based on an oxiranyl group around a chemical shift ($\delta$)=3.2 ppm was obtained as for a theoretical strength, and a side reaction of the epoxy group did not occur during the reaction. The weight-average molecular weight Mw and the epoxy equivalents of the epoxy-containing polyorganosiloxane were 2,200 and 186 g/mol, respectively.

Next, 10.5 parts by mass of the epoxy-containing polyorganosiloxane obtained above, 0.4 parts by mass of an acrylic group-containing carboxylic acid (manufactured by Toagosei Co., Ltd., trade name "Aronix M-5300", acrylic acid ω-carboxypolycaprolactone (polymerization degree n≈2)), 20 parts by mass of butyl acetate, 0.5 parts by mass of the cinnamic acid derivative obtained by the method of Synthesis Example 1 of JP2015-026050A, 0.5 parts by mass of tetrahydrofuroic acid (manufactured by Wako Pure Chemical Industries, Ltd.), and 0.3 parts by mass of tetrabutylammonium bromide were introduced into a 100-mL three-neck flask and stirred at 90° C. for 12 hours. After completion of the reaction, the mixture was diluted with butyl acetate in the same amount (mass) as that of the reaction liquid and washed three times with water. The solution was concentrated and twice subjected to an operation of dilution with butyl acetate, thereby finally obtaining a solution including a polyorganosiloxane (polymer) containing an optically aligned group. The weight-average molecular weight Mw of the polymer was 10,000.

<Low Molecular Compound>

A low molecular compound represented by Formula B (NOMCORT TAB, manufactured by Nisshin OilliO Group) was used.

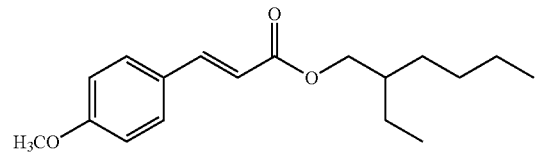

B

<Crosslinking Agent>

As the crosslinking agent, a polyfunctional epoxy compound (EPOLEAD GT401, manufactured by Daniel Chemical Industries, Ltd.) was used.

<Crosslinking Catalyst>

A thermal acid generator (San-Aid SI-60, manufactured by Sanshin Chemical Industry Co., Ltd.) was used as the crosslinking catalyst for the purpose of accelerating crosslinking.

<Preparation of Composition for Optical Alignment Film>

4.6 parts by mass of the above-mentioned polymer, 0.8 parts by mass of the above-mentioned low molecular compound, 0.8 parts by mass of the above-mentioned crosslinking agent, and 0.8 parts by mass of the above-mentioned crosslinking catalyst were added with respect to 100 parts by mass of butyl acetate, stirred, and then filtered through a filter having a pore diameter of 1 μm to obtain a liquid crystal aligning agent having a concentration of the solid content of 7.5% by mass. Further, in the obtained liquid crystal aligning agent, components such as a polymer were dissolved in a solvent in the same amount as the addition amount.

Examples 20 to 23 and Comparative Example 23

[Preparation of Coating Liquid for Forming Optically Anisotropic Film]

Coating liquids 1 to 5 for forming an optically anisotropic film, which have the following compositions, were prepared.

| Coating liquid 1 for forming an optically anisotropic film | |
|---|---|
| Reverse dispersion liquid crystal 1 | 95.00 parts by mass |
| Aromatic diether 1 | 5.00 parts by mass |
| Polymerization initiator A-1 below | 0.05 parts by mass |
| Leveling agent T-1 below | 0.20 parts by mass |
| Cyclopentanone | 424.8 parts by mass |

Polymerization initiator A-1

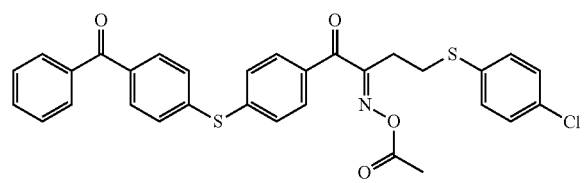

Leveling agent T-1

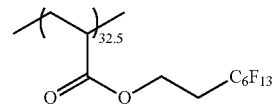

-continued

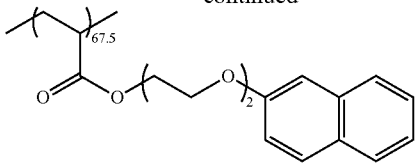

| Coating liquid 2 for forming an optically anisotropic film | |
|---|---|
| Reverse dispersion liquid crystal 2 | 95.00 parts by mass |
| Aromatic diether 1 | 5.00 parts by mass |
| Polymerization initiator A-1 | 0.05 parts by mass |
| Leveling agent T-1 | 0.20 parts by mass |
| Cyclopentanone | 424.8 parts by mass |

| Coating liquid 3 for forming an optically anisotropic film | |
|---|---|
| Reverse dispersion liquid crystal 3 | 95.00 parts by mass |
| Aromatic diether 1 | 5.00 parts by mass |
| Polymerization initiator A-1 | 0.05 parts by mass |
| Leveling agent T-1 | 0.20 parts by mass |
| Cyclopentanone | 424.8 parts by mass |

| Coating liquid 4 for forming an optically anisotropic film | |
|---|---|
| Reverse dispersion liquid crystal 4 | 40.00 parts by mass |
| Reverse dispersion liquid crystal 5 | 40.00 parts by mass |
| Forward dispersion liquid crystal 2 | 15.00 parts by mass |
| Aromatic diether 1 | 5.00 parts by mass |
| Polymerization initiator A-1 | 0.50 parts by mass |
| Leveling agent T-1 | 0.20 parts by mass |
| Hisolve MTEM (manufactured by TOHO Chemical Industry Co., Ltd.) | 2.00 parts by mass |
| NKester A-200 (manufactured by Shin Nakamura chemical Co., Ltd.) | 1.00 part by mass |
| Methyl ethyl ketone | 424.8 parts by mass |

| Coating liquid 5 for forming an optically anisotropic film | |
|---|---|
| Forward dispersion liquid crystal 1 | 95.00 parts by mass |
| Aromatic diether 1 | 5.00 parts by mass |
| Polymerization initiator A-1 | 0.50 parts by mass |
| Leveling agent T-1 | 0.20 parts by mass |
| Hisolve MTEM (manufactured by TOHO Chemical Industry Co., Ltd.) | 2.00 parts by mass |
| NKester A-200 (manufactured by Shin Nakamura chemical Co., Ltd.) | 1.00 part by mass |
| Methyl ethyl ketone | 424.8 parts by mass |

[Manufacture of Cellulose Acylate Film 1]
<Manufacture of Core Layer Cellulose Acylate Dope>
The following composition was put into a mixing tank and stirred to dissolve the respective components to prepare a cellulose acetate solution for use as a core layer cellulose acylate dope.

| Core layer cellulose acylate dope | |
|---|---|
| Cellulose acetate having a degree of substitution with acetyl of 2.88 | 100 parts by mass |
| Polyester compound B described in Examples of JP2015-227955A | 12 parts by mass |
| Compound F below | 2 parts by mass |

| Core layer cellulose acylate dope | |
|---|---|
| Methylene chloride (first solvent) | 430 parts by mass |
| Methanol (second solvent) | 64 parts by mass |

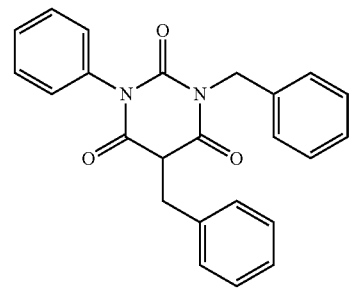

Compound F

<Manufacture of Outer Layer Cellulose Acylate Dope>
10 parts by mass of the following matting solution was added to 90 parts by mass of the core layer cellulose acylate dope to prepare a cellulose acetate solution which is used as an outer layer cellulose acylate dope.

| Matting solution | |
|---|---|
| Silica particles having an average particle size of 20 nm (AEROSIL R972, manufactured by Nippon Aerosil Co., Ltd.) | 2 parts by mass |
| Methylene chloride (first solvent) | 76 parts by mass |
| Methanol (second solvent) | 11 parts by mass |
| Core layer cellulose acylate dope above | 1 part by mass |

<Manufacture of Cellulose Acylate Film 1>
The core layer cellulose acylate dope and the outer layer cellulose acylate dope were filtered through a filter paper having an average pore diameter of 34 μm and a sintered metal filter having an average pore diameter of 10 μm, and then all the three layers of the core layer cellulose acylate dope and the outer layer cellulose acylate dopes of both sides were simultaneously cast on a drum at 20° C. from a casting port (band caster).

Peeling was performed in a state of a solvent content of approximately 20% by mass, and the both ends of the film in the width direction were fixed with a tenter clip and dried while stretching the film at a stretch ratio of 1.1 times in the transverse direction.

Thereafter, the film was transported between rolls of a heat treatment device and further dried to manufacture a cellulose acylate film 1 having a thickness of 40 μm.

The thickness of the core layer of the obtained cellulose acylate film 1 was 36 μm and the thickness of each of the outer layers arranged on the both sides of the core layer was 2 μm.

In addition, the in-plane retardation of the obtained cellulose acylate film 1 was 0 nm.

[Manufacture of Optical Film]
The composition for an optical alignment film prepared above was applied onto one surface of the manufactured cellulose acylate film 1 with a bar coater.

After application, the film was dried for 1 minute on a hot plate at 120° C. to remove the solvent, thereby forming a photoisomerization composition layer having a thickness of 0.3 μm.

The obtained photoisomerization composition layer was irradiated with polarized ultraviolet rays (10 mJ/cm$^2$, an ultra-high pressure mercury lamp used), thereby forming an optical alignment film.

Subsequently, the coating liquids 1 to 5 for forming an optically anisotropic film prepared above were each applied onto the optical alignment film with a bar coater, thereby forming a composition layer.

The formed composition layer was once heated to 110° C. on a hot plate and then cooled to 60° C. to stabilize the alignment.

Thereafter, the composition layer was kept at 60° C. and irradiated with ultraviolet rays (500 mJ/cm$^2$, an ultra-high pressure mercury lamp used) to fix the alignment in a nitrogen atmosphere (oxygen concentration 100 ppm), thereby forming optically anisotropic films having a thickness of 2.3 μm (positive A plates 1 to 5), and thus manufacturing optical films 1 to 5.

The in-plane retardation of the obtained optical film was 140 nm.

[Evaluation of Light Fastness]

First, the glass substrate was set in a Xenon irradiator (SX75 manufactured by Suga Test Instruments Co., Ltd.) so that the cured film of the optically anisotropic film (positive A plate) became a surface to be irradiated, and a sample was irradiated under a condition of 150 W/m$^2$ at a distance of 290 mm from a light source for 2 hours using a #275 filter, thereby obtaining a cured film after the light fastness test, with which a residual retardation was measured.

From the initial retardation (140 nm) before the test and the residual retardation as described above, a light fastness residual rate X (%) was calculated by the following equation.

Similarly, from the cured film of each of the polymerizable liquid crystal compositions of Examples and Comparative Examples, a light fastness residual rate Y (%) was calculated by the following equation.

Light fastness residual rate (%)=(Residual retardation/Initial retardation)×100

From the values of the light fastness residual rate X and the light fastness residual rate Y obtained as described above, a light fastness improvement rate was calculated by the following equation, and the light fastness was evaluated in accordance with the following evaluation standard. The results are shown in Table 2 below.

Light fastness improvement rate (%)=Light fastness residual rate Y-Light fastness residual rate X A: The light fastness improvement rate is 10% or more.

B: The light fastness residual rate is more than 5% and less than 10%.

C: The light fastness improvement rate is more than 0% and 5% or less.

D: The light fastness improvement rate is 0% or less.

<Evaluation Results>

The results of the evaluation tests above are shown in Table 2 below.

TABLE 2

|  |  | Polymerizable liquid crystal compound | Optically anisotropic film (coating liquid) | Positive A plate | Optical film | Light fastness |
|---|---|---|---|---|---|---|
| Example 20 | Reverse dispersion liquid crystal 1 | 1 | 1 | 1 | A |
| Example 21 | Reverse dispersion liquid crystal 2 | 2 | 2 | 2 | A |
| Example 22 | Reverse dispersion liquid crystal 3 | 3 | 3 | 3 | A |
| Example 23 | Reverse dispersion liquid crystal 4 Reverse dispersion liquid crystal 5 Forward dispersion liquid crystal 2 | 4 | 4 | 4 | B |
| Comparative Example 23 | Forward dispersion liquid crystal 1 | 5 | 5 | 5 | C |

Example 24

[Manufacture of Positive C Plate 1]

A commercially available triacetyl cellulose film "Z-TAC" (manufactured by Fuji Photo Film Co., Ltd.) [hereinafter simply referred to as a "cellulose acylate film 2"] was used as a temporary support.

The cellulose acylate film 2 was passed through a dielectric heating roll at a temperature of 60° C. to raise the film surface temperature to 40° C., and then an alkaline solution having the composition shown below was applied onto one surface of the film at a coating amount of 14 ml/m$^2$ using a bar coater, heated to 110° C., and transported for 10 seconds under a steam-type far-infrared heater manufactured by Noritake Co., Ltd. Subsequently, pure water was similarly applied using a bar coater at 3 ml/m$^2$.

Subsequently, washing with water by a fountain coater and dehydration by an air knife were repeated three times, and then the film was transported to a drying zone at 70° C. for 10 seconds and dried, thereby manufacturing a cellulose acylate film 2 which had been subjected to an alkali saponification treatment.

| Alkali solution | |
|---|---|
| Potassium hydroxide | 4.7 parts by mass |
| Water | 15.8 parts by mass |
| Isopropanol | 63.7 parts by mass |
| Fluorine-containing surfactant SF-1 ($C_{14}H_{29}O(CH_2CH_2O)_{20}H$) | 1.0 part by mass |
| Propylene glycol | 14.8 parts by mass |

A coating liquid forming an alignment film having the following composition was continuously applied onto the cellulose acylate film 2 which had been subjected to an alkali saponification treatment, using a #8 wire bar. The film was dried with hot air at 60° C. for 60 seconds, and further dried with a hot air at 100° C. for 120 seconds, thereby forming an alignment film.

| Coating liquid for forming an alignment film | |
|---|---|
| Polyvinyl alcohol (manufactured by Kuraray Co., Ltd., PVA103) | 2.4 parts by mass |
| Isopropyl alcohol | 1.6 parts by mass |
| Methanol | 36 parts by mass |
| Water | 60 parts by mass |

The following coating liquid N for forming an optically anisotropic film was applied onto the cellulose acylate film 2 having an alignment film manufactured above, aged at 60° C. for 60 seconds, and irradiated with ultraviolet rays at 1,000 mJ/cm$^2$ using a 70-mW/cm$^2$ air-cooling metal halide lamp (manufactured by Eye Graphics Co., Ltd.) in air, and the alignment state thereof was fixed to align the polymerizable liquid crystal compound vertically, thereby manufacturing a positive C plate 1. The Rth at a wavelength of 550 nm was −60 nm.

| Coating liquid N for forming an optically anisotropic film | |
|---|---|
| Reverse dispersion liquid crystal 1 | 100 parts by mass |
| Aromatic diether 1 | 5 parts by mass |
| Vertical aligning agent (S01) below | 1 part by mass |
| Vertical aligning agent (S02) below | 0.5 parts by mass |
| Ethylene oxide-modified trimethylol propanetriacrylate (V#360, manufactured by Osaka Organic Chemical Industry Ltd.) | 8 parts by mass |
| Irgacure 907 (manufactured by BASF) | 3 parts by mass |
| KAYACURE DETX (manufactured by Nippon Kayaku Co., Ltd.) | 1 part by mass |
| Compound B03 below | 0.4 parts by mass |
| Methyl ethyl ketone | 170 parts by mass |
| Cyclohexanone | 30 parts by mass |

(In the formula of the compound B03, a=90 and b=10.)

Example 25

A positive C plate 2 was manufactured in the same manner as in Example 24, except that the following coating liquid M for forming an optically anisotropic film was used instead of the coating liquid N for forming an optically anisotropic film. The Rth at a wavelength of 550 nm was −60 nm.

| Coating liquid M for forming an optically anisotropic film | |
|---|---|
| Reverse dispersion liquid crystal 2 | 100 parts by mass |
| Aromatic diether 1 | 5 parts by mass |
| Vertical aligning agent (S01) | 1 part by mass |
| Vertical aligning agent (S02) | 0.5 parts by mass |
| Ethylene oxide-modified trimethylol propanetriacrylate (V#360, manufactured by Osaka Organic Chemical Industry Ltd.) | 8 parts by mass |
| Irgacure 907 (manufactured by BASF) | 3 parts by mass |
| KAYACURE DETX (manufactured by Nippon Kayaku Co., Ltd.) | 1 part by mass |
| Compound B03 | 0.4 parts by mass |
| Methyl ethyl ketone | 170 parts by mass |
| Cyclohexanone | 30 parts by mass |

Example 26

A positive C plate 3 was manufactured in the same manner as in Example 24, except that the following coating liquid L for forming an optically anisotropic film was used instead of the coating liquid N for forming an optically anisotropic film. The Rth at a wavelength of 550 nm was −60 nm.

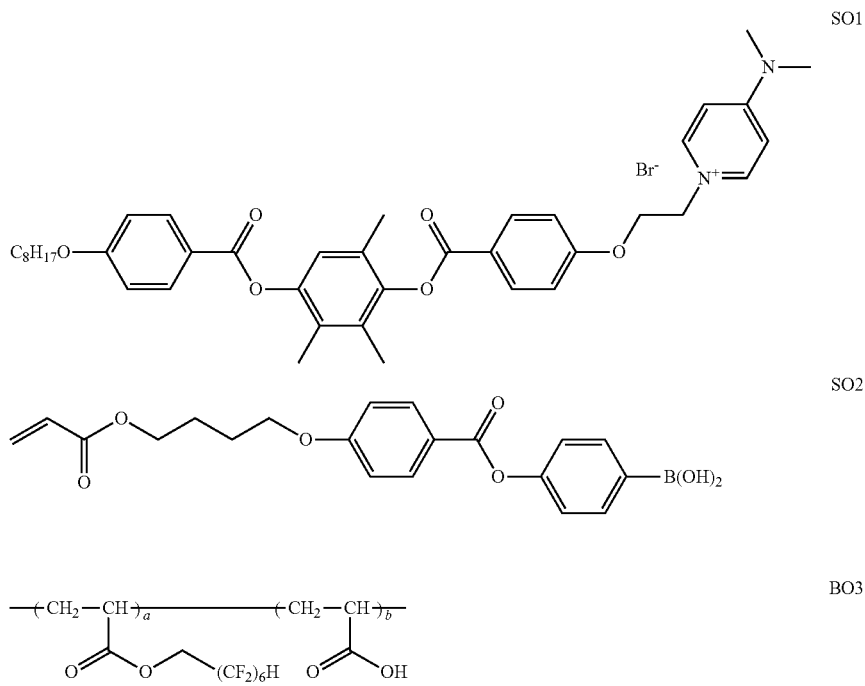

| Coating liquid L for forming an optically anisotropic film | |
| --- | --- |
| Reverse dispersion liquid crystal 3 | 100 parts by mass |
| Aromatic diether 1 | 5 parts by mass |
| Vertical aligning agent (S01) | 1 part by mass |
| Vertical aligning agent (S02) | 0.5 parts by mass |
| Ethylene oxide-modified trimethylol propanetriacrylate (V#360, manufactured by Osaka Organic Chemical Industry Ltd.) | 8 parts by mass |
| Irgacure 907 (manufactured by BASF) | 3 parts by mass |
| KAYACURE DETX (manufactured by Nippon Kayaku Co., Ltd.) | 1 part by mass |
| Compound B03 | 0.4 parts by mass |
| Methyl ethyl ketone | 170 parts by mass |
| Cyclohexanone | 30 parts by mass |

Example 27

A positive C plate 4 was manufactured in the same manner as in Example 24, except that the following coating liquid O for forming an optically anisotropic film was used instead of the coating liquid N for forming an optically anisotropic film. The Rth at a wavelength of 550 nm was −60 nm.

| Coating liquid O for forming an optically anisotropic film | |
| --- | --- |
| Reverse dispersion liquid crystal 4 | 80 parts by mass |
| Reverse dispersion liquid crystal 5 | 20 parts by mass |
| Aromatic diether 1 | 5 parts by mass |
| Vertical aligning agent (S01) | 1 part by mass |
| Vertical aligning agent (S02) | 0.5 parts by mass |
| Ethylene oxide-modified trimethylol propanetriacrylate (V#360, manufactured by Osaka Organic Chemical Industry Ltd.) | 8 parts by mass |
| Irgacure 907 (manufactured by BASF) | 3 parts by mass |
| KAYACURE DETX (manufactured by Nippon Kayaku Co., Ltd.) | 1 part by mass |
| Compound B03 | 0.4 parts by mass |
| Methyl ethyl ketone | 170 parts by mass |
| Cyclohexanone | 30 parts by mass |

Comparative Example 24

A positive C plate 5 was manufactured in the same manner as in Example 24, except that the following coating liquid P for forming an optically anisotropic film was used instead of the coating liquid N for forming an optically anisotropic film. The Rth at a wavelength of 550 nm was −60 nm.

| Coating liquid P for forming an optically anisotropic film | |
| --- | --- |
| Forward dispersion liquid crystal 2 | 100 parts by mass |
| Aromatic diether 1 | 5 parts by mass |
| Vertical aligning agent (S01) | 1 part by mass |
| Vertical aligning agent (S02) | 0.5 parts by mass |
| Ethylene oxide-modified trimethylol propanetriacrylate (V#360, manufactured by Osaka Organic Chemical Industry Ltd.) | 8 parts by mass |
| Irgacure 907 (manufactured by BASF) | 3 parts by mass |
| KAYACURE DETX (manufactured by Nippon Kayaku Co., Ltd.) | 1 part by mass |
| Compound B03 | 0.4 parts by mass |
| Methyl ethyl ketone | 170 parts by mass |
| Cyclohexanone | 30 parts by mass |

[Evaluation of Light Fastness]

The glass substrate was set in a Xenon irradiator (SX75 manufactured by Suga Test Instruments Co., Ltd.) so that the cured film of the positive C plate became a surface to be irradiated, and a sample was irradiated under a condition of 150 W/m² at a distance of 290 mm from a light source for 2 hours using a #275 filter, thereby obtaining a cured film after the light fastness test, with which a residual Rth was measured.

From the initial Rth (60 nm) before the test and the residual Rth, each as described above, a light fastness residual rate X (%) was calculated by the following equation.

Similarly, using the cured film of each of the polymerizable liquid crystal compositions of Examples and Comparative Examples, a light fastness residual rate Y (%) was calculated by the following equation.

Light fastness residual rate (%)=(Residual $Rth$/Initial $Rth$)×100

From the values of the light fastness residual rate X and the light fastness residual rate Y, each obtained as described above, a light fastness improvement rate was calculated by the following equation, and the light fastness was evaluated in accordance with the following evaluation standard. The results are shown in Table 3 below.

Light fastness improvement rate (%)=Light fastness residual rate $Y$-Light fastness residual rate $X$ A: The light fastness improvement rate is 10% or more.
B: The light fastness residual rate is more than 5% and less than 10%.
C: The light fastness improvement rate is more than 0% and 5% or less.
D: The light fastness improvement rate is 0% or less.

<Evaluation Results>

The results of the above evaluation tests are shown in Table 3 below.

TABLE 3

| | Polymerizable liquid crystal compound | Optically anisotropic film (coating liquid) | Positive C plate | Light fastness |
| --- | --- | --- | --- | --- |
| Example 24 | Reverse dispersion liquid crystal 1 | N | 1 | A |
| Example 25 | Reverse dispersion liquid crystal 2 | M | 2 | A |
| Example 26 | Reverse dispersion liquid crystal 3 | L | 3 | A |
| Example 27 | Reverse dispersion liquid crystal 4 Reverse dispersion liquid crystal 5 | O | 4 | B |
| Comparative Example 24 | Forward dispersion liquid crystal 2 | P | 5 | C |

Example 28

[Manufacture of Antireflection Plate (Circularly Polarizing Plate) for Organic EL Display Device]
<Manufacture of Circularly Polarizing Plate>

The positive C plate 1 of Example 24 was transferred to the side of the optically anisotropic film (positive A plate 1) of the optical film 1 of Example 20 through an adhesive, and the cellulose acylate film 2 was removed. Further, a polarizer was adhered to the side of the cellulose acylate film 1 of the optical film 1 through an adhesive to manufacture a circularly polarizing plate.

In addition, any of the optical film 1 (positive A plate 1) of Example 20 used for the manufacture of the circularly polarizing plate, and the positive C plate 1 of Example 24 both used the samples after the above-mentioned evaluation of light fastness.

Example 29

A circularly polarizing plate was manufactured by the same method as in Example 28, except that the optical film 2 of Example 21 was used instead of the optical film 1 of Example 20, and the positive C plate 2 of Example 25 was used instead of the positive C plate 1.

Example 30

A circularly polarizing plate was manufactured by the same method as in Example 28, except that the optical film 3 of Example 22 was used instead of the optical film 1 of Example 20, and the positive C plate 3 of Example 26 was used instead of the positive C plate 1.

Example 31

A circularly polarizing plate was manufactured by the same method as in Example 28, except that the optical film 4 of Example 23 was used instead of the optical film 1 of Example 20, and the positive C plate 4 of Example 27 was used instead of the positive C plate 1.

Comparative Example 25

A circularly polarizing plate was manufactured by the same method as in Example 28, except that the optical film 5 of Comparative Example 23 was used instead of the optical film 1 of Example 20, and the positive C plate 5 of Comparative Example 24 was used instead of the positive C plate 1.

[Mounting into Organic EL Panel and Evaluation Thereof]

GALAXY SII manufactured by SAMSUNG having an organic EL panel mounted therein was disassembled to peel the circularly polarizing plate, and adhered with an adhesive such that the side of the positive C plate of the circularly polarizing plate manufactured above became the panel side, thereby manufacturing a display device.

The display device was allowed to perform white display, black display, and image display, reflected light was observed upon application of fluorescent light and the like at a polar angle of 60 degrees, and the display qualities were evaluated in accordance with the following standard.

A: Light leakage in the black state is not visible at all (excellent).
B: Light leakage in the black state is very slightly visible, but is acceptable.
C: Light leakage in the black state is clearly visible.

TABLE 4

| | Optical film | Positive C plate | Display performance |
|---|---|---|---|
| Example 28 | 1 | 1 | B |
| Example 29 | 2 | 2 | B |
| Example 30 | 3 | 3 | B |
| Example 31 | 4 | 4 | A |
| Comparative Example 25 | 5 | 5 | C |

From the results shown in Table 4, it was found that in a case where the optical ti m of the embodiment of the present invention, in particular, the optical film having two or more layers of the optically anisotropic films of the embodiment of the present invention, in which at least one of the layers is a positive A plate and at least one of the other layers is a positive C plate is used in a circularly polarizing plate, the display function of an organic EL display device is improved.

EXPLANATION OF REFERENCES 10 optical film
12 optically anisotropic film
14 alignment film
16 support
18 hard coat layer

What is claimed is:
1. A polymerizable liquid crystal composition comprising:
a polymerizable liquid crystal compound having reverse-wavelength dispersion properties; and
an aromatic polyether compound,
wherein the aromatic polyether compound includes at least one compound selected from the group consisting of Formula (B), Formula (C) and Formula (D), and
wherein the compound represented by Formula (B) is a compound represented by Formula (E) or Formula (F),

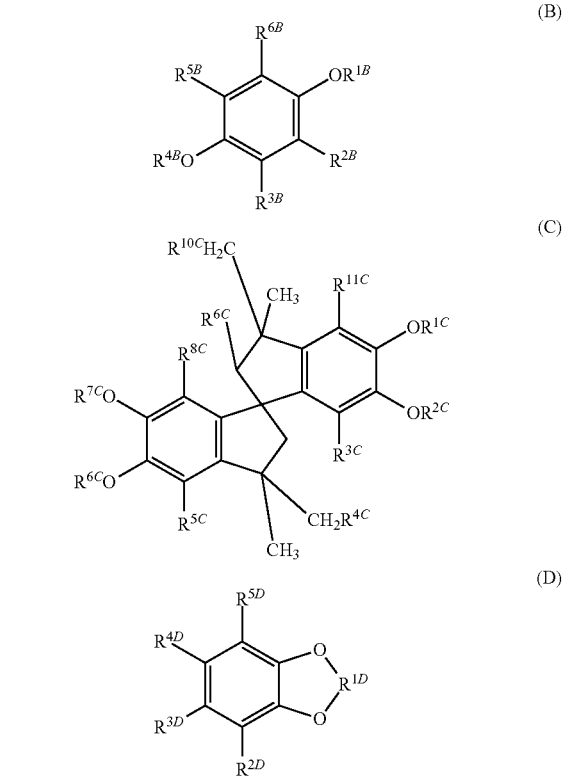

in Formula (B), $R^{1B}$ and $R^{4B}$ each independently represent a monovalent organic group, $R^{2B}$, $R^{3B}$, $R^{5B}$, and $R^{6B}$ each independently represent a hydrogen atom or a monovalent substituent, and $R^{1B}$ and $R^{2B}$, $R^{2B}$ and $R^{3B}$, $R^{3B}$ and $R^{4B}$, $R^{4B}$ and $R^{5B}$, $R^{5B}$ and $R^{6B}$, or $R^{6B}$ and $R^{1B}$ may be bonded to each other to form a ring,
in Formula (C), $R^{1C}$, $R^{2C}$, $R^{6C}$, and $R^{7C}$ each independently represent a monovalent organic group, $R^{3C}$, $R^{5C}$, $R^{8C}$ and $R^{11C}$ each independently represent a hydrogen atom or a monovalent substituent, and $R^{4C}$, $R^{9C}$ and $R^{10C}$ each independently represent a hydrogen atom or a monovalent organic group, in Formula (D), $R^{1D}$ represents an alkylene group having 1 to 3 carbon atoms, $R^{2D}$, $R^{3D}R^{4D}$, and $R^{5D}$ each independently represent a hydrogen atom or a monovalent substituent, and $R^{2D}$ and $R^{3D}$, or $R^{3D}$ and $R^{4D}$ may be bonded to each other to form a ring,

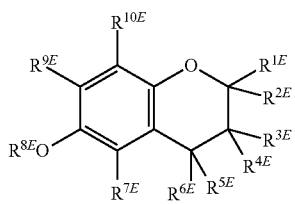

(E)

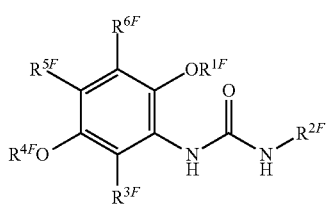

(F)

in Formula (E), $R^{1E}$, $R^{2E}$, $R^{3E}$, $R^{4E}$, $R^{5E}$, and $R^{6E}$ each independently represent a hydrogen atom or a monovalent organic group, $R^{7E}$, $R^{9E}$, and $R^{10E}$ each independently represent a hydrogen atom or a monovalent substituent, $R^{8E}$ represents a monovalent organic group, and $R^{1E}$ and $R^{2E}$, or $R^{3E}$ and $R^{4E}$ may be bonded to each other to form a ring, and in Formula (F), $R^{1F}$ and $R^{4F}$ each independently represent a monovalent organic group, and $R^{2F}$, $R^{3F}$, $R^{5F}$, and $R^{6F}$ each independently represent a hydrogen atom or a monovalent substituent.

2. The polymerizable liquid crystal composition according to claim 1, wherein the polymerizable liquid crystal compound is a liquid crystal compound represented by Formula (I), $L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2$ (I)

in Formula (I), $D^1$, $D^2$, $D^3$, and $D^4$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $G^1$ and $G^2$ each independently represent a divalent alicyclic hydrocarbon group having 5 to 8 carbon atoms, and one or more of —$CH_2$—'s constituting the alicyclic hydrocarbon group may be substituted with —O—, —S—, or —NH—, $A^1$ and $A^2$ each independently represent an aromatic ring having 6 or more carbon atoms or a cycloalkylene ring having 6 or more carbon atoms, $SP^1$ and $SP^2$ each independently represent a single bond, a linear alkylene group having 1 to 12 carbon atoms, a branched alkylene group having 3 to 12 carbon atoms, or a divalent linking group in which one or more of —$CH_2$—'s constituting the linear alkylene group having 1 to 12 carbon atoms or the branched alkylene group having 3 to 12 carbon atoms are substituted with —O—, —S—, —NH—, —N(Q)-, or —CO—, and Q represents a substituent, $L^1$ and $L^2$ each independently represent a monovalent organic group, and at least one of $L^1$ or $L^2$ represents a polymerizable group, provided that in a case where Ar is an aromatic ring represented by Formula (Ar-3), at least one of $L^1$, $L^2$, $L^3$ or $L^4$ in Formula (Ar-3) represents a polymerizable group, Ar represents any one aromatic ring selected from the group consisting of groups represented by Formulae (Ar-1) to (Ar-5),

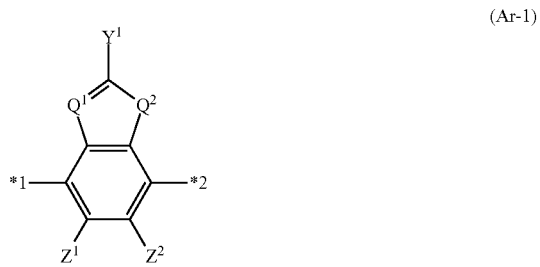

(Ar-1)

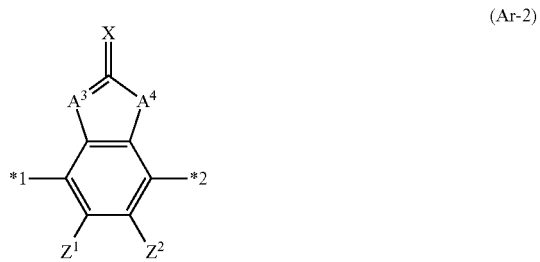

(Ar-2)

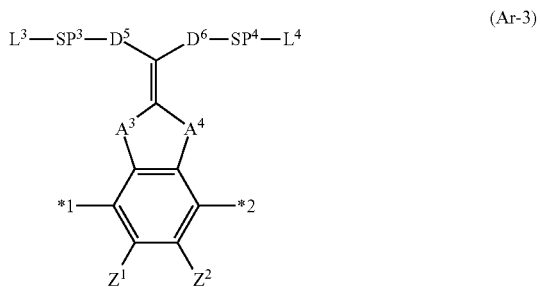

(Ar-3)

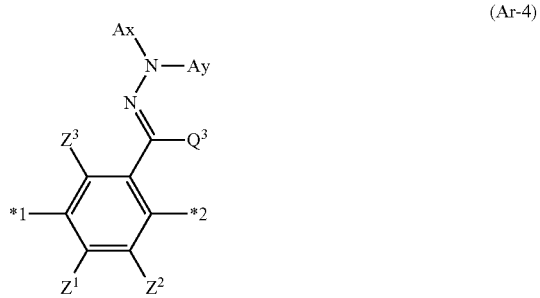

(Ar-4)

-continued

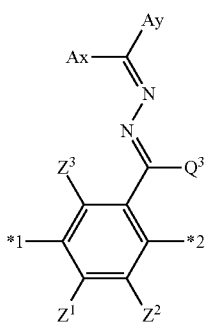

(Ar-5)

here, in Formulae (Ar-1) to (Ar-5), *1 represents a bonding position with $D^1$ and *2 represents a bonding position with $D^2$, $Q^1$ represents N or CH, $Q^2$ represents —S—, —O—, or —N($R^5$)—, and $R^5$ represents a hydrogen atom or an alkyl group having 1 to 6 carbon atoms, $Y^1$ represents an aromatic hydrocarbon group having 6 to 12 carbon atoms or aromatic heterocyclic group having 3 to 12 carbon atoms, which may have a substituent, $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$NR^6R^7$, or —$SR^8$, $R^6$ to $R^8$ each independently represent a hydrogen atom or an alkyl group having 1 to 6 carbon atoms, and $Z^1$ and $Z^2$ may be bonded to each other to form an aromatic ring, $A^3$ and $A^4$ each independently represent a group selected from the group consisting of —O—, —N($R^9$)—, —S—, and —CO—, and $R^9$ represents a hydrogen atom or a substituent, X represents a hydrogen atom or a non-metal atom of Groups 14 to 16 to which a substituent may be bonded, $D^5$ and $D^6$ each independently represent a single bond, —CO—O—, —C(═S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $SP^3$ and $SP^4$ each independently represent a single bond, a linear alkylene group having 1 to 12 carbon atoms, a branched alkylene group having 3 to 12 carbon atoms, or a divalent linking group in which one or more of —$CH_2$—'s constituting the linear alkylene group having 1 to 12 carbon atoms or the branched alkylene group having 3 to 12 carbon atoms are substituted with —O—, —S—, —NH—, —N(Q)-, or —CO—, and Q represents a substituent, $L^3$ and $L^4$ each independently represent a monovalent organic group, and at least one of $L^3$, $L^4$, or $L^1$ or $L^2$ in Formula (I) represents a polymerizable group, Ax represents an organic group having 2 to 30 carbon atoms, which has at least one aromatic ring selected from the group consisting of an aromatic hydrocarbon ring and an aromatic heterocyclic ring, Ay represents a hydrogen atom, an alkyl group having 1 to 6 carbon atoms which may have a substituent, or an organic group having 2 to 30 carbon atoms, which has at least one aromatic ring selected from the group consisting of an aromatic hydrocarbon ring and an aromatic heterocyclic ring, the aromatic rings in Ax and Ay may have a substituent, and Ax and Ay may be bonded to each other to form a ring, and $Q^3$ represents a hydrogen atom or an alkyl group having 1 to 6 carbon atoms which may have a substituent.

3. The polymerizable liquid crystal composition according to claim 2,
wherein a compound used for forming the aromatic rings represented by Formulae (Ar-1) to (Ar-5) represented by Ar in Formula (I) is a compound that contains a phenolic structure in which *1 and *2 in Formulae (Ar-1) to (Ar-5) represent hydroxyl groups, and a pKa of the is 5.8 to 10.0.

4. The polymerizable liquid crystal composition according to claim 1,
wherein a content of the aromatic polyether compound is 0.1 to 50 parts by mass with respect to 100 parts by mass of the polymerizable liquid crystal compound.

5. An optically anisotropic film comprising the polymerizable liquid crystal composition according to claim 1.

6. An optical film comprising the optically anisotropic film according to claim 5.

7. The optical film according to claim 6,
wherein the optically anisotropic film is a positive A plate or a positive C plate.

8. The optical film according to claim 6, comprising two or more layers of the optically anisotropic films,
wherein at least one of the layers is a positive A plate and at least one of the other layers is a positive C plate.

9. A polarizing plate comprising:
the optical film according to claim 6; and
a polarizer.

10. An image display device comprising the optical film according to claim 6.

11. An organic electroluminescent display device comprising:
an organic electroluminescent display panel; and
a circularly polarizing plate arranged on the organic electroluminescent display panel,
wherein the circularly polarizing plate includes a polarizer and the optical film according to claim 8.

* * * * *